(12) United States Patent
Huang

(10) Patent No.: US 11,391,740 B2
(45) Date of Patent: Jul. 19, 2022

(54) METHODS AND MATERIALS FOR IDENTIFYING AND TREATING CANCER

(71) Applicant: Mayo Foundation for Medical Education and Research, Rochester, MN (US)

(72) Inventor: Haojie Huang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 256 days.

(21) Appl. No.: 16/878,244

(22) Filed: May 19, 2020

(65) Prior Publication Data
US 2021/0003577 A1     Jan. 7, 2021

Related U.S. Application Data

(60) Provisional application No. 62/852,861, filed on May 24, 2019.

(51) Int. Cl.
| | | |
|---|---|---|
| *A61K 31/551* | (2006.01) | |
| *A61P 35/00* | (2006.01) | |
| *G01N 33/574* | (2006.01) | |
| *A61K 45/06* | (2006.01) | |

(52) U.S. Cl.
CPC ..... *G01N 33/57434* (2013.01); *A61K 31/551* (2013.01); *A61K 45/06* (2013.01); *G01N 2333/4703* (2013.01); *G01N 2333/90245* (2013.01)

(58) Field of Classification Search
CPC .............................. A61K 31/551; A61P 35/00
USPC .................................................. 514/220, 221
See application file for complete search history.

(56) References Cited

PUBLICATIONS

Antonarakis et al., "AR-V7 and Resistance to Enzalutamide and Abiraterone in Prostate Cancer," N. Engl. J. Medicine, Sep. 3, 2014, 371(11):1028-1038.
Arora et al., "Glucocorticoid Receptor Confers Resistance to Antiandrogens by Bypassing Androgen Receptor Blockade," Cell, Dec. 2013, 155(6):1309-1322.
Beer et al., "Enzalutamide in Metastatic Prostate Cancer before Chemotherapy," N. Engl. J. Medicine, Jun. 1, 2014, 371(5):424-433.
Beltran et al., "Divergent clonal evolution of castration-resistant neuroendocrine prostate cancer," Nat. Medicine, Mar. 2016, 22(3):298-305.
Bishop et al., "The Master Neural Transcription Factor BRN2 is an Androgen Receptor-Suppressed Driver of Neuroendocrine Differentiation in Prostate Cancer," Cancer Discovery, Jan. 2017, 7(1):54-71.
Bluemn et al., "Androgen Receptor Pathway-Independent Prostate Cancer is Sustained through FGF Signaling," Cancer Cell, Oct. 2017, 32(4):474-489.
De Bono et al., "Abiraterone and Increased Survival in Metastatic Prostate Cancer," N. Engl. J. Medicine, May 26, 2011, 364(21):1995-2005.
Decker et al., "Persistent androgen receptor-mediated transcription in castration-resistant prostate cancer under androgen-deprived conditions," Nucleic Acids Research, Sep. 27, 2012, 40(21):10765-10779.
Drost et al., "Organoid culture systems for prostate epithelial and cancer tissue," Nat. Protocols, Feb. 2016, 11(2):347-358.
Efstathiou et al., "Molecular Characterization of Enzalutamide-treated Bone Metastatic Castration-resistant Prostate Cancer," Eur. Urology, Jan. 2015, 67(1):53-60.
Fong et al., "Id-1 as a molecular target in therapy for breast cancer cell invasion and metastasis," Proc. Nat. Acad. Sci. USA, Nov. 2003, 100(23):13543-13548.
Grossmann et al., "Androgen Receptor Signaling in Androgen-Refractory Prostate Cancer," J. Natl. Cancer Institute, Nov. 2001, 93(22):1687-1697.
Guo et al., "ONECUT2 is a driver of neuroendocrine prostate cancer," Nat. Communications, Jan. 2019, 10:278, 13 pages.
He et al., "Ailanthone targets p23 to overcome MDV3100 resistance in castration-resistant prostate cancer," Nat. Communications, Dec. 2016, 7:13122, 14 pages.
He et al., "Androgen receptor splice variants bind to constitutively open chromatin and promote abiraterone-resistant growth of prostate cancer," Nucleic Acids Research, Jan. 4, 2018, 46(4):1895-1911.
Joseph et al., "A Clinically Relevant Androgen Receptor Mutation Confers Resistance to Second-Generation Antiandrogens Enzalutamide and ARN-509," Cancer Discovery, Sep. 2013, 3(9):1020-1029.
Ko et al., "Modulation of TET2 expression and 5-methylcytosine oxidation by the CXXC domain protein IDAX," Nature, May 2013, 497(7447):122-126.
Kohli et al., "Mutational Landscapes of Sequential Prostate Metastases and Matched Patient Derived Xenografts during Enzalutamide Therapy," PLoS One, Dec. 22. 2015, 10(12):e0145176, 14 pages.

(Continued)

*Primary Examiner* — Raymond J Henley, III
(74) *Attorney, Agent, or Firm* — Fish & Richardson P.C.

(57) ABSTRACT

This document provides methods and materials involved in identifying and/or treating mammals having a treatment-resistant prostate cancer (e.g., an enzalutamide-resistant, castration-resistant prostate cancer). For example, methods and materials for identifying a mammal (e.g., a human) having treatment-resistant prostate cancer (e.g., an enzalutamide-resistant, castration-resistant prostate cancer) as having an elevated level of one or more polypeptides (e.g., one or more of a CXXC5, a CXXC4, a TET2, an ID1, an ID3, and/or a PFN2 polypeptide) in treatment-resistant prostate tissue are provided. Methods and materials for administering one or more targeted therapies with or without one or more chemotherapeutic agents to a mammal having treatment-resistant prostate cancer identified as having an elevated level of one or more polypeptides (e.g., one or more of a CXXC5, a CXXC4, a TET2, an ID1, an ID3, and/or a PFN2 polypeptide) in treatment-resistant prostate tissue also are provided.

20 Claims, 38 Drawing Sheets
Specification includes a Sequence Listing.

(56) References Cited

PUBLICATIONS

Kumar et al., "Substantial interindividual and limited intraindividual genomic diversity among tumors from men with metastatic prostate cancer," Nat. Medicine, Apr. 2016, 22(4)369-378.
Langmead et al., "Fast gapped-read alignment with Bowtie 2," Nat. Methods, Apr. 2012, 9(4):357-359.
Long et al., "Ever-Changing Landscapes: Transcriptional Enhancers in Development and Evolution," Cell, Nov. 17, 2016, 167(5):1170-1187.
Long et al.. "ZF-CxxC domain-containing proteins, CpG islands and the chromatin connection," Biochem. Soc. Transactions, Jun. 2013, 41(3):727-740.
Lupien et al., "FoxA1 Translates Epigenetic Signatures into Enhancer-Driven Lineage-Specific Transcription," Cell, Mar. 2008, 132(6):958-970.
Lyden et al., "Id1 and Id3 are required for neurogenesis, angiogenesis and vascularization of tumour xenografts," Nature, Oct. 1999, 401(6754):670-677.
Ma et al., "Epigenetic regulator CXXC5 recruits DNA demethylase Tet2 to regulate TLR7/9-elicited IFN response in pDCs," J. Exp. Medicine, May 2017, 214(5):1471-1491.
McLean et al., "GREAT improves functional interpretation of cis-regulatory regions," Nat. Biotechnology, May 2010, 28(5):495-501.
Merseburger et al., "An update on enzalutamide in the treatment of prostate cancer," Ther. Adv. Urology, Feb. 2015, 7(1):9-21.
Miyamoto et al., "RNA-Seq of single prostate CTCs implicates noncanonical Wnt signaling in antiandrogen resistance," Science, 2015, 349(6254):1351-1356.
Nam et al., "High Levels of Id1 Expression Define B1 Type Adult Neural Stem Cells," Cell Stem Cell, Nov. 6, 2009, 5(5):515-526.
O'Brien et al., "ID1 and ID3 Regulate the Self-Renewal Capacity of Human Colon Cancer-Initiating Cells through p21," Cancer Cell, Jun. 12, 2012, 21(6):777-792.
Peng et al., "Jarid2/Jumonji Coordinates Control of PRC2 Enzymatic Activity and Target Gene Occupancy in Pluripotent Cells," Cell, Dec. 24, 2009, 139(7):1290-1302.
Pilo Boyl et al., "Profilin2 contributes to synaptic vesicle exocytosis, neuronal excitability, and novelty-seeking behavior," EMBO Journal, Jun. 2007, 26(12):2991-3002.
Quigley et al., "Genomic Hallmarks and Structural Variation in Metastatic Prostate Cancer," Cell, Jul. 26, 2018, 174(3):758-769.
Reid et al., "STEME: efficient EM to find motifs in large data sets," Nucleic Acids Research, Jul. 23, 2011, 39(18):e126, 10 pages.
Reilly et al., "Evolutionary changes in promoter and enhancer activity during human corticogenesis," Science, Mar. 6, 2015, 347(6226):1155-1159.
Robinson et al., "edgeR: a Bioconductor package for differential expression analysis of digital gene expression data," Bioinformatics, Jan. 2010, 26(1):139-140.
Rotinen et al., "ONECUT2 is a targetable master regulator of lethal prostate cancer that suppresses the androgen axis," Nat. Medicine, Dec. 2018, 24(12):1887-1898.
Sanyal et al., "The long-range interaction landscape of gene promoters," Nature, Sep. 6, 2012, 489(7414):109-113.
Scher et al., "Increased Survival with Enzalutamide in Prostate Cancer after Chemotherapy," N. Engl. J. Medicine, Sep. 27, 2012, 367(13):1187-1197.
Taitt, "Global Trends and Prostate Cancer: A Review of Incidence, Detection, and Mortality as Influenced by Race, Ethnicity, and Geographic Location," Am. J. Mens Health, Nov. 2018, 12(6):1807-1823.
Takeda et al., "A Somatically Acquired Enhancer of the Androgen Receptor is a Noncoding Driver in Advanced Prostate Cancer," Cell, Jul. 12, 2018, 174(2):422-432.
Tang et al., "Epigenetic regulation of Smad2 and Smad3 by profilin-2 promotes lung cancer growth and metastasis," Nat. Communications, Sep. 2015, 6:8230, 15 pages.
Viswanathan et al., "Structural Alterations Driving Castration-Resistant Prostate Cancer Revealed by Linked-Read Genome Sequencing," Cell, Jul. 12, 2018, 174(2):433-447.
Volpert et al., "Id1 regulates angiogenesis through transcriptional repression of thrombospondin-1," Cancer Cell, Dec. 2002, 2(6):473-483.
Wang et al., "Epidaurus: aggregation and integration analysis of prostate cancer epigenome," Nucleic Acids Research, Nov. 5, 2014, 43(2):e7, 9 pages.
Wang et al., "Reprogramming transcription by distinct classes of enhancers functionally defined by eRNA," Nature, Jun. 16, 2011, 474(7351):390-394.
Wang et al., "RSeQC: quality control of RNA-seq experiments," Bioinformatics, Aug. 2012, 28(16):2184-2185.
Watson et al., "Emerging mechanisms of resistance to androgen receptor inhibitors in prostate cancer," Nat. Rev. Cancer, Dec. 2015, 15(12):701-711.
Xu et al., "DNA Sequence Recognition of Human CXXC Domains and Their Structural Determinants," Structure, Jan. 2, 2018, 26(1):85-95.
You et al., "Integrated Classification of Prostate Cancer Reveals a Novel Luminal Subtype with Poor Outcome," Cancer Research, Sep. 1, 2016, 76(17):4948-4958.
Zhang et al., "Model-based analysis of ChIP-Seq (MACS)," Genome Biology, Nov. 2008, 9(9):R137, 9 pages.

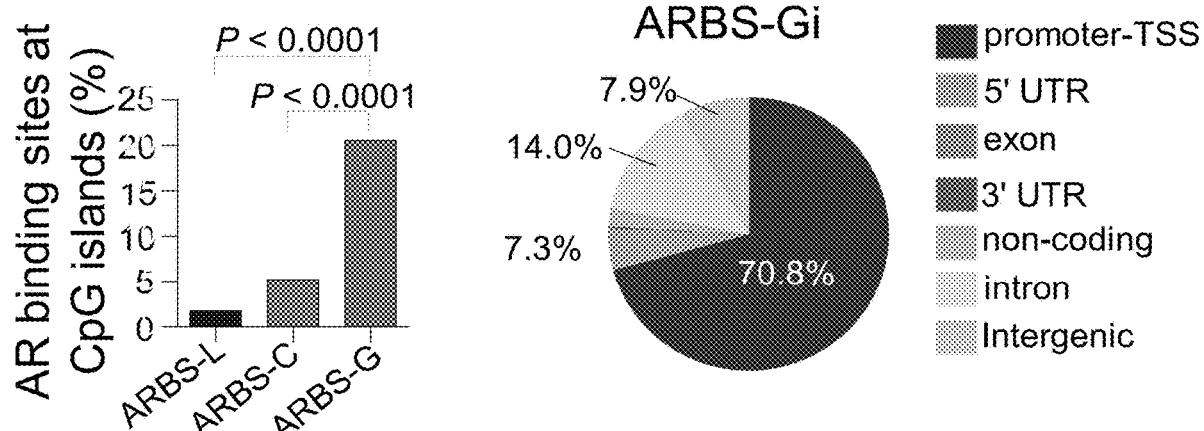
FIG. 2D
FIG. 2E
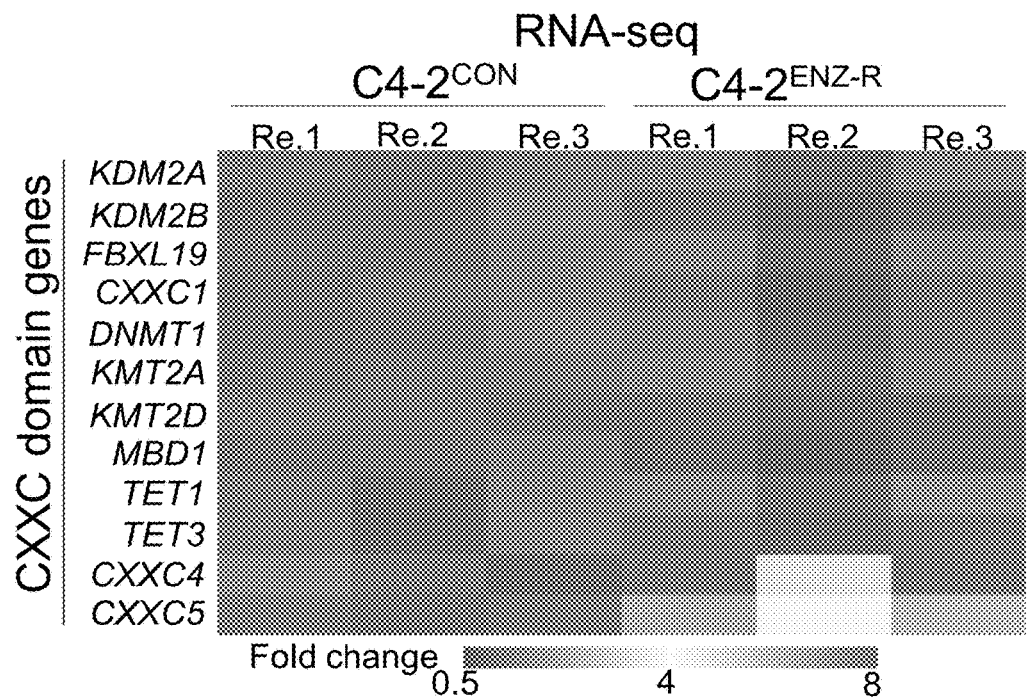
FIG. 2F

Neuron Part

Normalized Enrichment Score
(NES) = 2.07
P-value = 0.0

Organ Morphogenesis

Normalized Enrichment Score
(NES) = 1.786
P-value = 0.0

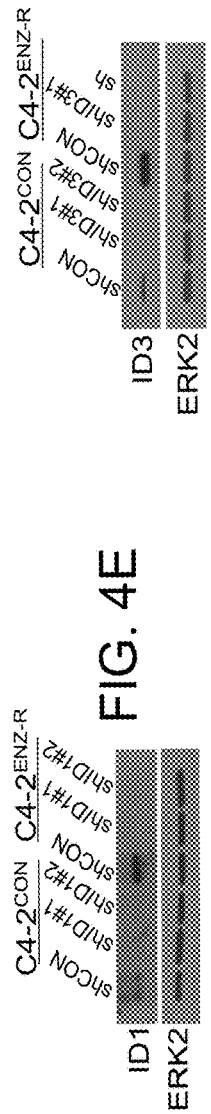
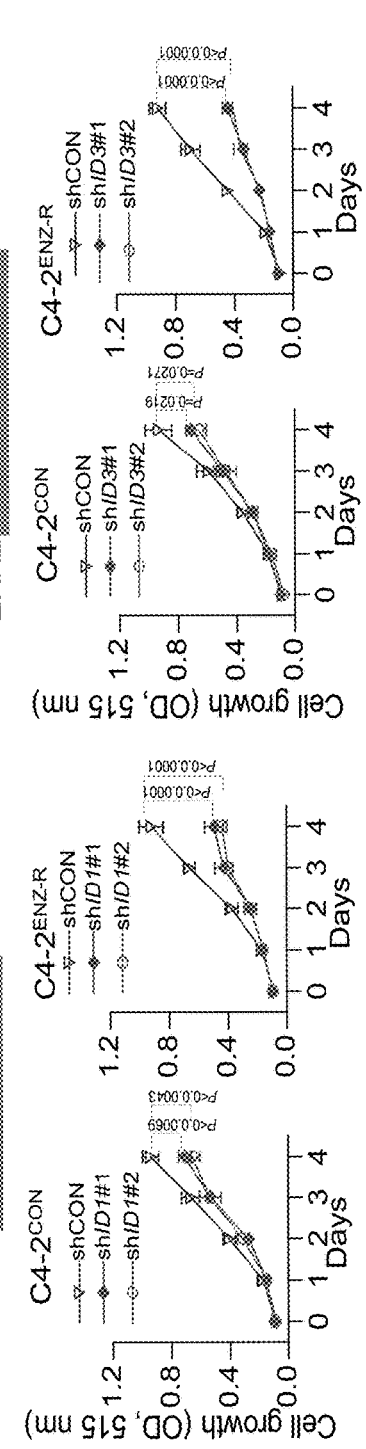
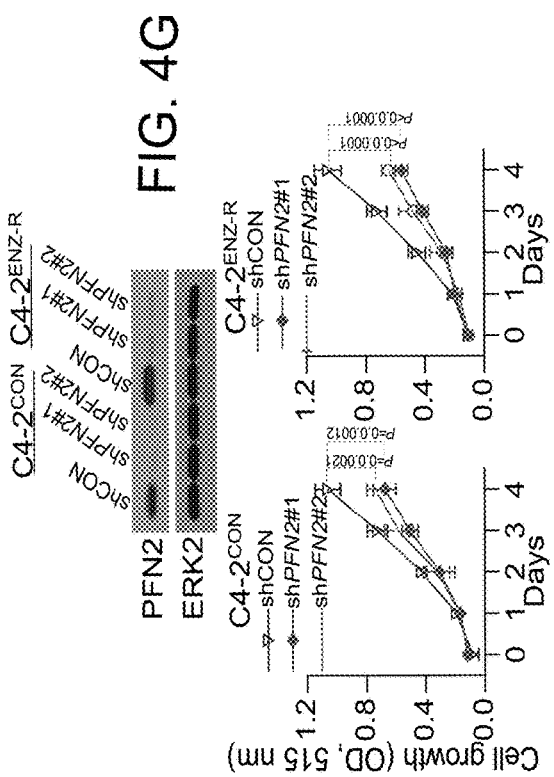

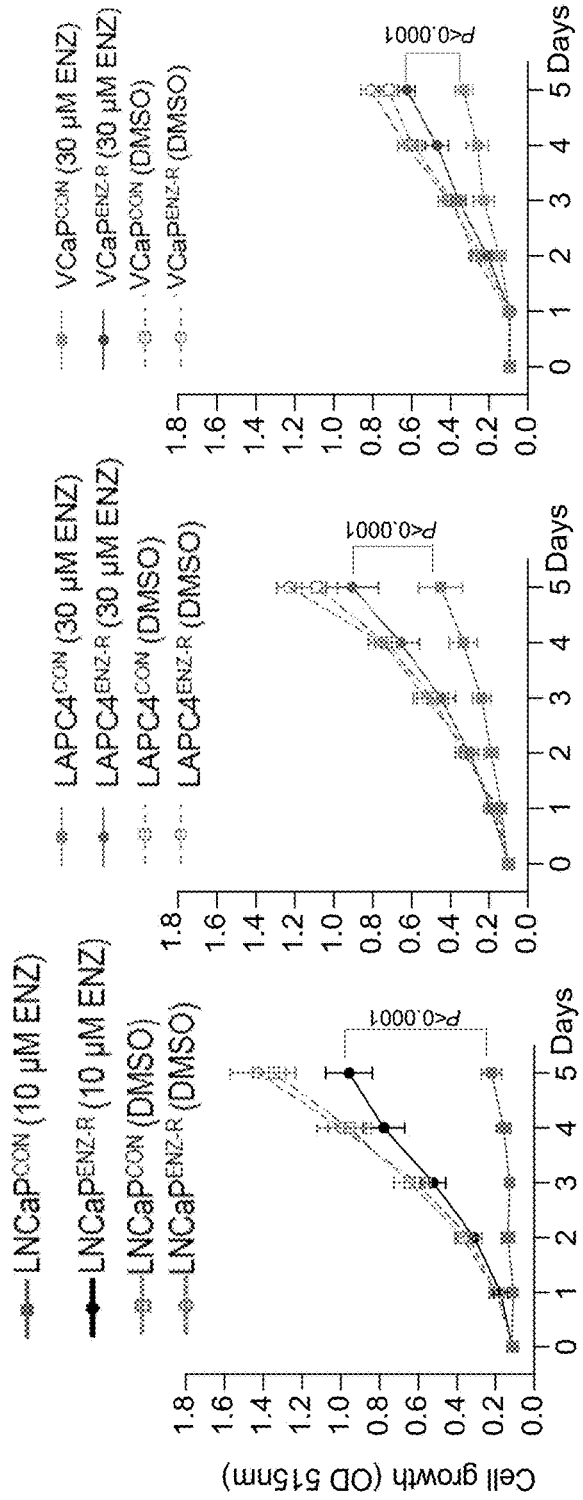
FIG. 8A
FIG. 8B
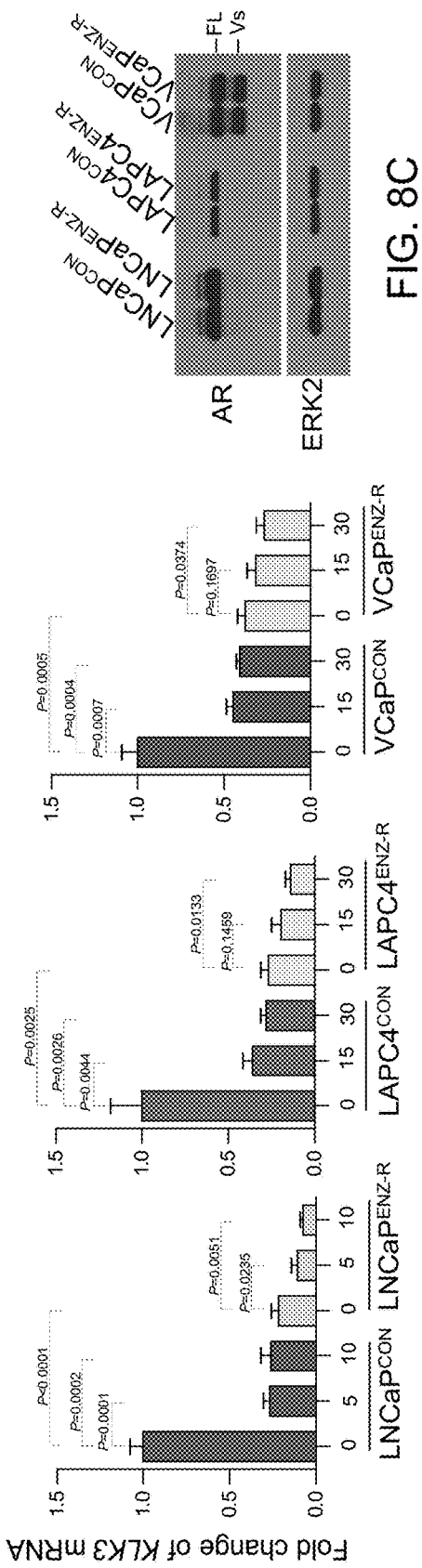
FIG. 8C

SEQUENCE LISTING

<160> NUMBER OF SEQ ID NOS: 34

<210> SEQ ID NO 1
<211> LENGTH: 16
<212> TYPE: DNA
<213> ORGANISM: Artificial
<220> FEATURE:
<223> OTHER INFORMATION: DNA motif enriched at ARBS-G binding regions

<400> SEQUENCE: 1
ssvvvvvvvv vvvvsg                                                      16

<210> SEQ ID NO 2
<211> LENGTH: 22
<212> TYPE: DNA
<213> ORGANISM: Homo sapiens

<400> SEQUENCE: 2
ccgggaaact gtggcgtgat gg                                               22

<210> SEQ ID NO 3
<211> LENGTH: 25
<212> TYPE: DNA
<213> ORGANISM: Homo sapiens

<400> SEQUENCE: 3
aggtggagga gtgggtgtcg ctgtt                                            25

<210> SEQ ID NO 4
<211> LENGTH: 20
<212> TYPE: DNA
<213> ORGANISM: Homo sapiens

<400> SEQUENCE: 4
ggtgagcaga gtgccctatc                                                  20

<210> SEQ ID NO 5
<211> LENGTH: 20
<212> TYPE: DNA
<213> ORGANISM: Homo sapiens

<400> SEQUENCE: 5
gaagaccttg cagcttccac                                                  20

<210> SEQ ID NO 6
<211> LENGTH: 20
<212> TYPE: DNA
<213> ORGANISM: Homo sapiens

<400> SEQUENCE: 6
gtttgcgcag tccacagaga                                                  20

<210> SEQ ID NO 7
<211> LENGTH: 20
<212> TYPE: DNA
<213> ORGANISM: Homo sapiens

<400> SEQUENCE: 7
ctctccctgc atggggtact                                                  20

<210> SEQ ID NO 8
<211> LENGTH: 20
<212> TYPE: DNA
<213> ORGANISM: Homo sapiens

```
<400> SEQUENCE: 8
aggctaggct gctttcgtag                                               20

<210> SEQ ID NO 9
<211> LENGTH: 20
<212> TYPE: DNA
<213> ORGANISM: Homo sapiens

<400> SEQUENCE: 9
gaatgtttgc cagcctcgtt                                               20

<210> SEQ ID NO 10
<211> LENGTH: 21
<212> TYPE: DNA
<213> ORGANISM: Homo sapiens

<400> SEQUENCE: 10
tggcagagct acgtggataa c                                             21

<210> SEQ ID NO 11
<211> LENGTH: 21
<212> TYPE: DNA
<213> ORGANISM: Homo sapiens

<400> SEQUENCE: 11
aaaccttccc ggtcttttcc t                                             21

<210> SEQ ID NO 12
<211> LENGTH: 20
<212> TYPE: DNA
<213> ORGANISM: Homo sapiens

<400> SEQUENCE: 12
gctctacgac atgaacggct                                               20

<210> SEQ ID NO 13
<211> LENGTH: 20
<212> TYPE: DNA
<213> ORGANISM: Homo sapiens

<400> SEQUENCE: 13
ggggttccaa cttcggattc                                               20

<210> SEQ ID NO 14
<211> LENGTH: 18
<212> TYPE: DNA
<213> ORGANISM: Homo sapiens

<400> SEQUENCE: 14
tgcctgtcgg aacgcagt                                                 18

<210> SEQ ID NO 15
<211> LENGTH: 19
<212> TYPE: DNA
<213> ORGANISM: Homo sapiens

<400> SEQUENCE: 15
atgtagtcga tgacgcgct                                                19

<210> SEQ ID NO 16
<211> LENGTH: 18
<212> TYPE: DNA
<213> ORGANISM: Homo sapiens
```

```
<400> SEQUENCE: 16
gtctgcggcg gtgttctg                                                  18

<210> SEQ ID NO 17
<211> LENGTH: 18
<212> TYPE: DNA
<213> ORGANISM: Homo sapiens

<400> SEQUENCE: 17
tgccgaccca gcaagatc                                                  18

<210> SEQ ID NO 18
<211> LENGTH: 20
<212> TYPE: DNA
<213> ORGANISM: Homo sapiens

<400> SEQUENCE: 18
ctggtggctg atagggata                                                 20

<210> SEQ ID NO 19
<211> LENGTH: 20
<212> TYPE: DNA
<213> ORGANISM: Homo sapiens

<400> SEQUENCE: 19
ggacaagggg ttagggagag                                                20

<210> SEQ ID NO 20
<211> LENGTH: 27
<212> TYPE: DNA
<213> ORGANISM: Homo sapiens

<400> SEQUENCE: 20
ggcctgggag tctcttgact ccactac                                        27

<210> SEQ ID NO 21
<211> LENGTH: 26
<212> TYPE: DNA
<213> ORGANISM: Homo sapiens

<400> SEQUENCE: 21
atgtggagcc caaaccacag aaaatg                                         26

<210> SEQ ID NO 22
<211> LENGTH: 21
<212> TYPE: RNA
<213> ORGANISM: Homo sapiens

<400> SEQUENCE: 22
cgugcagccu auugcgagau u                                              21

<210> SEQ ID NO 23
<211> LENGTH: 19
<212> TYPE: RNA
<213> ORGANISM: Homo sapiens

<400> SEQUENCE: 23
uagcgacuaa acacaucaa                                                 19

<210> SEQ ID NO 24
<211> LENGTH: 57
<212> TYPE: DNA
<213> ORGANISM: Homo sapiens
```

```
<400> SEQUENCE: 24
ccggcaacaa gatgaagagc accaactcga gttggtgctc ttcatcttgt tgttttt       57

<210> SEQ ID NO 25
<211> LENGTH: 57
<212> TYPE: DNA
<213> ORGANISM: Homo sapiens

<400> SEQUENCE: 25
ccggcctgct aatcaagtca cacatctcga gatgtgtgac ttgattagca ggttttt       57

<210> SEQ ID NO 26
<211> LENGTH: 57
<212> TYPE: DNA
<213> ORGANISM: Homo sapiens

<400> SEQUENCE: 26
ccggcaccaa tgtcaactcc aggatctcga gatcctggag ttgacattgg tgttttt       57

<210> SEQ ID NO 27
<211> LENGTH: 59
<212> TYPE: DNA
<213> ORGANISM: Homo sapiens

<400> SEQUENCE: 27
ccggcaacag aagaaaggc ttcttctcga gaagaagccc tttcttctgt tgtttttg       59

<210> SEQ ID NO 28
<211> LENGTH: 59
<212> TYPE: DNA
<213> ORGANISM: Homo sapiens

<400> SEQUENCE: 28
ccgggaaaga ctggccatca gatttctcga gaaatctgat ggccagtctt tcttttttg    59

<210> SEQ ID NO 29
<211> LENGTH: 54
<212> TYPE: DNA
<213> ORGANISM: Homo sapiens

<400> SEQUENCE: 29
ccggagtgtt ccgcaattta catctcgaga tgtaaattgc ggaacacttt tttg          54

<210> SEQ ID NO 30
<211> LENGTH: 54
<212> TYPE: DNA
<213> ORGANISM: Homo sapiens

<400> SEQUENCE: 30
ccgggtttat ccagaattag caactcgagt tgctaattct ggataaactt tttg          54

<210> SEQ ID NO 31
<211> LENGTH: 57
<212> TYPE: DNA
<213> ORGANISM: Homo sapiens

<400> SEQUENCE: 31
ccggcctact agtcaccaga gacttctcga gaagtctctg gtgactagta ggttttt       57

<210> SEQ ID NO 32
<211> LENGTH: 58
<212> TYPE: DNA
<213> ORGANISM: Homo sapiens
```

```
<400> SEQUENCE: 32
ccggcctact agtcaccaga gacttctcga gaagtctctg gtgactagta ggtttttg      58

<210> SEQ ID NO 33
<211> LENGTH: 58
<212> TYPE: DNA
<213> ORGANISM: Homo sapiens

<400> SEQUENCE: 33
ccgggctggt agagtcttgg tctttctcga gaaagaccaa gactctacca gcttttg      58

<210> SEQ ID NO 34
<211> LENGTH: 58
<212> TYPE: DNA
<213> ORGANISM: Homo sapiens

<400> SEQUENCE: 34
ccgggaaggc atactcaatg gcaaactcga gtttgccatt gagtatgcct tcttttg      58
```

METHODS AND MATERIALS FOR IDENTIFYING AND TREATING CANCER

CROSS-REFERENCE TO RELATED APPLICATIONS

This application claims the benefit of U.S. Provisional Application Ser. No. 62/852,861, filed May 24, 2019. The disclosure of the prior application is considered part of (and is incorporated by reference in) the disclosure of this application.

STATEMENT AS TO FEDERALLY SPONSORED RESEARCH

This invention was made with government support under CA130908 awarded by National Institutes of Health. The government has certain rights in the invention.

BACKGROUND

1. Technical Field

This document relates to methods and materials involved in identifying and/or treating mammals having a treatment-resistant prostate cancer (e.g., an enzalutamide-resistant, castration-resistant prostate cancer). For example, this document provides methods and materials for identifying a mammal (e.g., a human) having treatment-resistant prostate cancer (e.g., an enzalutamide-resistant, castration-resistant prostate cancer) as having an elevated level of one or more polypeptides (e.g., one or more of a CXXC5, a CXXC4, a TET2, an ID1, an ID3, and/or a PFN2 polypeptide) in treatment-resistant prostate tissue. This document also provides methods and materials for administering one or more targeted therapies with or without one or more chemotherapeutic agents to a mammal having treatment-resistant prostate cancer identified as having an elevated level of one or more polypeptides (e.g., one or more of a CXXC5, a CXXC4, a TET2, an ID1, an ID3, and/or a PFN2 polypeptide) in treatment-resistant prostate tissue.

2. Background Information

Globally, prostate cancer is the fifth leading cause of cancer-related death in men (Taitt, *Am. J Mens Health*, 12(6):1807-23 (2018)). Patients with advanced prostate cancer undergo testosterone suppression via surgical or medical castration with most patients progressing to castration-resistant prostate cancer (CRPC). CRPC is a highly morbid state of prostate cancer (Merseburger et al., *Ther. Adv. Urol.*, 7(1):9-21 (2015)). Chemotherapy benefits only a subset of patients owing to tolerability and performance concerns. CRPC patients treated with enzalutamide, an androgen receptor inhibitor, show significant improvement in survival (Scher et al., *New Engl. J Med.*, 376:1187-1197 (2012)). However, a subset of CRPC patients develop resistance to enzalutamide (Efstathiou et al., *Eur. Urol.*, 67(1):53-60 (2014)). Thus, there remains an unmet need in the management of CRPC.

SUMMARY

This document provides methods and materials involved in identifying and/or treating mammals having a treatment-resistant prostate cancer (e.g., an enzalutamide-resistant, castration-resistant prostate cancer). For example, this document provides methods and materials for identifying a mammal (e.g., a human) having treatment-resistant prostate cancer (e.g., an enzalutamide-resistant, castration-resistant prostate cancer) as having an elevated level of one or more polypeptides (e.g., one or more of a CXXC finger protein 5 (CXXC5), a CXXC finger protein 4 (CXXC4), a tet methylcytosine dioxygenase 2 (TET2), an inhibitor of DNA binding 1 (ID1), an inhibitor of DNA binding 3 (ID3), and/or a profilin 2 (PFN2) polypeptide) within treatment-resistant prostate tissue. In such cases, the mammal can be classified as having treatment-resistant prostate cancer that includes an elevated level of one or more polypeptides (e.g., one or more of a CXXC5, a CXXC4, a TET2, an ID1, an ID3, and/or a PFN2 polypeptide) in treatment-resistant prostate tissue. Identifying mammals (e.g., humans) as having treatment-resistant prostate cancer that includes an elevated level of one or more polypeptides (e.g., one or more of a CXXC5, a CXXC4, a TET2, an ID1, an ID3, and/or a PFN2 polypeptide) in treatment-resistant prostate tissue can allow clinicians and patients to proceed with appropriate treatment options. As described herein, mammals (e.g., humans) with treatment-resistant prostate cancers identified as having an elevated level of one or more polypeptides (e.g., one or more of a CXXC5, a CXXC4, a TET2, an ID1, an ID3, and/or a PFN2 polypeptide) can be sensitive to inhibition by one or more targeted therapies (e.g., one or more BET inhibitors and/or one or more CBP/p300 inhibitors).

This document also provides methods and materials for treating treatment-resistant prostate cancer. For example, a mammal (e.g., a human) having treatment-resistant prostate cancer and identified as having an elevated level of one or more polypeptides (e.g., one or more of a CXXC5, a CXXC4, a TET2, an ID1, an ID3, and/or a PFN2 polypeptide) in treatment-resistant prostate tissue can be administered one or more targeted therapies and/or one or more chemotherapeutic agents to reduce symptoms of the prostate cancer (e.g., enzalutamide, abiraterone, and/or Apalutamide). In some cases, a mammal (e.g., a human) having treatment-resistant prostate cancer and identified as having an elevated level of one or more polypeptides (e.g., one or more of a CXXC5, a CXXC4, a TET2, an ID1, an ID3, and/or a PFN2 polypeptide) in treatment-resistant prostate tissue can be effectively treated using one or more targeted therapies (e.g., one or more BET inhibitors, CBP/p300 inhibitors, and/or BET-CBP/p300 dual inhibitors) and/or one or more chemotherapeutic agents (e.g., docetaxel) to reduce symptoms of the prostate cancer (e.g., JQ1, BETi, and/or CPI637). In some cases, having the ability to administer one or more targeted therapies and/or one or more chemotherapeutic agents to a mammal (e.g., a human) having treatment-resistant prostate cancer and identified as having an elevated level of one or more polypeptides (e.g., one or more of a CXXC5, a CXXC4, a TET2, an ID1, an ID3, and/or a PFN2 polypeptide) in the treatment-resistant prostate tissue can allow clinicians and patients to treat treatment-resistant prostate cancer effectively. For example, one or more chemotherapeutic agents may not be effective against treatment-resistant prostate cancer. In such cases, administering one or more targeted therapies in addition to or as an alternative to chemotherapy can be used to treat the otherwise treatment-resistant prostate cancer effectively.

In some cases, identification of the one or more elevated polypeptides can be involved in the diagnosis and/or management of a mammal (e.g., a human) with treatment-resistant prostate cancer. For example, a mammal (e.g., a human) having treatment-resistant prostate cancer (e.g., treatment-resistant prostate cancer with prostate tissue having an elevated level of one or more of a CXXC5, a CXXC4, a TET2, an ID1, an ID3, and/or a PFN2 polypeptide) can be administered one or more targeted therapies and/or one or more chemotherapeutic agents to treat treatment-resistant prostate cancer. In some cases, the response to treatment can be monitored by examining a prostate biopsy for a reduction or elimination of one or more the elevated levels of one or more polypeptides (e.g., one or more of a CXXC5, a CXXC4, a TET2, an ID1, an ID3, and/or a PFN2).

In general, one aspect of this document features a method for identifying a mammal having a treatment-resistant prostate cancer as having an elevated level of one or more polypeptides within prostate tissue of the mammal. The method comprises (or consists essentially of or consists of) (a) detecting the presence of an elevated level of a polypeptide in prostate tissue of the mammal as compared to a median level of the polypeptide present within control prostate tissue, wherein the polypeptide is selected from the group consisting of a CXXC5 polypeptide, a CXXC4 polypeptide, a TET2 polypeptide, an ID1 polypeptide, an ID3 polypeptide, and a PFN2 polypeptide, and (b) classifying the mammal as having the elevated level within the prostate tissue. The mammal can be a human. The treatment-resistant prostate cancer can be an enzalutamide-resistant prostate cancer. The treatment-resistant prostate cancer can be an enzalutamide-resistant castration-resistant prostate cancer. The method can comprise detecting the presence of an elevated level of two or more polypeptides of the group. The treatment-resistant prostate cancer can comprise an AR polypeptide within the prostate tissue of the mammal. The treatment-resistant prostate cancer can lack a PSA polypeptide within the prostate tissue of the mammal. The treatment-resistant prostate cancer can comprise the AR polypeptide and can lack the PSA polypeptide in the prostate tissue of the mammal.

In another aspect, this document features a method for treating treatment-resistant prostate cancer. The method comprises (or consists essentially of or consists of) (a) identifying a mammal having a treatment-resistant prostate cancer as having an elevated level of a polypeptide as compared to a median level present within a control prostate tissue, wherein the polypeptide is selected from the group consisting of a CXXC5 polypeptide, a CXXC4 polypeptide, a TET2 polypeptide, an ID1 polypeptide, an ID3 polypeptide, and a PFN2 polypeptide, and (b) administering one or more targeted therapies to the mammal. The mammal can be a human. The treatment-resistant prostate cancer can be an enzalutamide-resistant prostate cancer. The treatment-resistant prostate cancer can be an enzalutamide-resistant castration-resistant prostate cancer. The identifying step can comprise detecting the presence of two or more polypeptides of the group. The method can comprise administering the two or more targeted therapies to the mammal. The treatment-resistant prostate cancer can comprise an AR polypeptide within the prostate tissue of the mammal. The treatment-resistant prostate cancer can lack an elevated level of a PSA polypeptide within the prostate tissue of the mammal. The treatment-resistant prostate cancer can comprise the AR polypeptide and can lack the PSA polypeptide in the prostate tissue of the mammal. The administering one or more targeted therapies can comprise administering a BET inhibitor. The BET inhibitor can be JQ1. The administering one or more targeted therapies can comprise administering a CBP/p300 inhibitor. The CBP/p300 inhibitor can be CPI637. The administering one or more targeted therapies can comprise administering the CBP/p300 and the BET inhibitor. The administering one or more targeted therapies can comprise administering the JQ1 and administering the CPI637. The administering step can further comprise administering one or more chemotherapeutic agents.

In another aspect, this document features a method for treating treatment-resistant prostate cancer. The method comprises (or consists essentially of or consists of) administering, to a mammal having treatment-resistant prostate cancer and identified as having an elevated level of a polypeptide, one or more targeted therapies, wherein the polypeptide is selected from the group consisting of a CXXC5 polypeptide, a CXXC4 polypeptide, a TET2 polypeptide, an ID1 polypeptide, an ID3 polypeptide, and a PFN2 polypeptide. The mammal can be a human. The treatment-resistant prostate cancer can be an enzalutamide-resistant prostate cancer. The treatment-resistant prostate cancer can be an enzalutamide-resistant castration-resistant prostate cancer. The method can comprise administering the two or more targeted therapies to the mammal. The treatment-resistant prostate cancer can comprise an AR polypeptide within the prostate tissue of the mammal. The treatment-resistant prostate cancer can lack a PSA polypeptide within the prostate tissue of the mammal. The treatment-resistant prostate cancer can comprise the AR polypeptide and can lack the PSA polypeptide in the prostate tissue of the mammal. The administering the one or more targeted therapies can comprise administering a BET inhibitor. The BET inhibitor can be JQ1. The administering the one or more targeted therapies can comprise administering a CBP/p300 inhibitor. The CBP/p300 inhibitor can be CPI637. The administering the one or more targeted therapies can comprise administering the CBP/p300 and the BET inhibitor. The administering one or more targeted therapies can comprise administering the JQ1 and administering the CPI637. The administering further can comprise administering one or more chemotherapeutic agents.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 4A-4I. ARBS-Gi target genes drive ENZ resistance in ARPC. A: Western blot analysis of AR, CXXC5, CXXC4, TET2, ID1, ID3, PFN2, and FOXA1 protein level in C4-2CON and C4-2ENZ-R cell lines. ERK2 was used as a loading control. B-C: RT-qPCR showing the mRNA level of AR, CXXC5, CXXC4, TET2, ID1, ID3, PFN2, ID1, PFN2, ID3, KLK3, TMPRSS2, and NKX3.1 genes in C4-2CON and AR knockdown C4-2ENZ-R cells (b) or in control and AR knockdown C4-2ENZ-R cells (c). Data shown as means±s.d. (n=3). D: Western blot analysis of AR, CXXC5, CXXC4, TET2, ID1, ID3, and PFN2 protein expression in C4-2ENZ-R cells at 96 hours after infection with lentivirus expressing the indicated shRNAs. E-G: ID1 (e), ID3 (f) or PFN2 (g) was knocked down individually by gene-specific shRNAs in C4-2CON and C4-2ENZ-R cells, and cell proliferation was measured by SRB assay. Data are represented as means±s.d. n=6. H: Western blot analysis of AR, CXXC5, CXXC4, TET2, ID1, ID3, and PFN2 protein expression in control or ENZ-resistant LNCaP, VCaP, or LAPC4 cells. I: Relative cell proliferation of control or ENZ-resistant LNCaP, VCaP, or LAPC4 cells infected with the lentivirus expressing the indicated shRNAs. Data are represented as means±s.d. n=6.

FIGS. 8A-8D. ENZ-resistant ARPC cell models established from different cell lines. A: Control and ENZ-resistant cell lines established from LNCaP, LAPC4, and VCaP cells (LNCaPCON, LNCaPENZ-R, LAPC4CON, LAPC4ENZ-R, VCaPCON, and VCaPENZ-R) were treated with the indicated concentrations of ENZ, and cell proliferation was measured by SRB assay. Data are represented as means±s.d., n=6. Statistical significance was determined by two-way ANOVA. B: RT-qPCR showing the mRNA level of KLK3 in control and ENZ-resistant cell lines established from LNCaP, LAPC4, and VCaP cells (LNCaPCON, LNCaPENZ-R, LAPC4CON, LAPC4ENZ-R, VCaPCON, and VCaPENZ-R) treated with the indicated concentrations of ENZ for 24 hours. Data are represented as means±s.d., n=3. Statistical significance was determined by unpaired two-tailed Student's t tests. C: Western blot analysis showing the protein level of full-length (FL) AR and AR variants (Vs) in cell lines indicated. ERK2 was used as a loading control. D: AR gene was knocked down by specific shRNAs in LNCaPCON, LNCaPENZ-R, LAPC4CON, LAPC4ENZ-R, VCaPCON, and VCaPENZ-R cells, and the cell proliferation as indicated was measured by SRB assay. Data are represented as means±s.d. n=5. Statistical significance was determined by two-way ANOVA.

DETAILED DESCRIPTION

Figure 1A:
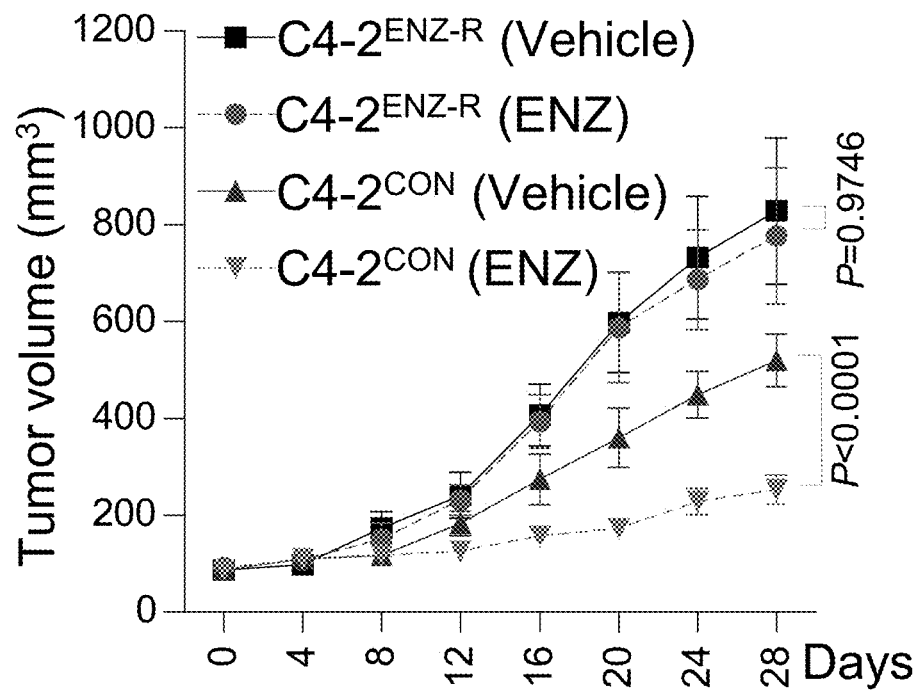
FIGS. 1A-1G. Genome-wide profiling of AR chromatin binding in ENZ-resistant PCa cells. A: Effect of ENZ treatment on growth of C4-2CON and C4-2ENZ-R xenografts in mice. C4-2ENZ-R and C4-2CON cells suspended in 0.1 mL matrigel were injected into the right flank of 6-week old male SCID mice. After the volume of tumor nodules reached about 100 mm$^3$, mice were randomly assigned within control and ENZ-resistant groups and were treated with ENZ at 10 mg/kg or vehicle per day and tumor volume was measured every 4 days. B: After 28 days of treatment, tumors were isolated from mice in each group and photographed. Data are represented as means±s.d., n=8. Statistical significance was determined by two-way ANOVA. C: Immunofluorescent cytochemistry showing the cellular location of AR protein in C4-2CON and C4-2ENZ-R cells. Scale bar, 10 µm. D: AR was knocked down by specific shRNAs in C4-2CON and C4-2ENZ-R cells, and cell proliferation was measured by SRB assay. Data are represented as means±s.d. n=6. Statistical significance was determined by two-way ANOVA. E: Venn diagram showing AR chromatin binding peaks in C4-2CON and C4-2ENZ-R cells detected by ChIP-seq. F: Heatmaps showing ChIP-seq read intensity of AR, H3K27ac, and FOXA1 in C4-2CON and C4-2ENZ-R cells. G: CEAS genomic analysis of the lost (L), conserved (C), and gained (G) AR binding sites (ARBS) identified in C4-2CON and C4-2ENZ-R cells.

This document provides methods and materials for identifying and/or treating mammals having a treatment-resistant prostate cancer (e.g., an enzalutamide-resistant, castration-resistant prostate cancer). For example, this document provides methods and materials for identifying a mammal (e.g., a human) having treatment-resistant prostate cancer as having an elevated level of one or more polypeptides (e.g., one or more of a CXXC5, a CXXC4, a TET2, an ID1, an ID3, and/or a PFN2) in treatment-resistant prostate tissue. This document also provides methods and materials for administering one or more targeted therapies with or without one or more chemotherapeutic agents to a mammal having treatment-resistant prostate cancer identified as having an elevated level of one or more polypeptides (e.g., one or more of a CXXC5, a CXXC4, a TET2, an ID1, an ID3, and/or a PFN2).

Any appropriate mammal having a treatment-resistant prostate cancer can be identified as having an elevated level of one or more polypeptides (e.g., one or more of a CXXC5, a CXXC4, a TET2, an ID1, an ID3, and/or a PFN2 polypeptide). For example, humans and other primates such as monkeys having a treatment-resistant prostate cancer can be identified as having an elevated level of one or more polypeptides (e.g., one or more of a CXXC5, a CXXC4, a TET2, an ID1, an ID3, and/or a PFN2 polypeptide) within treatment-resistant prostate cancer. In some cases, any appropriate mammal having a treatment-resistant prostate cancer can be identified as having an elevated level of one or more polypeptides (e.g., one or more of a CXXC5, a CXXC4, a TET2, an ID1, an ID3, and/or a PFN2) and as having an androgen receptor (AR) polypeptide. For example, humans and other primates such as monkeys having a treatment-resistant prostate cancer can be identified as having an elevated level of one or more polypeptides (e.g., one or more of a CXXC5, a CXXC4, a TET2, an ID1, an ID3, and/or a PFN2 polypeptide) and as having an AR polypeptide within treatment-resistant prostate tissue. In some cases, dogs, cats, horses, cows, pigs, sheep, mice, or rats having a treatment-resistant prostate cancer can be identified as having an elevated level of one or more polypeptides (e.g., one or more of a CXXC5, a CXXC4, a TET2, an ID1, an ID3, and/or a PFN2 polypeptide) and/or as having an AR polypeptide within treatment-resistant prostate tissue. In some cases, any appropriate mammal having a treatment-resistant prostate cancer can be identified as having an elevated level of one or more polypeptides (e.g., one or more of a CXXC5, a CXXC4, a TET2, an ID1, an ID3, and/or a PFN2 polypeptide), as having an AR polypeptide, and as not having a prostate specific antigen (PSA) polypeptide within treatment-resistant prostate tissue.

Any appropriate method can be used to determine if a mammal (e.g., a human) has prostate tissue (e.g., a prostate biopsy) having (a) an elevated level of one or more polypeptides (e.g., one or more of a CXXC5, a CXXC4, a TET2, an ID1, an ID3, and/or a PFN2 polypeptide), (b) an androgen receptor (AR) polypeptide, and/or (c) a prostate-specific antigen (PSA) polypeptide. In some cases, any appropriate method can be used to determine if a mammal (e.g., a human) has treatment-resistant prostate tissue (a) having an elevated level of one or more polypeptides (e.g., one or more of a CXXC5, a CXXC4, a TET2, an ID1, an ID3, and/or a PFN2 polypeptide), (b) having an AR polypeptides, and (c) not having a PSA polypeptides. For example, techniques such as immunohistochemistry (IHC) techniques, immunofluorescence (IF) techniques, mass spectrometry-based proteomics, or Western blot techniques can be used to determine if a mammal (e.g., a human) has prostate tissue having an elevated level of one or more polypeptides (e.g., one or more of a CXXC5, a CXXC4, a TET2, an ID1, an ID3, and/or a PFN2 polypeptide). In some cases, mRNA levels can be used as an indicator of polypeptide levels. In some cases, mRNA levels can be used to determine whether prostate tissue has elevated levels of the one or more polypeptides. Any appropriate method of quantifying mRNA can be used to determine whether prostate tissue has elevated levels of the one or more polypeptides (e.g., one or more of a CXXC5, a CXXC4, a TET2, an ID1, an ID3, and/or a PFN2 polypeptide) and/or to determine the presence or absence of an AR polypeptide and/or to determine the presence or absence of a PSA polypeptide. Examples of methods of quantifying mRNA include, without limitation, qRT-PCR, RNA-sequencing, microfluidic capillary electrophoresis, and in situ hybridization.

In some cases, a prostate tissue sample obtained from a mammal can be stained using an anti-CXXC5 antibody to determine if the mammal has prostate tissue having an elevated level of CXXC5 polypeptides. In some cases, a prostate tissue sample obtained from a mammal can be stained using an anti-CXXC4 antibody to determine if the mammal has prostate tissue having an elevated level of CXXC4 polypeptides. In some cases, a prostate tissue sample obtained from a mammal can be stained using an anti-TET2 antibody to determine if the mammal has prostate tissue having an elevated level of TET2 polypeptides. In some cases, a prostate tissue sample obtained from a mammal can be stained using an anti-ID1 antibody to determine if the mammal has prostate tissue having an elevated level of ID1 polypeptides. In some cases, a prostate tissue sample obtained from a mammal can be stained using an anti-ID3 antibody to determine if the mammal has prostate tissue having an elevated level of ID3 polypeptides. In some cases, a prostate tissue sample obtained from a mammal can be stained using an anti-PFN2 antibody to determine if the mammal has prostate tissue having an elevated level of PFN2 polypeptides. In some cases, a prostate tissue sample obtained from a mammal can be stained using an anti-AR antibody to determine if the mammal has prostate tissue having AR polypeptides. In some cases, a prostate tissue sample obtained from a mammal to be tested can be stained using an anti-PSA antibody to determine if the mammal has prostate tissue having PSA polypeptides.

Any appropriate sample can be used to determine if a mammal (e.g., a human) has prostate tissue (a) having an elevated level of one or more polypeptides (e.g., one or more of a CXXC5, a CXXC4, a TET2, an ID1, an ID3, and/or a PFN2 polypeptide), (b) an AR polypeptide, and/or having or lacking a PSA polypeptide. For example, prostate tissue biopsies obtained from a mammal (e.g., a human) can be used to determine if a mammal (e.g., a human) has prostate tissue having an elevated level of one or more polypeptides (e.g., one or more of a CXXC5, a CXXC4, a TET2, an ID1, an ID3, and/or a PFN2 polypeptide). In some cases, a mammal (e.g., human) may be identified as having normal prostate tissue (e.g., no prostate cancer with or without the one or more polypeptides as described herein having elevated levels). Prostate tissue can be obtained from a mammal (e.g., a human) having treatment-resistant prostate cancer (e.g., enzalutamide-resistant, castration-resistant prostate cancer). Prostate tissue can be obtained from a mammal (e.g., a human) having treatment-resistant prostate cancer (e.g., enzalutamide-resistant, castration-resistant prostate cancer) having previously received one or more chemotherapeutic agents (e.g., docetaxel). Prostate tissue can be obtained from a mammal (e.g., a human) having treatment-resistant prostate cancer (e.g., enzalutamide-resistant, castration-resistant prostate cancer) having previously received one or more target-therapies (e.g., abiraterone and apalutamide). Prostate tissue can be obtained from a mammal (e.g., a human) having treatment-resistant prostate cancer (e.g., enzalutamide-resistant, castration-resistant prostate cancer) having previously received one or more chemotherapeutic agents (e.g., docetaxel) and one or more targeted therapies (e.g., enzalutamide, apalutamide, and/or abiraterone). Prostate tissue can be obtained from a mammal (e.g., a human) having treatment-resistant prostate cancer (e.g., enzalutamide-resistant prostate cancer) but not having received castration therapy. Prostate tissue can be obtained from a mammal (e.g. a human) having hormone naïve prostate cancer.

The term "elevated level" as used herein with respect to a particular polypeptide (e.g., one or more of a CXXC5, a CXXC4, a TET2, an ID1, an ID3, and/or a PFN2 polypeptide) refers to a level of that polypeptide present within prostate tissue that is greater (e.g., at least 10, 25, 35, 45, 50, 55, 65, 75, 80, 90, or 100 percent greater) than the median level of that polypeptide as present within control prostate tissue of comparable mammals. Examples of such control tissue include, without limitation, prostate tissue having a prostate cancer not resistant to enzalutamide (e.g., a hormone naïve prostate cancer) or prostate tissue not having a prostate cancer (e.g., healthy prostate tissue).

Once a mammal (e.g., a human) having treatment-resistant prostate cancer is identified as having an elevated level of one or more polypeptides (e.g., one or more of a CXXC5, a CXXC4, a TET2, an ID1, an ID3, and/or a PFN2 polypeptide) as described herein, the mammal can be classified as having treatment-resistant prostate cancer that includes the presence of an elevated level of one or more polypeptides (e.g., one or more of a CXXC5, a CXXC4, a TET2, an ID1, an ID3, and/or a PFN2 polypeptide). In some cases, once a mammal having treatment-resistant prostate cancer is identified as having an elevated level of one or more polypeptides (e.g., one or more of a CXXC5, a CXXC4, a TET2, an ID1, an ID3, and/or a PFN2 polypeptide) and having an AR polypeptide as described herein, the mammal can be classified as having treatment-resistant prostate cancer that includes the presence of an elevated level of one or more polypeptides (e.g., one or more of a CXXC5, a CXXC4, a TET2, an ID1, an ID3, and/or a PFN2 polypeptide) and the presence of an AR polypeptide. In some cases, once a mammal having treatment having treatment-resistant prostate cancer is identified as having an elevated level of one or more polypeptides (e.g., one or more of a CXXC5, a CXXC4, a TET2, an ID1, an ID3, and/or a PFN2 polypeptide), having an AR polypeptide, and not having a PSA polypeptide as described herein, the mammal can be classified as having treatment-resistant prostate cancer that includes the presence of an elevated level of one or more polypeptides (e.g., one or more of a CXXC5, a CXXC4, a TET2, an ID1, an ID3, and/or a PFN2 polypeptide), the presence of an AR polypeptide, and the absence of a PSA polypeptide.

In some cases, a mammal (e.g., a human) having treatment-resistant prostate cancer that is identified as having an elevated level of CXXC5 as described herein can be classified as having treatment-resistant prostate cancer that includes treatment-resistant prostate tissue having an elevated level of a CXXC5 polypeptide. In some cases, a mammal (e.g., a human) having treatment-resistant prostate cancer that is identified as having an elevated level of CXXC4 as described herein can be classified as having treatment-resistant prostate cancer that includes treatment-resistant prostate tissue having an elevated level of a CXXC4 polypeptide. In some cases, a mammal (e.g., a human) having treatment-resistant prostate cancer that is identified as having an elevated level of TET2 as described herein can be classified as having treatment-resistant prostate cancer that includes treatment-resistant prostate tissue having an elevated level of a TET2 polypeptide. In some cases, a mammal (e.g., a human) having treatment-resistant prostate cancer that is identified as having an elevated level of ID1 as described herein can be classified as having treatment-resistant prostate cancer that includes treatment-resistant prostate tissue having an elevated level of a ID1 polypeptide. In some cases, a mammal (e.g., a human) having treatment-resistant prostate cancer that is identified as having an elevated level of ID3 as described herein can be classified as having treatment-resistant prostate cancer that includes treatment-resistant prostate tissue having an elevated level of a ID3 polypeptide. In some cases, a mammal (e.g., a human) having treatment-resistant prostate cancer that is identified as having an elevated level of PFN2 as described herein can be classified as having treatment-resistant prostate cancer that includes treatment-resistant prostate tissue having an elevated level of a PFN2 polypeptide.

As described herein, this document also provides methods and materials for treating a mammal having treatment-resistant prostate cancer. For example, a mammal (e.g., a human) having treatment-resistant prostate cancer that is identified as having an elevated level of one or more polypeptides (e.g., one or more of a CXXC5, a CXXC4, a TET2, an ID1, an ID3, and/or a PFN2 polypeptide) as described herein can be treated with one or more chemotherapeutic agents and/or one or more targeted therapies. In another example, a mammal (e.g., a human) having treatment-resistant prostate cancer that is identified as having an elevated level of one or more polypeptides (e.g., one or more of a CXXC5, a CXXC4, a TET2, an ID1, an ID3, and/or a PFN2 polypeptide) and having an AR polypeptide as described herein can be treated with one or more chemotherapeutic agents and/or one or more targeted therapies. In yet another example, a mammal (e.g., a human) having treatment-resistant prostate cancer that is identified as having an elevated level of one or more polypeptides (e.g., CXXC5, CXXC4, TET2, ID1, ID3 and/or PFN2), having an AR polypeptide, and not having a PSA polypeptide as described herein can be treated with one or more chemotherapeutic agents or one or more targeted therapies. In some cases, a mammal (e.g., a human) having treatment-resistant prostate cancer that is identified as having an elevated level of one or more polypeptides (e.g., one or more of a CXXC5, a CXXC4, a TET2, an ID1, an ID3, and/or a PFN2 polypeptide) as described herein can be administered, or instructed to self-administer, one or more chemotherapeutic agents and/or one or more targeted therapies to treat treatment-resistant prostate cancer.

Any appropriate chemotherapeutic agent can be administered to a mammal (e.g., a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide)) to treat treatment-resistant prostate cancer. Any appropriate chemotherapeutic agent can be administered to a mammal (e.g., a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide) and having an AR polypeptide) to treat treatment-resistant prostate cancer. Any appropriate chemotherapeutic agent can be administered to a mammal (e.g., a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide), having an AR polypeptide, and not having a PSA polypeptide) to treat treatment-resistant prostate cancer. In some cases, a chemotherapeutic agent used as described herein to treat treatment-resistant prostate cancer can reduce symptoms of prostate within a mammal cancer (e.g., cancer metastasis, pain, and/or overall mortality). Example of chemotherapeutic agents that can be used as described herein to treat prostate cancer include, without limitation, docetaxel (Taxotere) and cabazitaxel (Jevtana).

Any appropriate targeted therapy can be administered to a mammal (e.g., a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide)) to treat treatment-resistant prostate cancer. Any appropriate targeted therapy can be administered to a mammal (e.g., a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide) and having an AR polypeptide) to treat treatment-resistant prostate cancer. Any appropriate targeted therapy can be administered to a mammal (e.g., a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide), having an AR polypeptide, and not having a PSA polypeptide) to treat treatment-resistant prostate cancer. In some cases, a targeted therapy used as described herein to treat prostate cancer can reduce symptoms of prostate cancer within a mammal (e.g., cancer metastasis, pain, and/or overall mortality). Examples of targeted therapies that can be used as described herein to treat treatment-resistant prostate cancer include, without limitation, antiandrogens/antagonists (e.g., enzalutamide, apalutamide, and abiraterone), bromodomain and extra-terminal (BET) inhibitors (JQ1 and BETi), CREB-binding protein (CBP)/p300 inhibitors (CPI637), and immunotherapy (sipuleucel-T (Provenge)).

In some cases, two or more (e.g., two, three, four, five, six, or more) targeted therapies can be administered to a mammal (e.g., (a) a mammal having treatment-resistant prostate cancer and identified as having an elevated level of one or more polypeptides (e.g., one or more of a CXXC5, a CXXC4, a TET2, an ID1, an ID3, and/or a PFN2 polypeptide); (b) a mammal having treatment-resistant prostate cancer and identified as having an elevated level of one or more polypeptides (e.g., one or more of a CXXC5, a CXXC4, a TET2, an ID1, an ID3, and/or a PFN2 polypeptide) and having an AR polypeptide; or (c) a mammal having treatment-resistant prostate cancer and identified as having an elevated level of one or more polypeptides (e.g., one or more of a CXXC5, a CXXC4, a TET2, an ID1, an ID3, and/or a PFN2 polypeptide), having an AR polypeptide, and not having a PSA polypeptide) to treat treatment-resistant prostate cancer. For example, two targeted therapies (e.g., a BET inhibitor and a CBP/p300 inhibitor) can be administered to a mammal having treatment-resistant prostate cancer that was identified as having an elevated level of one or more polypeptides (e.g., one or more of a CXXC5, a CXXC4, a TET2, an ID1, an ID3, and/or a PFN2 polypeptide).

In some cases, one or more chemotherapeutic and one or more targeted therapies can be administered to a mammal having treatment-resistant prostate cancer (e.g., (a) a mammal having treatment-resistant prostate cancer and identified as having an elevated level of one or more polypeptides (e.g., one or more of a CXXC5, a CXXC4, a TET2, an ID1, an ID3, and/or a PFN2 polypeptide); (b) a mammal having treatment-resistant prostate cancer and identified as having an elevated level of one or more polypeptides (e.g., one or more of a CXXC5, a CXXC4, a TET2, an ID1, an ID3, and/or a PFN2 polypeptide) and having an AR polypeptide; or (c) a mammal having treatment-resistant prostate cancer and identified as having an elevated level of one or more polypeptides (e.g., one or more of a CXXC5, a CXXC4, a TET2, an ID1, an ID3, and/or a PFN2 polypeptide), having an AR polypeptide, and not having a PSA polypeptide).

In some cases, one or more chemotherapeutic and/or one or more targeted therapies can be administered to a mammal once or multiple times over a period of time ranging from days to months. In some cases, one or more chemotherapeutic and/or one or more targeted therapies can be given to achieve remission of treatment-resistant prostate cancer, and then given during follow up periods to prevent relapse of the treatment-resistant prostate cancer. In some cases, one or more chemotherapeutic and/or one or more targeted therapies can be formulated into a pharmaceutically acceptable composition for administration to a mammal (e.g., a human) having treatment-resistant prostate cancer to reduce symptoms of prostate within that mammal (e.g., tumor metastasis, pain, and/or overall mortality). For example, a therapeutically effective amount of one or more chemotherapeutic and/or one or more targeted therapies can be formulated together with one or more pharmaceutically acceptable carriers (additives) and/or diluents. In some cases, a therapeutically effective amount of one or more chemotherapeutic agents and/or one or more targeted therapies can be individually formulated with one or more pharmaceutically acceptable carriers (additives) and/or diluents. A pharmaceutical composition can be formulated for administration in solid or liquid form including, without limitation, in the form of sterile solutions, suspensions, sustained-release formulations, tablets, capsules, pills, powders, or granules.

One or more chemotherapeutic agents active against a treatment-resistant prostate cancer can be administered to a mammal once or multiple times over a period of time ranging from days to months or years. In some cases, one or more chemotherapeutic agents can be formulated into a pharmaceutically acceptable composition for administration to a mammal. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more chemotherapeutic and/or one or more targeted therapies active against a treatment-resistant prostate cancer can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more chemotherapeutic and/or one or more targeted therapies can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the treatment-resistant prostate cancer, the route of administration, the age and general health condition of the subject, excipient usage, the possibility of co-usage with other therapeutic treatments, and the judgment of the treating physician.

An effective amount of a composition containing one or more chemotherapeutic and/or one or more targeted therapies described herein can be any amount that reduces the number of cancer cells within a mammal (e.g., a human) without producing severe toxicity to the mammal. For example, an effective amount of docetaxel can be from about 3.5 mg/kg of body weight to 35 mg/kg of body weight daily. For example, an effective amount of a CBP/p300 inhibitor can be from about 10 mg/kg of body weight to 100 mg/kg of body weight daily. For example, an effective amount of a BET inhibitor can be from about 10 mg/kg of body weight to 100 mg/kg of body weight daily. If a particular mammal fails to respond to a particular amount, then the amount of the chemotherapeutic agent can be increased by, for example, two fold. If a particular mammal fails to respond to a particular amount, then the amount of the targeted therapy can be increased by, for example, two fold. After receiving the higher amount of either one or both of the one or more chemotherapeutic and/or one or more targeted therapies, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., treatment-resistant prostate cancer) may require an increase or decrease in the actual effective amount administered.

The frequency of administration of one/or more targeted therapies and one or more chemotherapeutic agents described herein can be any amount that reduces the number of treatment-resistant prostate cancer cells within a mammal (e.g., a human) without producing significant toxicity to the mammal. For example, the frequency of administration of docetaxel can be from about once a day to about once a month (e.g., from about once a week to about once every other week). For example, the frequency of administration of a CBP/p300 inhibitor (e.g., CPI637) can be from about once a day to about once a week (e.g., once every other day). The frequency of administration of a BET inhibitor (e.g., JQ1) can be from about once a day to about once a week (e.g., once every other day). The frequency of administration of two or more targeted therapies (e.g., a BET inhibitor and a CBP/p300 inhibitor) can be from about once a day to about once a week (e.g., once every other day or 5 days per week). The frequency of administration of two or more targeted therapies (e.g., a BET inhibitor and a CBP/p300 inhibitor) can be designed to administer one targeted therapy on one day and the second targeted therapy on the next day and maintaining this pattern during the course of treatment (e.g., orally). The frequency of administration of a one/or more targeted therapies and one or more chemotherapeutic agents described herein can remain constant or can be variable during the duration of treatment. A course of treatment with a composition containing one/or more targeted therapies and one or more chemotherapeutic agents described herein can include rest periods. For example, a composition containing one/or more targeted therapies and one or more chemotherapeutic agents described herein can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one/or more targeted therapies and one or more chemotherapeutic agents described herein can be any duration that reduces the number of treatment-resistant prostate cancer cells within a mammal (e.g., a human) without producing significant toxicity to the mammal. In some cases, the effective duration can vary from several days to several months. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to the condition being treated (e.g., treatment-resistant prostate cancer) can be monitored. Any appropriate method can be used to determine whether or not a mammal having treatment-resistant prostate cancer is being treated. For example, clinical scanning techniques can be used to determine the presence or absence of treatment-resistant prostate cancer within a mammal (e.g., a human) being treated.

The invention will be further described in the following examples, which do not limit the scope of the invention described in the claims.

EXAMPLES

Example 1—AR Addiction Drives Enzalutamide Resistance in Prostate Cancer

Materials and Methods
Chromatin Immunoprecipitation (ChIP), ChIP-Sequencing (ChIP-Seq) and Bioinformatics Analyses ChIP experiments were performed as described previously (He et al., *Nucleic Acids Res.*, 46:1895-1911 (2018)). In brief, chromatin was cross-linked for 15 minutes at room temperature with 11% formaldehyde/PBS solution added to cell culture medium. Cross-linked chromatin was then sonicated, diluted and immunoprecipitated with Protein G-plus Agarose beads (Bio-Rad®) prebound with antibodies at 4° C. overnight. Precipitated protein-DNA complexes were eluted and cross-linking was reversed at 65° C. for 12 h. ChIP-seq libraries were prepared using previously described methods (Peng et al., *Cell,* 139:290-1302 (2009)). High-throughput sequencing (51 nucleotide, pair-end) was performed using the Illumina HiSeq™4000 platforms at the Mayo Clinic Genome Analysis Core Facility. All short reads were mapped to the human reference genome (hg19/GRCh37) using bowtie2 (version 2.1.0) with default configurations (Langmead et al., *Nature Methods,* 9:357-359 (2012)). On average, 81.7 million reads were obtained that were uniquely mapped to the reference genome for each sample. These uniquely mapped reads were then used for peak calling. MACS2 (version 2.0.10) was used to identify peaks with input samples used as background and a q-value cutoff of 0.05 (macs2 callpeak-bdg-SPMRX-f BAM) (Zhang et al., *Genome Biol.,* 9:R137 (2008)). Peaks located in satellite repeats and centromere regions were removed. ChIP-seq tag intensity tracks (bedGraph files) were generated by MACS2, and then were converted into bigWig files using UCSC "wigToBigWig" tool. Genomic distribution of peaks with regard to transcription start sites (TSS) and the association of peaks to target genes were performed by Genomic Regions Enrichment of Annotations Tool (GREAT) (McLean et al., *Nat. Biotechnol.,* 28:495-501 (2010)). Histone modification profiles were generated by Epidaurus (Wang et al., *Nucleic Acids Res.,* 43:e7 (2015)).
RNA-Seq Analyses and Real-Time PCR For RNA-seq, libraries were prepared using Illumina's TruSeq RNA prep kit and standard protocol. The RNA libraries were sequenced as 51 nt pair-end reads at one sample per lane of an Illumina HiSeq 2500, generating an average of 265 million reads per sample. Fragment size was estimated by RSeQC using the first 1,000,000 read pairs that were uniquely mapped (Wang, et al., *Bioinformatics,* 28:2184-2185 (2012).). All reads were aligned to the human reference genome (hg19/GRCh37) by TopHat 2.0.9 using these options. Gene expression counts were generated using HTseq software (http://www-huber.embl.de/users/anders/HTSeq/doc/overview.html) from Illumina gene annotation files (http://support.illumina.com/sequencing/sequencing_software/igenome.html). Gene expression analysis was conducted using EdgeR (version 3.6.8) and the built-in "TMM" (trimmed mean of M-values) normalization method was used (Robinson et al., *Bioinformatics,* 26:139-140 (2010)). Differentially expressed genes were determined based on the false discovery rate (FDR) threshold 0.01 and fold change (FC=log 2(siARV/siNT)) threshold of 1. Specifically, upregulated genes were defined as those with FDR≤0.01 and FC≥1 and down-regulated genes were defined as those with FDR≤0.01 and FC≤−1. Gene expression was determined by real-time quantitative PCR (qPCR) using Power SYBR Green (Cat No. 4368708, Thermo Fisher). Primer sequences used for qPCR were as listed in Table 1.

TABLE 1

| RT-qPCR primers | Sequence |
|---|---|
| GAPDH-Forward | 5'-CCGGGAAACTGTGGCGTGATGG-3' (SEQ ID NO: 2) |
| GAPDH-Reverse | 5'-AGGTGGAGGAGTGGGTGTCGCTGTT-3' (SEQ ID NO: 3) |
| AR-Forward | 5'-GGTGAGCAGAGTGCCCTATC-3' (SEQ ID NO: 4) |
| AR-Reverse | 5'-GAAGACCTTGCAGCTTCCAC-3' (SEQ ID NO: 5) |
| CXXC5-Forward | 5'-GTTTGCGCAGTCCACAGAGA-3' (SEQ ID NO: 6) |
| CXXC5-Reverse | 5'-CTCTCCCTGCATGGGTACT-3' (SEQ ID NO: 7) |
| TET2-Forward | 5'-AGGCTAGGCTGCTTTCGTAG-3' (SEQ ID NO: 8) |
| TET2-Reverse | 5'-GAATGTTTGCCAGCCTCGTT-3' (SEQ ID NO: 9) |
| PFN2-Forward | 5'-TGGCAGAGCTACGTGGATAAC-3' (SEQ ID NO: 10) |
| PFN2-Reverse | 5'-AAACCTTCCCGGTCTTTTCCT-3' (SEQ ID NO: 11) |
| IDI-Forward | 5'-GCTCTACGACATGAACGGCT-3' (SEQ ID NO: 12) |
| IDI-Reverse | 5'-GGGGTTCCAACTTCGGATTC-3' (SEQ ID NO: 13) |
| ID3-Forward | 5'-TGCCTGTCGGAACGCAGT-3' (SEQ ID NO: 14) |
| ID3-Reverse | 5'-ATGTAGTCGATGACGCGCT-3' (SEQ ID NO: 15) |
| KLK3-Forward | 5'-GTCTGCGGCGGTGTTCTG-3' (SEQ ID NO: 16) |
| KLK3-Reverse | 5'-TGCCGACCCAGCAAGATC-3' (SEQ ID NO: 17) |
| TMPRSS2-Forward | 5'-CTGGTGGCTGATAGGGGATA-3' (SEQ ID NO: 18) |
| TMPRSS2-Reverse | 5'-GGACAAGGGGTTAGGGAGAG-3' (SEQ ID NO: 19) |
| NKX3-1-Forward | 5'-GGCCTGGGAGTCTCTTGACTCCACTAC-3' (SEQ ID NO: 20) |
| NKX3-1-Reverse | 5'-ATGTGGAGCCCAAACCACAGAAAATG-3' (SEQ ID NO: 21) |
| siRNA and shRNA | Sequence |
| AR siRNA | 5'-CGUGCAGCCUAUUGCGAGAUU-3' (SEQ ID NO: 22) |
| controls siRNA | 5'-UAGCGACUAAACACAUCAA-3' (SEQ ID NO: 23) |
| control shRNA | 5'-CCGGCAACAAGATGAAGAGCACCAACTCGAGTTGGTGCTCTTCATCTTGTTGTTTTT-3' (SEQ ID NO: 24) |
| AR shRNA #1 | 5'-CCGGCCTGCTAATCAAGTCACACATCTCGAGATGTGTGACTTGATTAGCAGGTTTTT-3' (SEQ ID NO: 25) |
| AR shRNA #2 | 5'-CCGGCACCAATGTCAACTCCAGGATCTCGAGATCCTGGAGTTGACATTGGTGTTTTT-3' (SEQ ID NO: 26) |
| CXXC5 shRNA #1 | 5'-CCGGCAACAGAAGAAAGGGCTTCTTCTCGAGAAGAAGCCCTTTCTTCTGTTGTTTTTG-3' (SEQ ID NO: 27) |
| CXXC5 shRNA #2 | 5'-CCGGGAAAGACTGGCCATCAGATTTCTCGAGAAATCTGATGGCCAGTCTTTCTTTTTG-3' (SEQ ID NO: 28) |
| TET2 shRNA #1 | 5'-CCGGAGTGTTCCGCAATTTACATCTCGAGATGTAAATTGCGGAACACTTTTTTG-3' (SEQ ID NO: 29) |
| TET2 shRNA #2 | 5'-CCGGGTTTATCCAGAATTAGCAACTCGAGTTGCTAATTCTGGATAAACTTTTTG-3' (SEQ ID NO: 30) |
| ID1 shRNA #1 | 5'-CCGGCCTACTAGTCACCAGAGACTTCTCGAGAAGTCTCTGGTGACTAGTAGGTTTTT-3' (SEQ ID NO: 31) |
| ID1 shRNA #2 | 5'-CCGGCCTACTAGTCACCAGAGACTTCTCGAGAAGTCTCTGGTGACTAGTAGGTTTTTG-3' (SEQ ID NO: 32) |
| PFN2 shRNA #1 | 5'-CCGGGCTGGTAGAGTCTTGGTCTTTCTCGAGAAAGACCAAGACTCTACCAGCTTTTTG-3' (SEQ ID NO: 33) |
| PFN2 shRNA #2 | 5'-CCGGGAAGGCATACTCAATGGCAAACTCGAGTTTGCCATTGAGTATGCCTTCTTTTTG-3' (SEQ ID NO: 34) |

STEME and Pathway Analysis

Efficient EM to find motifs in large data sets (STEME) (Reid et al., *Nucleic acids research*, 39:e126 (2011)) was used to find the enriched motif at androgen receptor (AR) gained binding sites in the C4-2ENZ-R cell line. Gene set enrichment analyses (GSEA) was carried out using the signature scores per gene (z-scores) in pre-ranked mode with default settings. A volcano plot was used to illustrate the magnitude of fold-change for top-scoring (z-scores) genes in the signature. DAVID Bioinformatics Resources v6.7, a web-based functional annotation tool for data analysis (http://david.abcc.ncifcrf.gov/home.jsp), was used to perform gene ontology (GO) analysis for the Top 500 differentially expressed genes in the C4-2ENZ-R cell line.

Cell Lines and Cell Culture

LNCaP, VCaP, LAPC4 PCa, and 293T cell lines were purchased from ATCC. C4-2 cells were purchased from Uro Corporation (Oklahoma City, Okla.). C4-2, LNCaP, VCaP, and LAPC4 cells were maintained at 37° C. and 5% $CO_2$ in RPMI 1640 medium containing 10% fetal bovine serum (FBS) and 1% antibiotic/antimycotic (Thermo Fisher Scientific). 293T cells were maintained in DMEM medium with 10% FBS. To establish enzalutamide resistant cell lines, C4-2, LNCaP, VCaP and LAPC4 cells were cultured in medium containing enzalutamide. Concentrations of enzalutamide in the medium were gradually increased to 30 µM for C4-2, VCaP and LAPC4 cell lines. LNCaP was grown in medium containing up to 5 µM enzalutamide. Control cell lines were cultured in medium with the same concentration of vehicle only (DMSO).

Lentiviral shRNA Infection and Cell Proliferation Assays 293T cells were co-transfected with control shRNA or shRNA specific for human AR, CXXC5, TET2, ID1, ID3 and PFN2. Using Lipofectamine 2000, the shRNA plasmids were co-transfected into 293T cells along with packing and envelop plasmids, according to the manufacturer's instructions. At two days post-transfection, virus particles containing shRNA were collected and used to infect PCa cells, according to the protocol provided by Sigma-Aldrich. Individual shRNAs specifically targeting human AR, CXXC5, TET2, ID1, ID3 and PFN2 were obtained from Sigma-Aldrich and their sequences are listed in Table 1. The indicated cells were transduced by culturing with a 1:1 mixture of fresh medium and virus supernatant with Polybrene (4 μg/mg final concentration) (Sigma-Aldrich) for 24 h. For the cell proliferation analysis, the indicated cells infected with lentiviruses containing shAR, shCXXC5, shTET2, shID1, shID3, shPFN2 or control shRNA were seeded in 96-well plates (3,000 cells/well) and cultured in medium containing 10% Complete Classic Medium (CSS). Cells were fixed at different time points (day 0-5) and cell growth was measured using a sulforhodamine B (SRB) assay (He et al., Nature Commun., 7:13122 (2016)).

Animal Experiments and Drug Treatment

NOD-SCID male mice were generated in house and used for animal experiments. All mice were housed under standard conditions with a 12 hour light/dark cycle and access to food and water ad libitum and maintained under pathogen-free conditions. The animal study was approved by the Institutional Animal Care and Use Committee (IACUC) at the Mayo Clinic. C4-2ENZ-R cells ($3 \times 10^6$) were mixed with Matrigel (in 50 μl of 1×PBS: 50 μl of Matrigel (BD Biosciences)) and injected subcutaneously into the right flank of 6 week-old castrated mice. After xenografts reached a size of approximately 100 mm$^3$, the animals were randomized and placed into one of five treatment groups (n=10 per group), including vehicle (10% DMSO, 40% polyethylene glycol 400 and 50% saline), ENZ (10 milligram (mg) per kilogram (kg) of bodyweight), CPI637 (10 mg per kg of bodyweight), JQ1 (50 mg per kg of bodyweight) and a combination of CPI637 (10 mg per kg of bodyweight) and JQ1(50 mg per kg of bodyweight). For the ENZ-resistant PC patient-derived xenograft tumor (PDX) study, PDXs were generated in the laboratory as previously reported (Kohli et al., PloS one, 10:e0145176 (2015)). PDXs were established by passaging tumor fragments (~1 mm$^3$) subcutaneously (s.c.) into 6 week-old castrated mice. After xenografts reached a size of approximately 100 mm$^3$, animals were randomly assigned into five treatment groups (n=8 per group) as same as the C4-2ENZ-R xenograft study. Mice were treated 5 days per week by oral gavage and tumor growth was measured in a blinded fashion using digital calipers. The tumor volume was calculated using the following equation: tumor volume=length×width×width×0.5.

Immunohistochemistry (IHC)

The prostate cancer tissue specimens used for immunohistochemistry (IHC) were obtained from FFPE tumor samples (e.g., from patients, PDXs, or C4-2ENZ-R xenograft tumors), were deparaffinized, rehydrated, and subjected to heat-mediated antigen retrieval. The UltraSensitive S-P (Rabbit) IHC Kit (KIT-9706, Fuzhou Maixin Biotech) was used for IHC. Briefly, sections were incubated with 3% $H_2O_2$ for 15 minutes at room temperature to quench endogenous peroxidase activity. After antigen retrieval using unmasking solution (Vector Labs), slides were blocked with normal goat serum for 1 hour and then incubated with a primary antibody at 4° C. overnight. IHC analysis of tumor samples was performed using primary antibodies against CXXC5 (dilution 1:500; #16513-1-AP, Proteintech), CXXC4 (dilution 1:500; #ab105400, Abcam), AR (dilution 1:1000; #ab108341, Abcam), ID1 (dilution 1:1000; #ab66495, Abcam), PFN2 (1:1000; #LS-C186004-100, LSBio), and TET2 (dilution 1:1000; #ab94580, Abcam). The sections were then washed three times in 1×PBS and treated for 30 minutes with biotinylated goat-anti-rabbit IgG secondary antibodies (Fuzhou Maixin Biotech). After washing three times in 1×PBS, sections were incubated with streptavidin-conjugated HRP (Fuzhou Maixin Biotech). After washing three times in 1×PBS for 5 minutes each, specific detection was developed with 3,3'-diaminobenzidine (DAB-2031, Fuzhou Maixin Biotech). Images were acquired using a Leica camera and matched software. IHC staining was scored by two independent pathologists on the basis of the "most common" criteria. Staining score=Staining intensity× Staining positivity. Staining intensity was graded into four categories: 0, 1, 2 and 3. Specifically, 0=no nuclear staining, 1=weak nuclear staining (staining obvious only at ×400), 2=medium nuclear staining (staining obvious at ×100 but not×40), and 3=strong nuclear staining (staining obvious at ×40). For staining positivity, 0=no positive cells, 1=<10% of positive cells, 2=10-50% positive cells, 3=51-70% positive cells, and 4=>70% positive cells.

Western Blot

Cells were treated as described herein and then lysed by boiling for 10 minutes in sample buffer (2% SDS, 10% glycerol, 10%-Mercaptoethanol, Bromphenol Blue, and Tris-HCl, pH 6.8). Equal amounts of protein (50-100 μg) from cell lysates were denatured in sample buffer (Thermo Fisher Scientific), subjected to SDS-polyacrylamide gel electrophoresis, and transferred to nitrocellulose membranes (Bio-Rad). The membranes were immunoblotted with specific primary antibodies, horseradish peroxidase-conjugated secondary antibodies, and visualized by SuperSignal West Pico Stable Peroxide Solution (Thermo Fisher Scientific). The primary antibodies included: AR (dilution 1:1000, #sc-816, Santa Cruz Biotechnology), CXXC5 (dilution 1:1000; #16513-1-AP, Proteintech), TET2 (dilution 1:1000; #MABE462, Millipore), TET3 (dilution 1:1000; ab139311, Abcam), TET1 (dilution 1:1000; #ab191698, Abcam), ID3 (dilution 1:500, #sc-56712, Santa Cruz Biotechnology), PFN2 (dilution 1:1000; #sc-100955, Santa Cruz Biotechnology), BRD4 (dilution 1:1000; #ab128874, Abcam), p300 (dilution 1:1000; #MS-586-PO, Thermo Scientific) and ERK2 (dilution 1:2000; #sc-1647, Santa Cruz Biotechnology).

Immunoprecipitation, and Protein Purification and Pulldown Assay

For the His-tag pulldown assay, purified His-tagged CXXC5 or His-tag lysis control were incubated with the Flag-AR or the V5-TET2 alone or with both Flag-AR and V5-TET2 in binding buffer containing 10 mM imidazole for 4 hours at 4° C. Ni-NTA beads (Qiagen) were added to the solutions, incubated for 3 hours at 4° C., washed with washing buffer containing 10 mM imidazole, and eluted with SDS sample buffer.

Statistical Analysis

GraphPad Prism 7 was used for statistical analyses with the qPCR, cell proliferation analysis, tumor growth analysis, and IHC quantification data. P-values from unpaired two-tailed Student's t tests were used for comparisons between two groups. One-way ANOVA with Bonferroni's post hoc test was used for multiple comparisons. Two-way ANOVA followed by post hoc test was applied to analysis involving both treatment and time course. P value<0.05 was considered significant.

Results

Genome-Wide Profiling of AR Chromatin Binding in ENZ-Resistant ARPC Cells

Figure 1B:
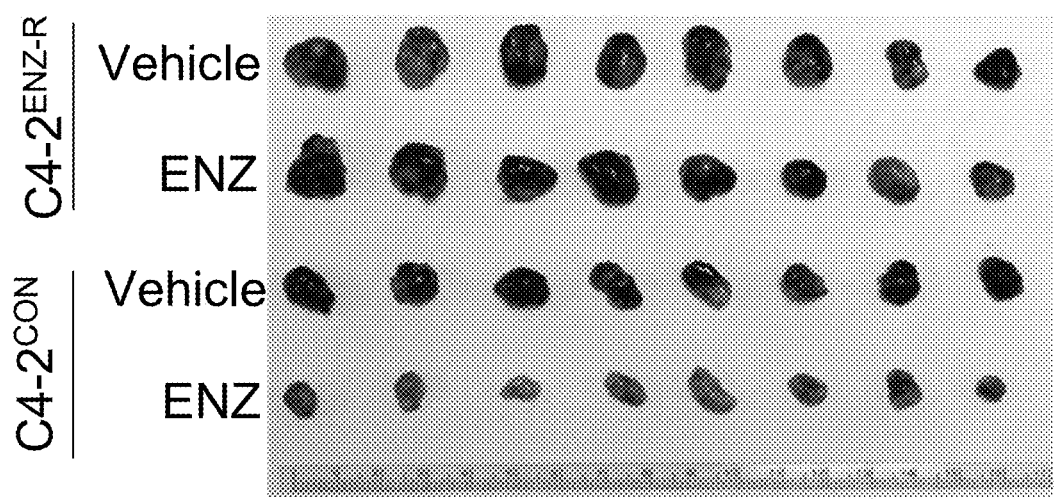
Figure 1C:
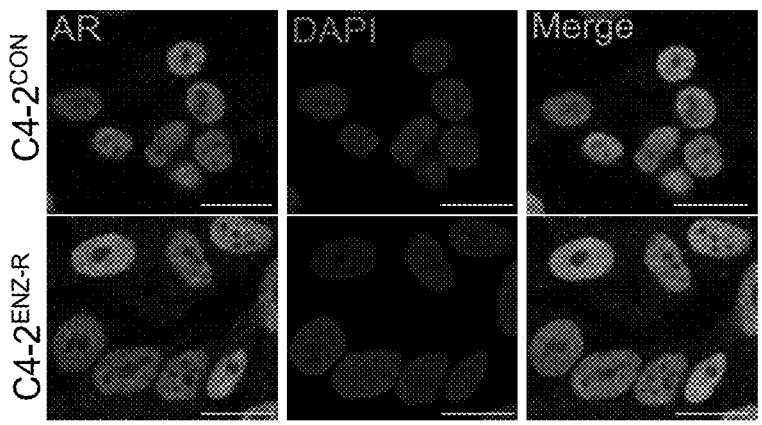
Figure 1D:
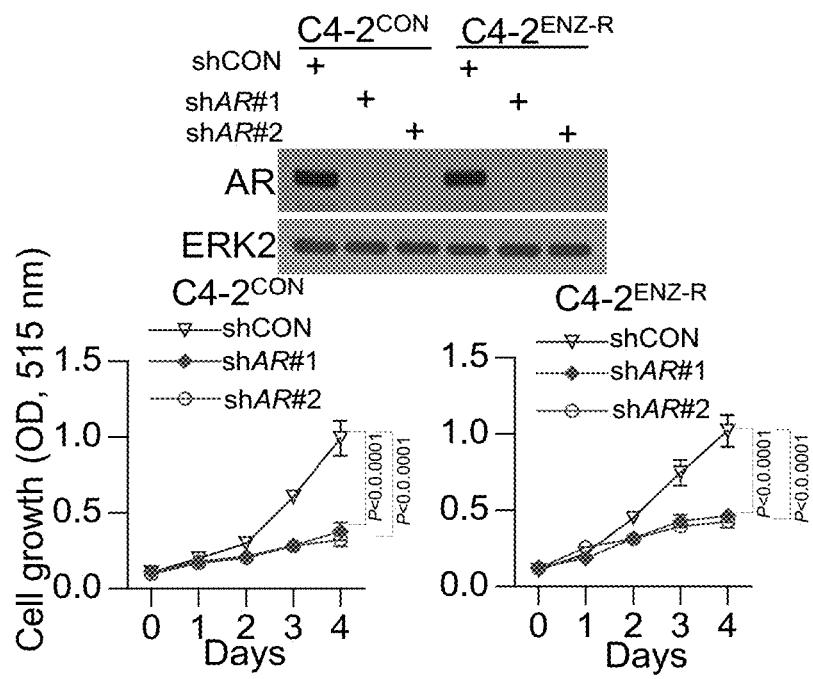
Figure 7A:
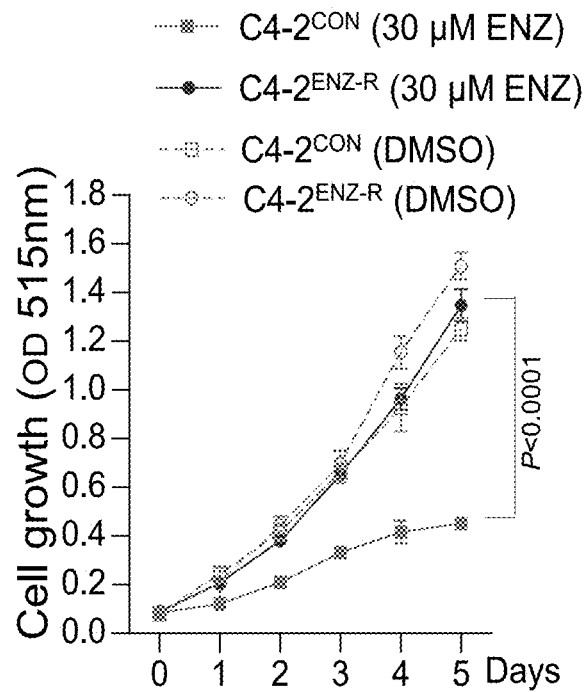
FIGS. 7A-7E. Full-length AR, but not AR variants, drives ENZ-resistant cell proliferation. A: C4-2CON and C4-2ENZ-R cells were treated with the indicated concentrations of ENZ, and cell proliferation was measured by SRB assay. Data are represented as means±s.d., n=6. Statistical significance was determined by two-way ANOVA. B: Heatmap showing RNA-seq read intensity of the canonical AR signature genes in C4-2CON and C4-2ENZ-R cells. C: RT-qPCR showing the mRNA level of KLK3 in C4-2CON and C4-2ENZ-R cells. Data are represented as means±s.d., n=3. Statistical significance was determined by unpaired two-tailed Student's t tests. D: Western blot analysis showing the expression of full-length (FL) AR and AR variants (Vs) in C4-2CON and C4-2ENZ-R cells. ERK2 was used as a loading control. E: UCSC genome browser tracks showing RNA-seq signals of AR and AR variants in C4-2CON and C4-2ENZ-R cells. The RNA-seq signals at AR variant-specific exon show that no obvious expression of AR variants was detected in C4-2CON and C4-2ENZ-R cells.
Figure 7B:
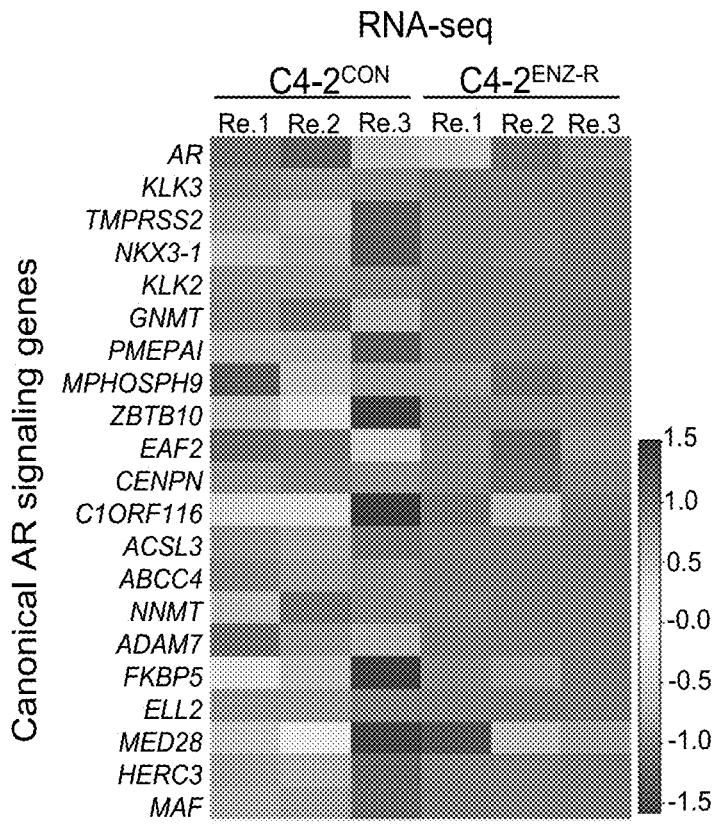
Figure 7C:
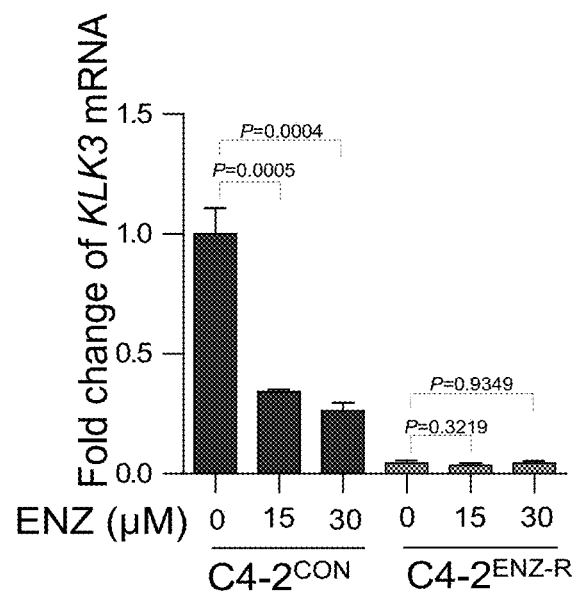
Figure 7D:
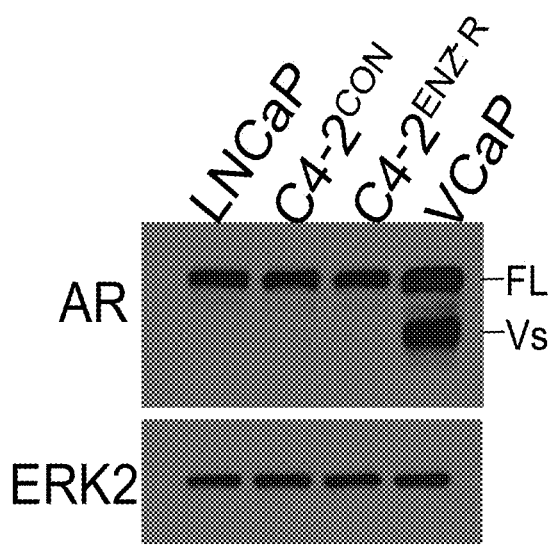
Figure 7E:
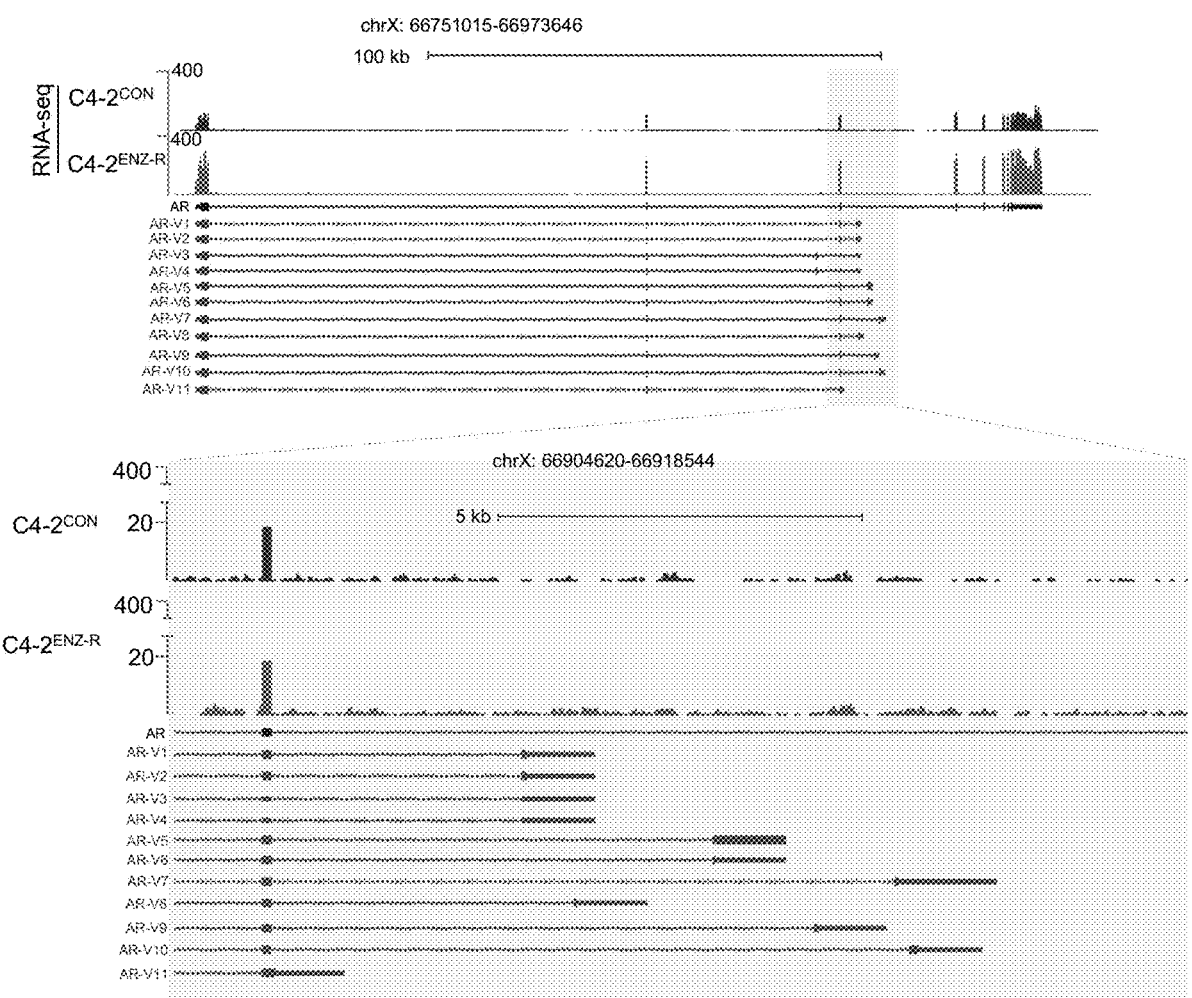
Figure 8D:
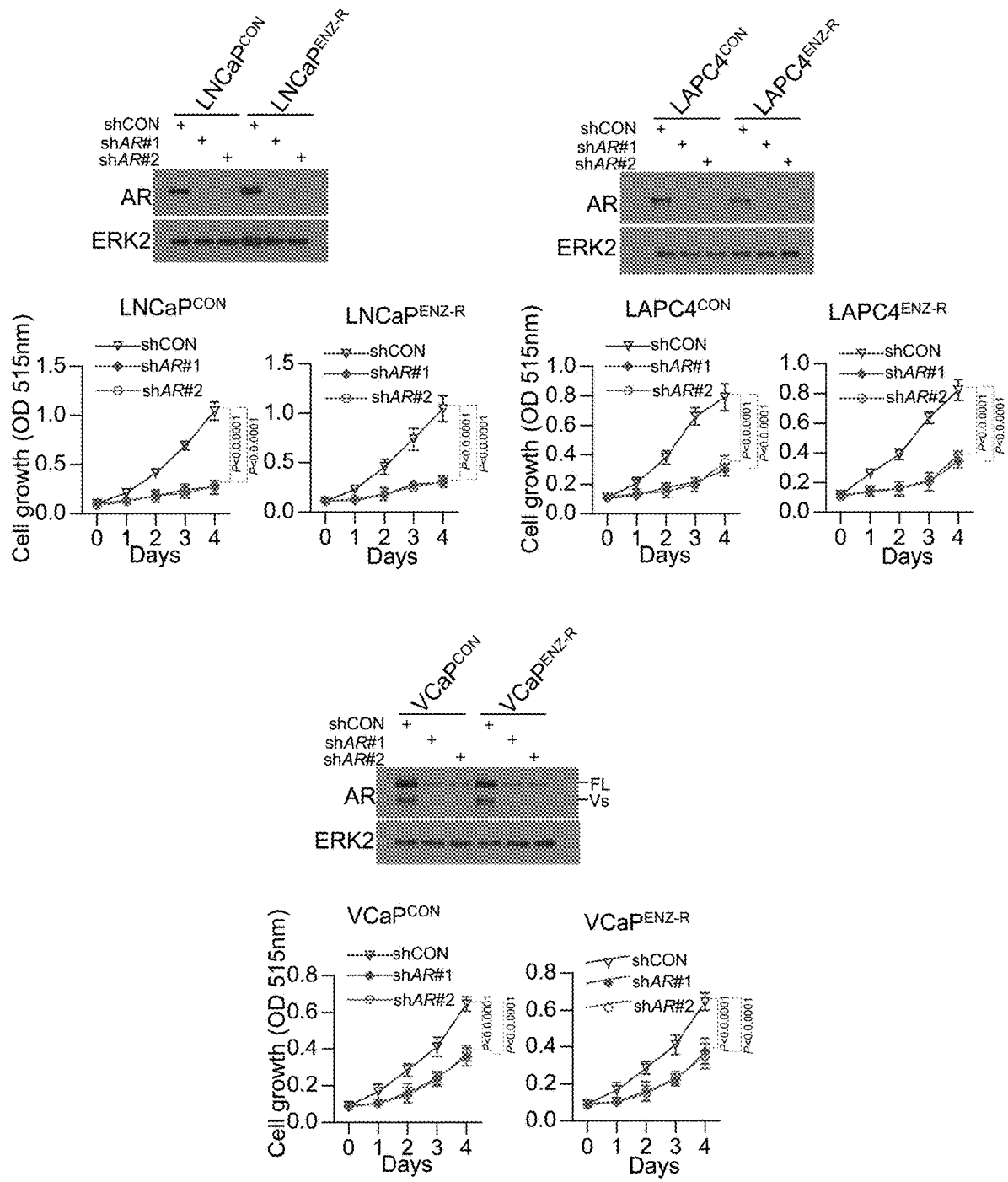

To recapitulate the enzalutamide (ENZ)-resistance seen in the clinic, ENZ-resistant ARPC cell lines were established from C4-2, LNCaP, LAPC4, and VCaP cell lines through long-term (>two months) treatment with ENZ. These ENZ-resistant cell lines (C4-2ENZ-R, LNCaPENZ-R, LAPC4ENZ-R, and VCaPENZ-R) were maintained by continuous treatment of ENZ. Control cell lines (C4-2CON, LNCaPCON, LAPC4CON and VCaPCON) were generated in parallel by treating cells with vehicle only (DMSO). The growth of the C4-2ENZ-R cells demonstrated resistant to ENZ treatment both in vitro and in vivo while expression of canonical AR (cAR) target genes, such as KLK3, were suppressed in ENZ-resistant C4-2 cells (FIGS. 1A, 1B; FIGS. 7A-7C). Little or no expression of ARVs were detectable in ENZ-resistant C4-2 cells (FIGS. 7D, 7E). The level and nuclear localization of full-length AR (ARFL) protein were similar between C4-2ENZ-R and C4-2CON cells (FIG. 1C; FIG. 7D). Most importantly, knockdown of AR inhibited ENZ-resistant C4-2 cell proliferation (FIG. 1D). Similar results were obtained in ENZ-resistant LNCaP, LAPC4 and VCaP cell lines (FIGS. 8A-8D). These findings suggest that ARFL, but not ARVs confer ENZ resistance in these cell lines.

Figure 1E:
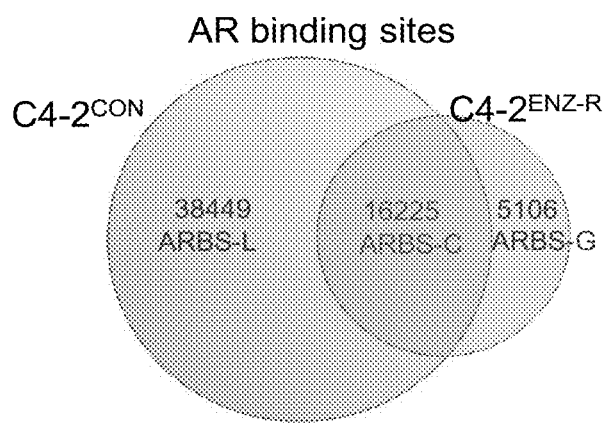
Figure 1F:
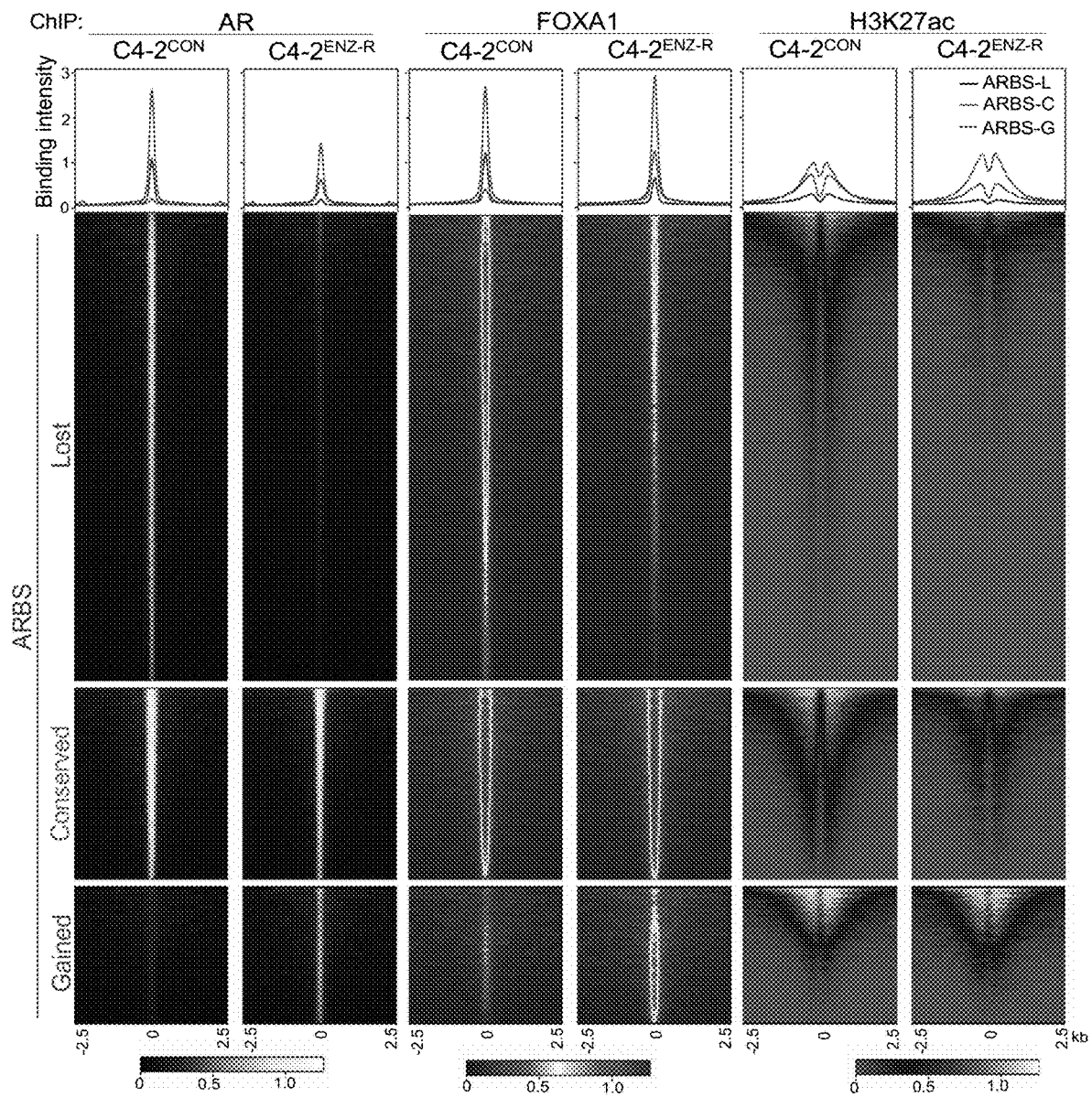
Figure 1G:
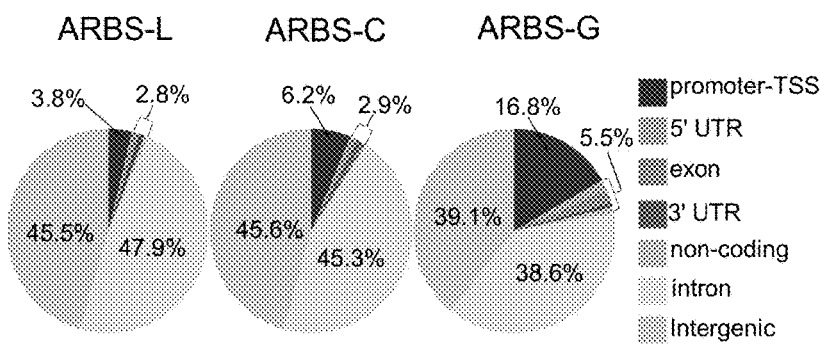

To determine the molecular mechanism underlying ARFL-dependent, but ARV-independent growth of ENZ-resistant cells, chromatin immunoprecipitation sequencing (ChIP-seq) was performed for AR, FOXA1 and histone H3 lysine 27 (H3K27ac) in C4-2ENZ-R and control cells. Among the 59,780 total AR binding sites (ARBS) the majority (approximately 65%) were lost (termed ARBS-L) in C4-2ENZ-R compared to C4-2CON. Approximately 25% of total ARBS remained unchanged (termed ARBS-Conserved or ARBS-C) and approximately 10% gained AR binding (termed ARBS-G) (FIG. 1E-1G). A similar result was observed for FOXA1 binding and H3K27ac enrichment, a histone mark of both active enhancers and transcription start sites (TSS) regions, in C4-2ENZ-R cells (FIG. 1F). Cis-regulatory element annotation system (CEAS) genomic analysis revealed that the rate of AR occupation at promoter-TSS regions was much higher at ARBS-G than that at ARBS-L and ARBS-C (16.8% versus 3.8% and 6.2%, respectively) (FIG. 1G), implying a potential role of ARBS-G in regulating gene transcription and ENZ-resistant growth of C4-2ENZ-R cells.

CXXC5 Regulates AR Binding at ARBS-G Sites Overlapped with CpG Islands

Figure 2B:
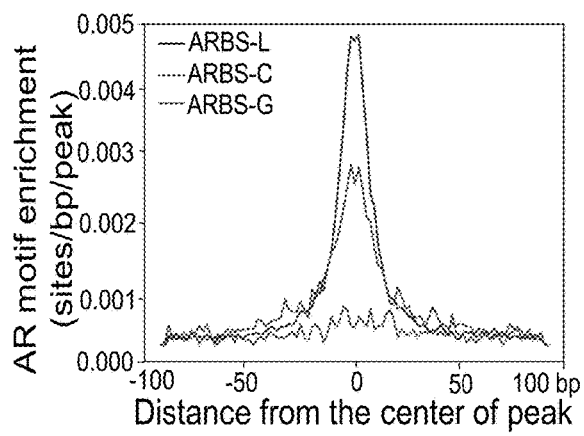
FIGS. 2A-2Q. CXXC5 regulation of AR binding at ARBS-G sites overlapped with CpG islands. A: Analysis of the enrichment of AR and FOXA1 DNA binding motif at ARBS-L, ARBS-C, and ARBS-G sites in ENZ-resistant PCa cells. B: A GC-rich motif (SEQ ID NO:1) identified from de novo DNA binding motif analysis using the STEME method. C: Enrichment of the GC-rich motif at ARBS-L, ARBS-C, and ARBS-G sites in ENZ-resistant PCa cells. D: Percentage of ARBS-L, ARBS-C, and ARBS-G sites overlapped with CpG islands. E: CEAS genomic analysis of ARBS-Gi in C4-2ENZ-R cells. F: Heatmap showing RNA-seq read intensity of CXXC domain-containing genes in C4-2CON and C4-2ENZ-R cells. G: UCSC Genome Browser tracks showing RNA-seq signal profiles of CXXC4 and CXXC5 gene expression in C4-2CON and C4-2ENZ-R cells. H-I: Western blotting showing the level of AR, CXXC5, CXXC4, and TET2 protein in the indicated cell lines. ERK2 was used as a loading control. J: Percentage of ARBS-Gi sites overlapped with AD-ORs and AI-ORs in C4-2B cells reported previously. K: In vitro protein binding assay using V5-tagged TET2 purified from sf9 insect cells and His-tagged CXXC5 and Flag-tagged AR purified from *E. coli*. L: Co-IP showing the interaction of endogenous AR with CXXC5, TET1, TET2, and TET3 in C4-2CON and C4-2ENZ-R cells. M-N: Heatmaps showing ChIP-seq read intensity of CXXC5 and TET2 at ARBS-Gi sites in C4-2CON and C4-2ENZ-R cells. O: Heatmaps showing ChIP-seq read intensity of AR at ARBS-gi in control, CXXC5-knockdown and TET2-knockdown C4-2ENZ-R cells. P-Q: Proliferation and western blot analysis in CXXC5 or TET2 knocking down C4-2CON and C4-2ENZ-R cells. Data are represented as means±s.d. n=6.
Figure 2B:
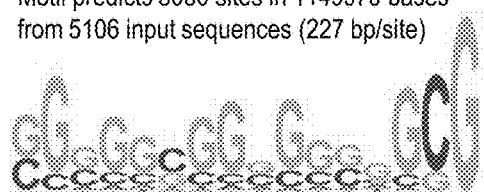
Figure 2A:
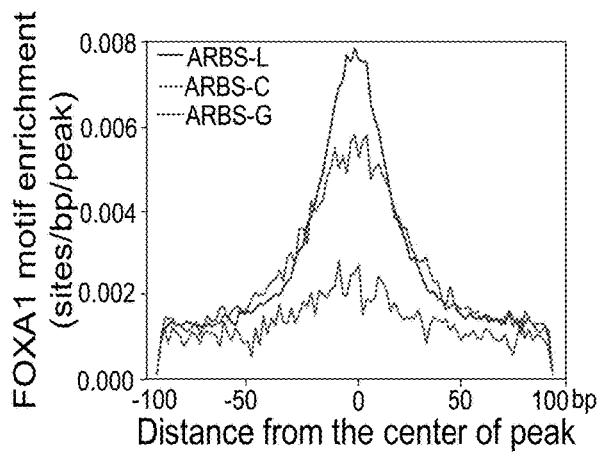
Figure 2C:
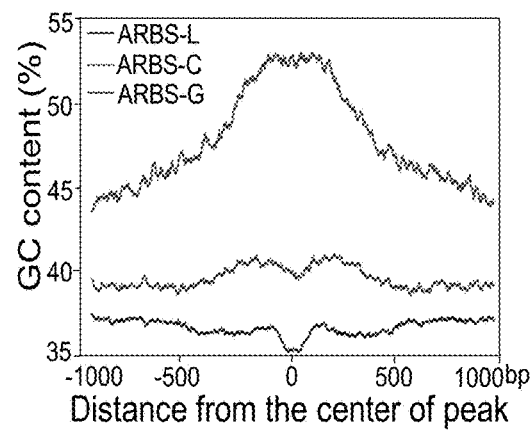

Transcription factor (TF) DNA binding motif analysis revealed that AR and FOXA1 binding motifs were highly enriched at both ARBS-L and ARBS-C, but not at ARBS-G (FIG. 2A), stressing that ARBS-G are likely mediated through ARE-independent and/or FOX element-independent mechanisms. STEME-based motif enrichment analysis failed to identify any conserved TF DNA binding motifs except a GpG/CpG-rich motif at ARBS-G (FIG. 2B). This phenomenon seemed specific for ARBS-G since enrichment of this motif was much higher at ARBS-G compared to ARBS-L and ARBS-C (FIG. 2C). Approximately 20% of ARBS-G sites (approximately 1,000) overlapped with CpG islands (CpGi, ~1-2 kb GC-rich regions). The overlapping sites were termed ARBS-Gi. Notably, ARBS-G overlapped with CpGi more frequently than ARBS-L and ARBS-C (FIG. 2D). More than 70% of ARBS-Gi were located at the promoter-TSS region (FIG. 2E), supporting a potential role of ARBS-Gi in regulation of gene transcription in ENZ-resistant cells.

Figure 2G:
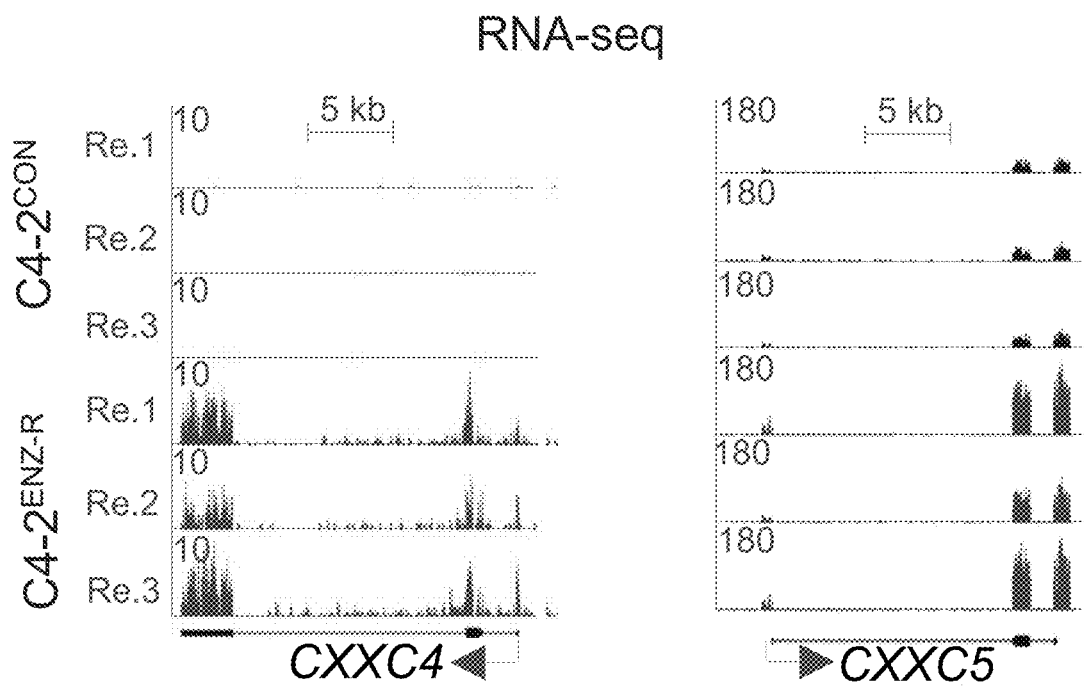
Figure 2H:
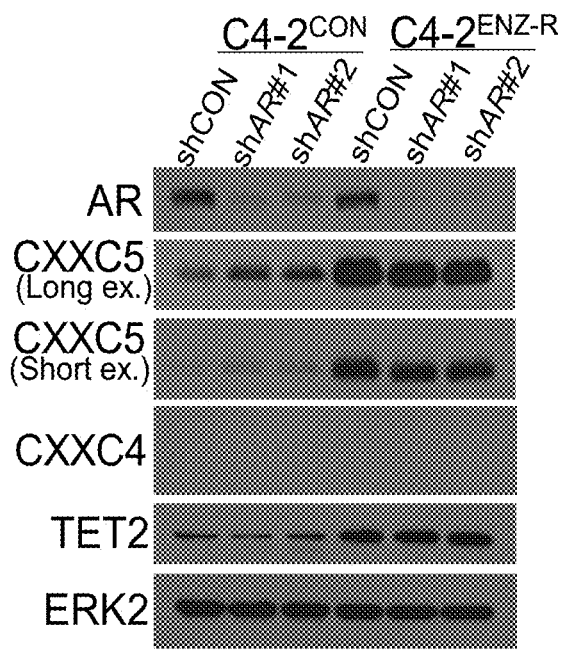
Figure 2I:
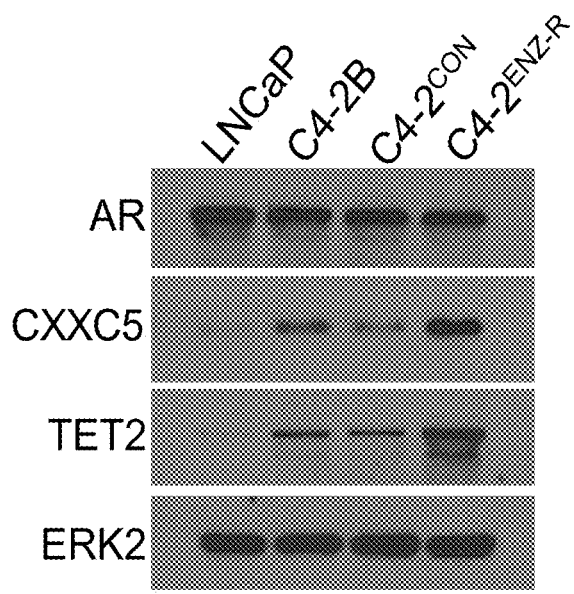
Figure 2J:
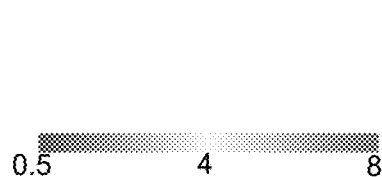
Figure 2J:
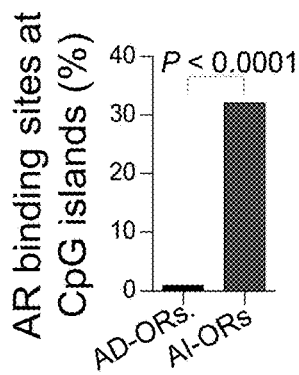
Figure 9A:
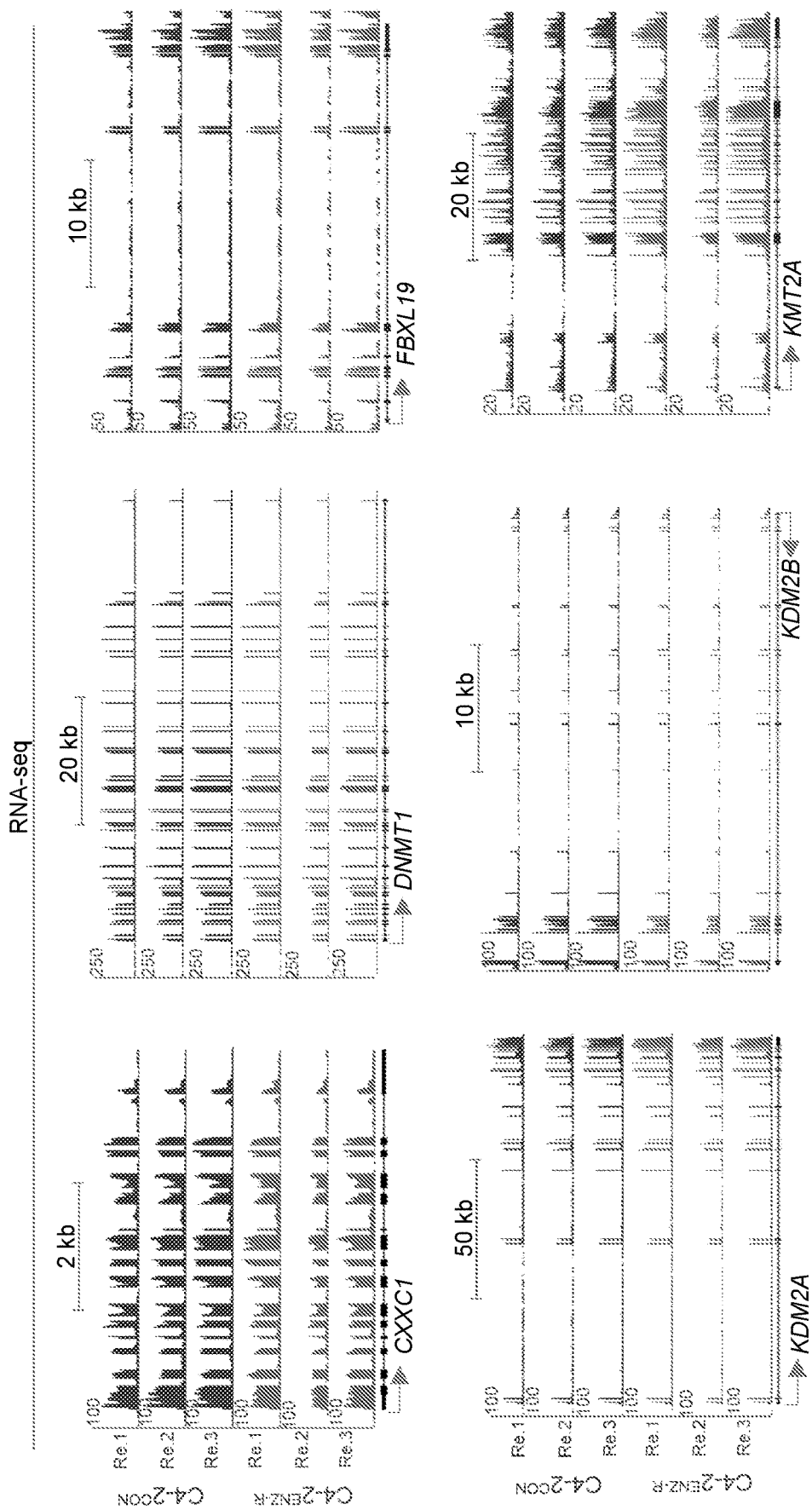
FIGS. 9A-9C. Expression of CXXC domain related genes revealed by RNA-seq data in C4-2CON and C4-2ENZ-R cells. A: UCSC genome browser tracks showing RNA-seq signals of 10 CXXC domain genes (KDM2A, KDM2B, FBXL19, CXXC1, DNMT1, KMT2A, KMT2D, MBD1, TET1, and TET3) in C4-2CON and C4-2ENZ-R cells. B: Western blot analysis showing the expression of CXXC4 protein in C4-2CON and C4-2ENZ-R cells. The lysate of 293T cells transfected with CXXC4 plasmid was used as positive control. ERK2 was used as a loading control. C: UCSC genome browser tracks showing RNA-seq signals of TET2 in C4-2CON and C4-2ENZ-R cells.
Figure 9A:
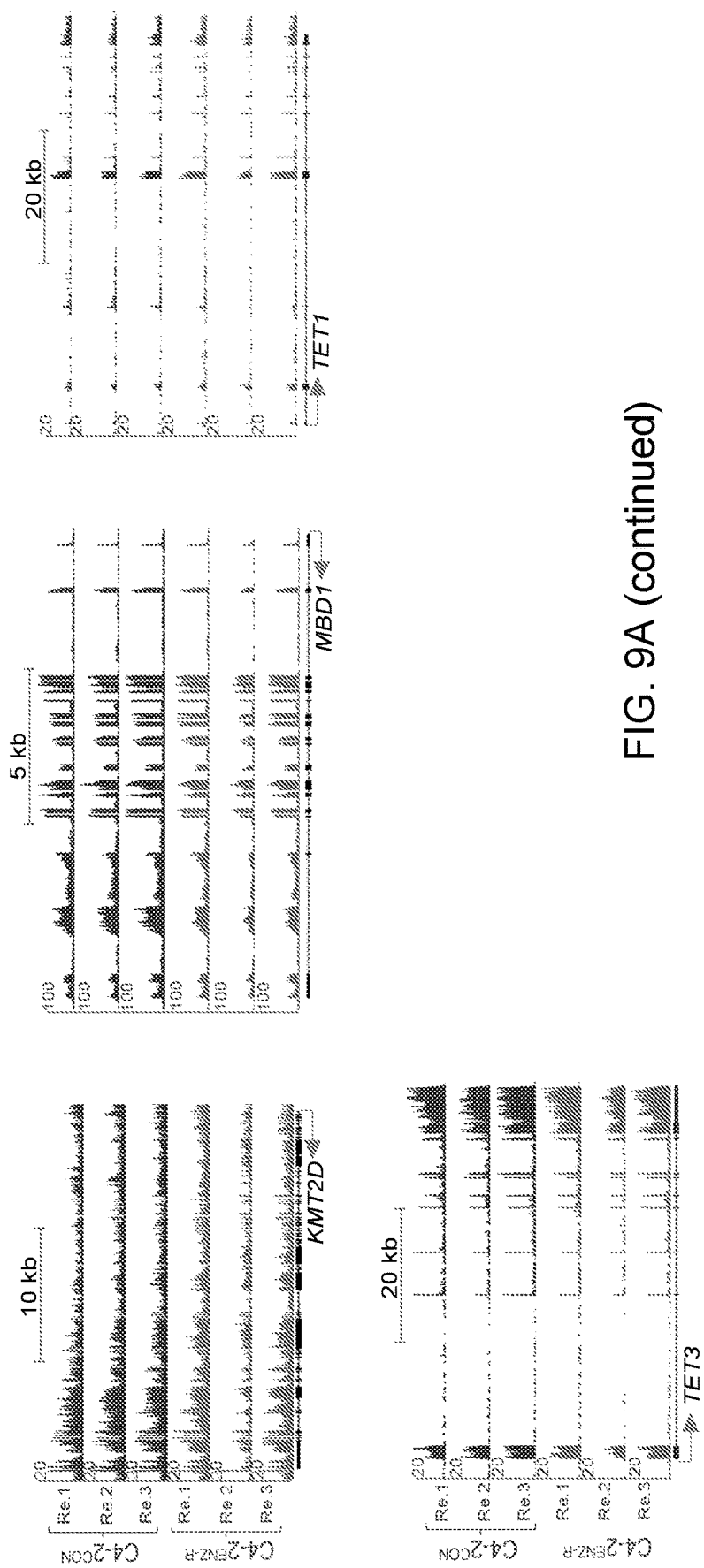
Figure 9B:
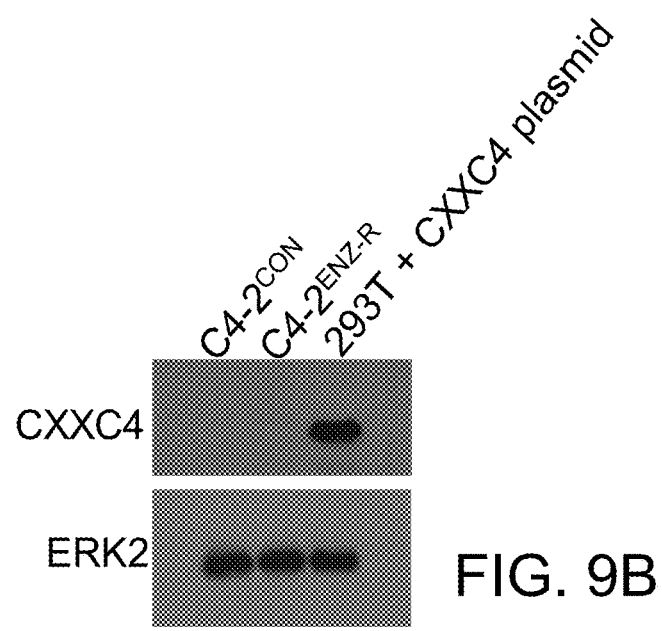
Figure 9C:
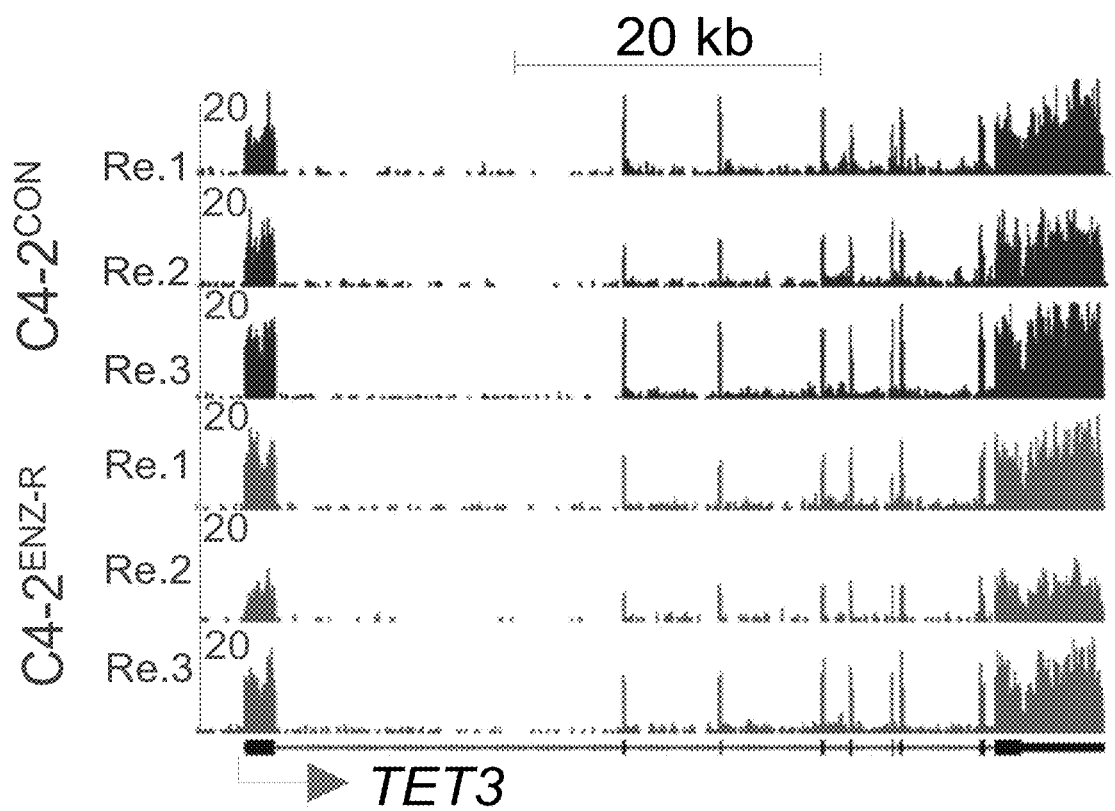

CXXC domain-containing proteins selectively recognize unmodified CpG DNA (22,23 Ref). There are 12 CXXC-domain proteins in the human genome. RNA sequencing (RNA-seq) analysis revealed that of all the CXXC-domain genes, only CXXC4 and CXXC5 mRNA were drastically upregulated in ENZ-resistant cells (FIG. 2F, 2G; FIG. 9A). Similarly, western blot analysis showed that CXXC5 protein was upregulated in C4-2ENZ-R where CXXC4 protein was expressed at lower levels in both C4-2ENZ-R and C4-2CON cells (FIG. 2H; FIG. 9B). CXXC5 expression was upregulated due to AR knockdown in C4-2CON cells, suggesting that CXXC5 might be an AR repression target in ENZ-sensitive ARPC cells although this was not the case in ENZ-resistant cells (FIG. 2H). Similar to the scenario in ENZ-resistant cells, CXXC5 level was also much higher in the metastatic CRPC (mCRPC) cell line C4-2B compared to hormone-naïve LNCaP cells (FIG. 2I). Meta-analysis of a previous report (Decker et al., *Nucleic Acids Res.*, 40:10765-10779 (2012)) revealed that the ARBS-Gi identified in ENZ-resistant cells significantly overlapped more with the androgen-independent occupied regions (AI-ORs) of AR than androgen-dependent occupied regions (AD-ORs) in C4-2B cells (FIG. 2J).

Figure 2L:
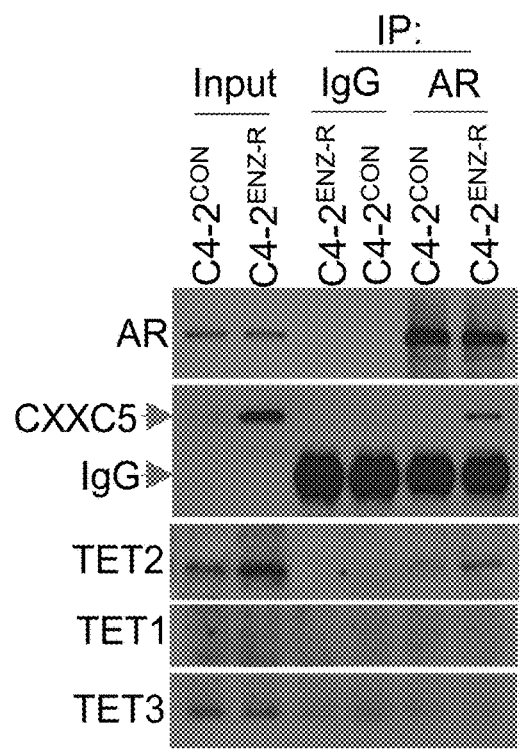
Figure 2K:
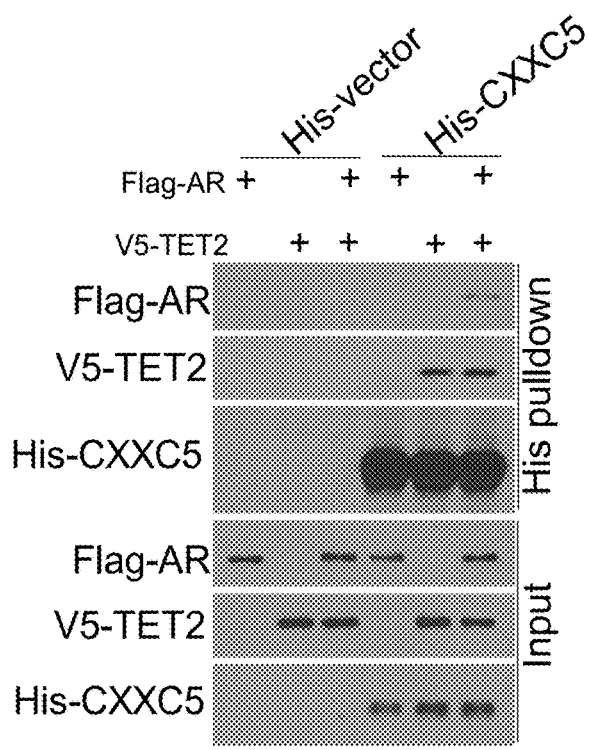
Figure 2K:
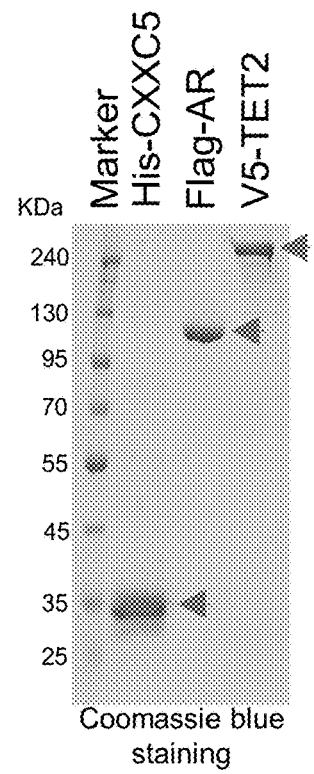
Figure 3A:
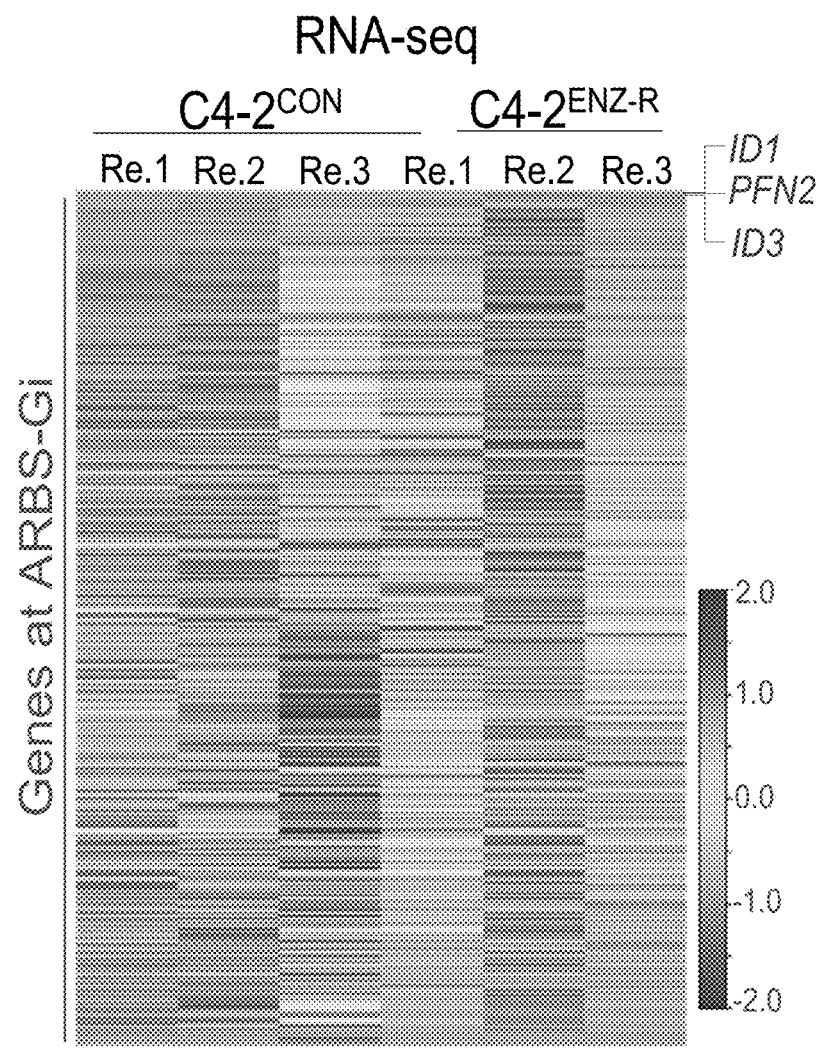
FIGS. 3A-3E. Upregulation of genes located at ARBS-Gi in ENZ-resistant ARPC cells. A: Heatmap showing RNA-seq read intensity of the genes located at ARBS-Gi in C4-2CON and C4-2ENZ-R cells. B: GSEA signatures of upregulated genes located at ARBS-Gi in ENZ-resistant ARPC cells. C: Gene Ontology (GO) analysis of the top 500 changed genes in C4-2ENZ-R cells. D-E: UCSC Genome Browser tracks showing profiles of RNA-seq signals, ChIP-seq signals of IgG, AR, CXXC5, TET2, FOXA1, and H3K27ac at ARBS-Gi (ID1, PFN2, and ID3) and ARBS-L (KLK3, TMPRSS2, and NKX3.1).
Figure 3B:
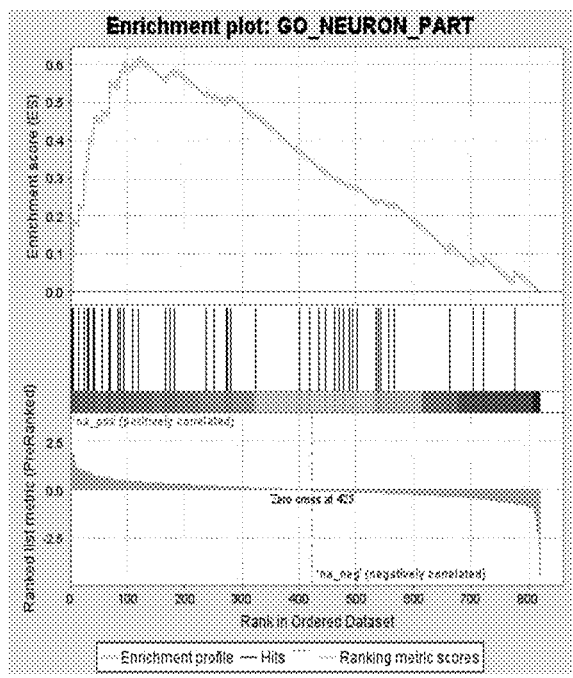
Figure 3B:
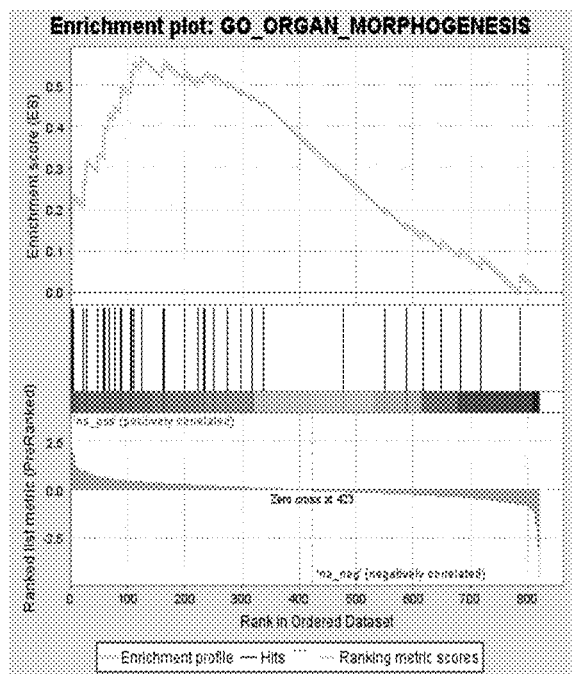
Figure 3C:
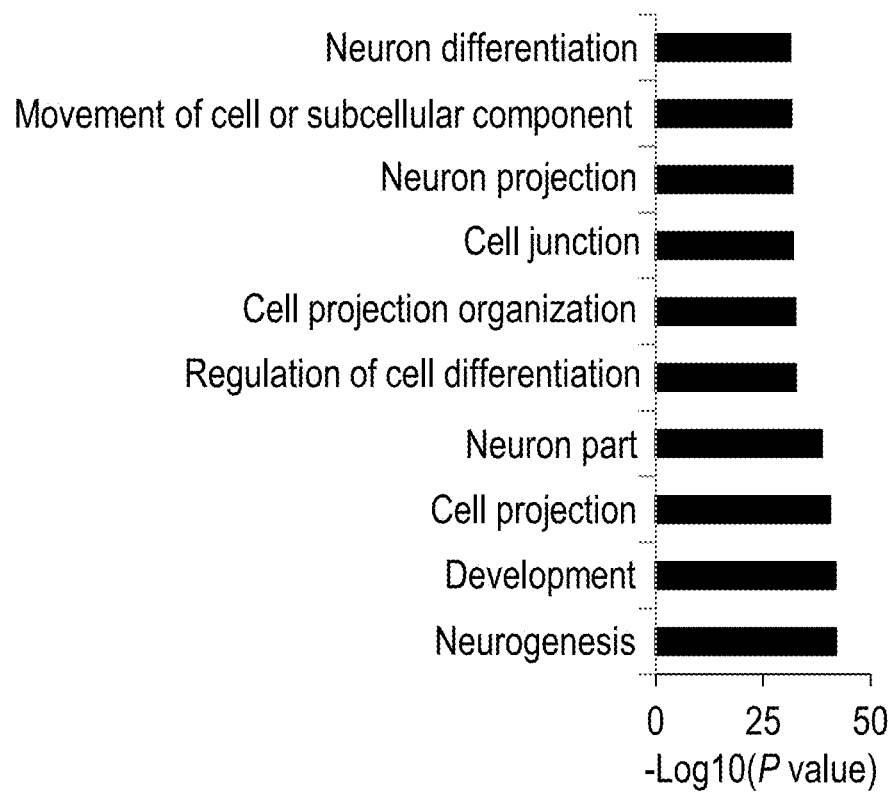

TET2 is the only human methylcytosine dioxygenase that lacks a CXXC domain. In order to facilitate binding to demethylated cytosine-rich DNA, TET2 interacts with CXXC4/5 to form a functional dioxygenase complex, thereby permitting CXXC4/5 binding to the demethylated cytosine-rich DNA (CpN) elements with CpGi. Upregulation of TET2 co-occurred with CXXC5 at both mRNA and protein level although increased expression of TET2 was not affected by AR knockdown in C4-2ENZ-R cells (FIG. 2H; FIG. 3C). In vitro protein pulldown assay showed that CXXC5 physically interacted with TET2, confirming previous findings (Ko et al., *Nature*, 497:122-126 (2013)). However, no CXXC5-AR interaction was detected under similar conditions (FIG. 2K). Intriguingly, CXXC5 bound to AR in the presence of TET2 (FIG. 2K). Co-immunoprecipitation (Co-IP) showed that AR-CXXC5 interaction was detected at the endogenous level and that the interaction occurred only in C4-2ENZ-R, but not C4-2CON cells (FIG. 2L). In contrast, AR bound to TET2 in both cell lines whereas AR had no interaction with TET1 and TET3 in these cell lines (FIG. 2L). These data indicate that increased expression of CXXC5 in ENZ-resistant cells promotes its interaction with AR, which is a process mediated by TET2.

Figures 2M, 2N:
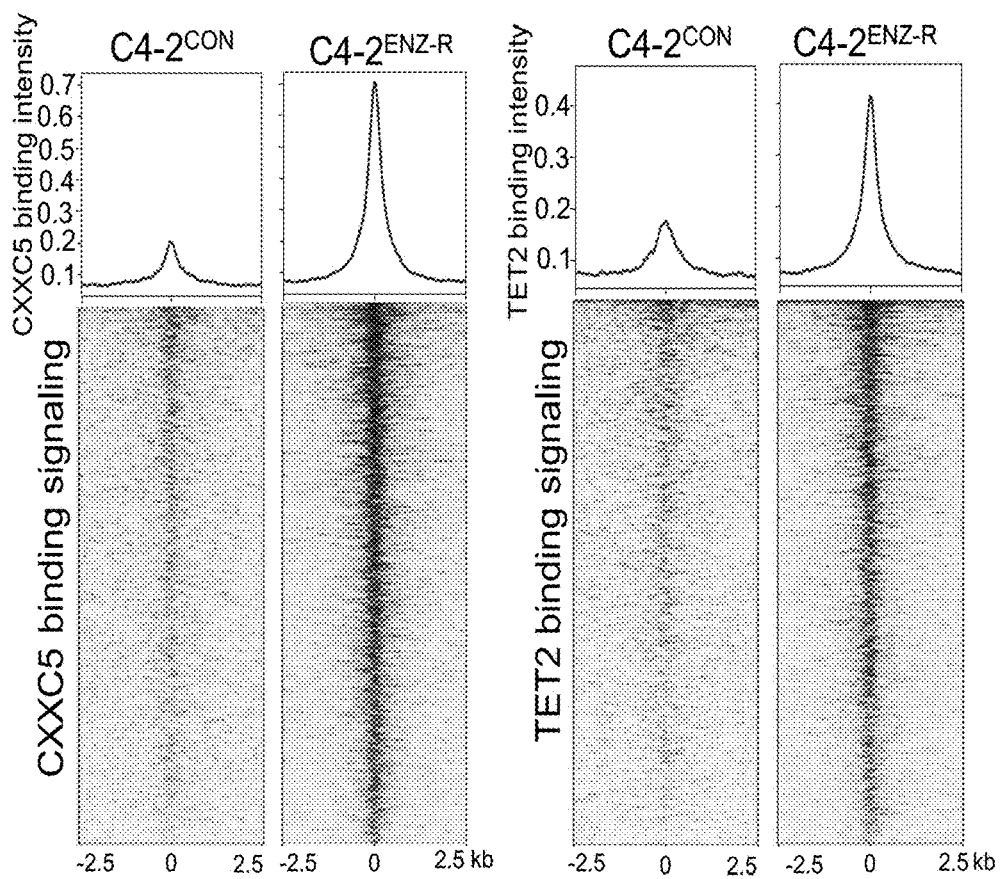
Figure 2O:
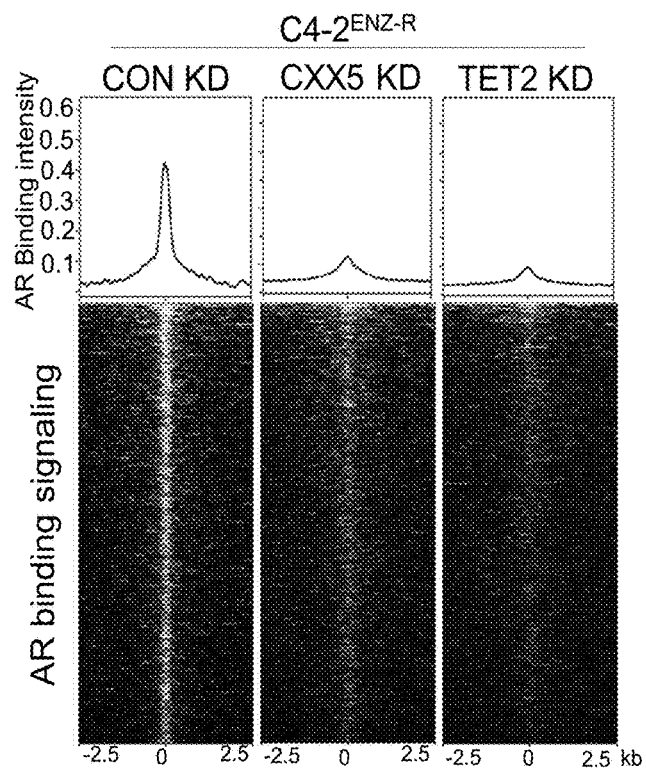
Figure 2P:
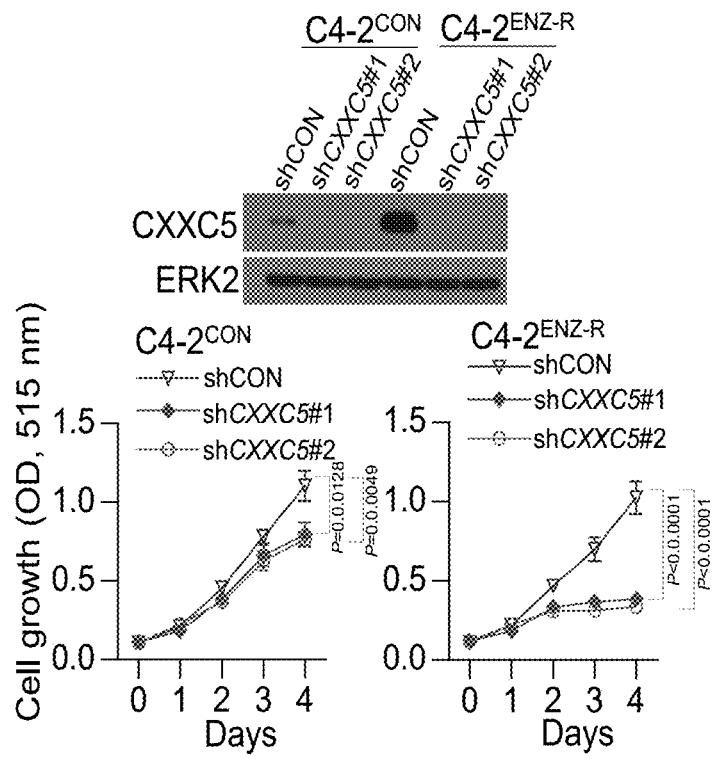
Figure 2Q:
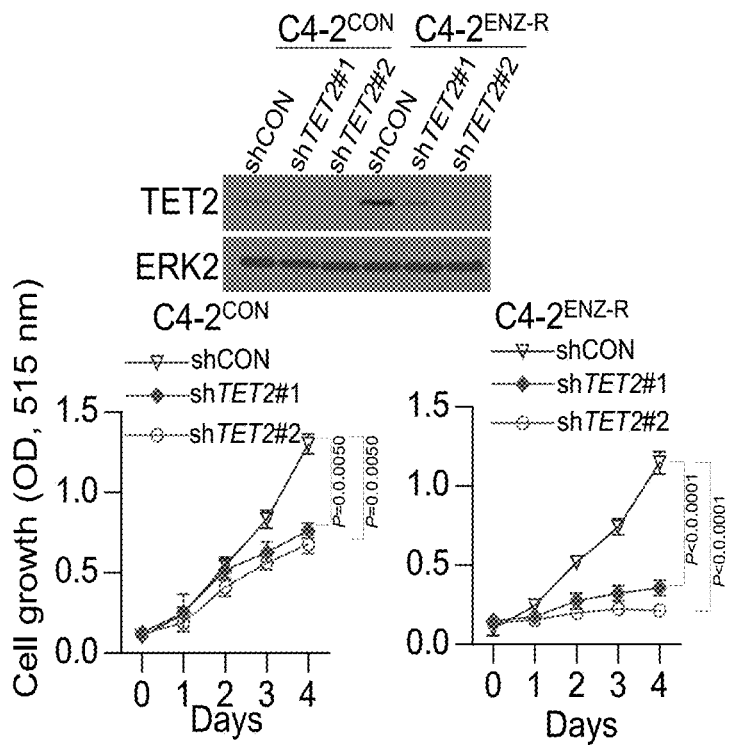

Next, further examination of whether CXXC5 and TET2 played any role in ARE-independent chromatin recruitment of AR in ENZ-resistant cells revealed a causal relationship. Consistent with the co-IP data (FIG. 2L), CXXC5 and TET2 ChIP-seq data showed enrichment of CXXC5 and TET2 at ARBS-Gi was higher in C4-2ENZ-R compared to control cells (FIGS. 2M, 2N). Most importantly, AR binding at ARBS-Gi was impaired by knockdown of either CXXC5 or TET2 in ENZ-resistant cells (FIG. 2O). Similar to the effect of AR knockdown (FIG. 1D), depletion of CXXC5 or TET2 restored the sensitivity of C4-2ENZ-R cells to ENZ (FIGS. 2P, 2Q). These data support a causal relationship between increased expression of CXXC5 and TET2 in ARE-independent chromatin recruitment of AR and ENZ-resistant growth of ARPC cells.

Figure 10A:
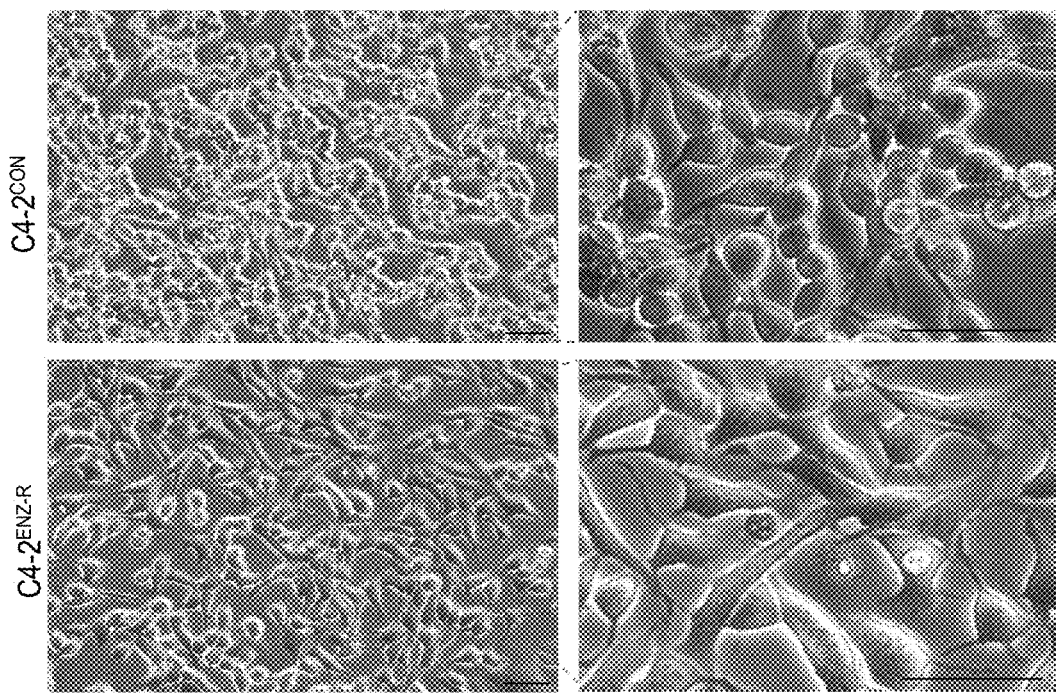
FIG. 10A-10D. Phenotypic characterization of ENZ-resistant C4-2ENZ-R cells. A: Phase contrast image of C4-2CON and C4-2ENZ-R cells cultured in regular or ENZ-supplied media, respectively. Scale bar, 50 µm. B: C4-2CON and C4-2ENZ-R cells were plated in Transwell chambers and treated with 30 µg of ENZ for 24 hours, and the migrated cells were imaged and counted. Scale bar, 50 µm. Data are represented as means±s.d., n=3. Statistical significance was performed by unpaired two-tailed Student's t tests. C-D: UCSC genome browser tracks showing RNA-seq signals of THBS1 (C) and MMP14 (D), two transcriptional target genes of ID1 in C4-2CON and C4-2ENZ-R cells.
Figure 10B:
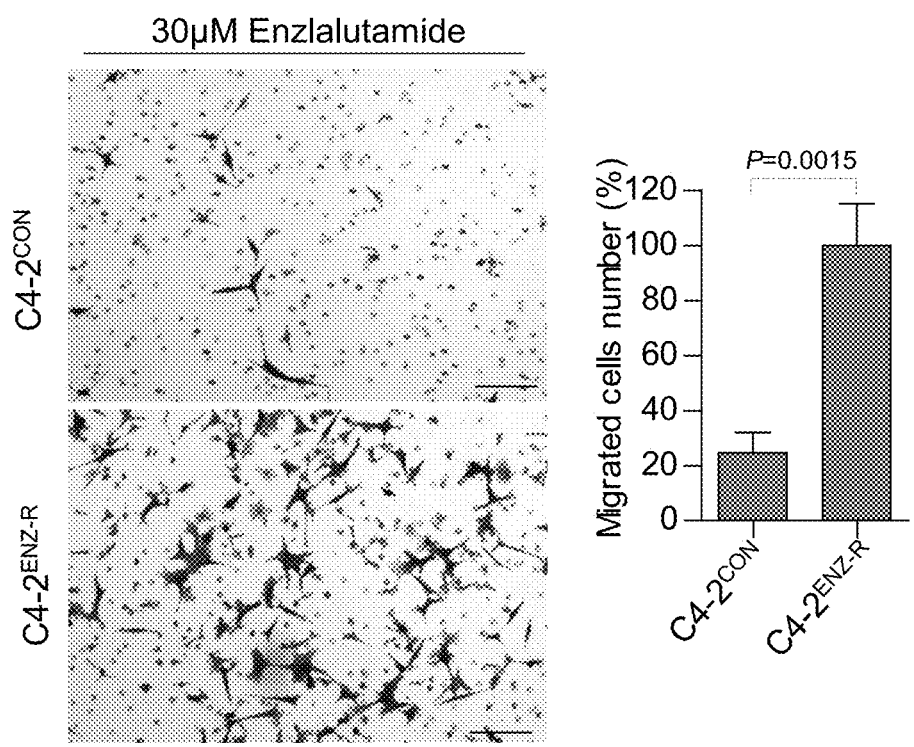

Upregulation of Neuron Differentiation and Cell Mobility Genes Located at ARBS-Gi in ENZ-Resistant ARPC To define the downstream effectors of increased AR binding at ARBS-Gi in ENZ-resistant cells, expression of genes associated with ARBS-Gi loci in C4-2ENZ-R and control cells were compared by RNA-seq. Of note, RNA-seq data from one replicate of the C4-2ENZ-R cells was excluded from further analysis due to its poor correlation with the other two biological replicates. The data revealed that >50% of ARBS-Gi genes were significantly upregulated in C4-2ENZ-R cells compared to control cells (FIG. 3A). Gene set enrichment analysis (GSEA) showed that 'neuron projection' and 'organ morphogenesis' genes were among the most significantly upregulated targets (FIG. 3B). Gene ontology biological process (GO-BP) analysis of the top 500 differential expression genes in ENZ-resistant cells showed the enrichment of genes involved in 'cell motion', 'neuron differentiation' and 'cell proliferation' (FIG. 3C). These results were consistent with the neuron-like morphology and accented migration ability of C4-2ENZ-R cells (FIG. 10A, 10B).

Figure 3D:
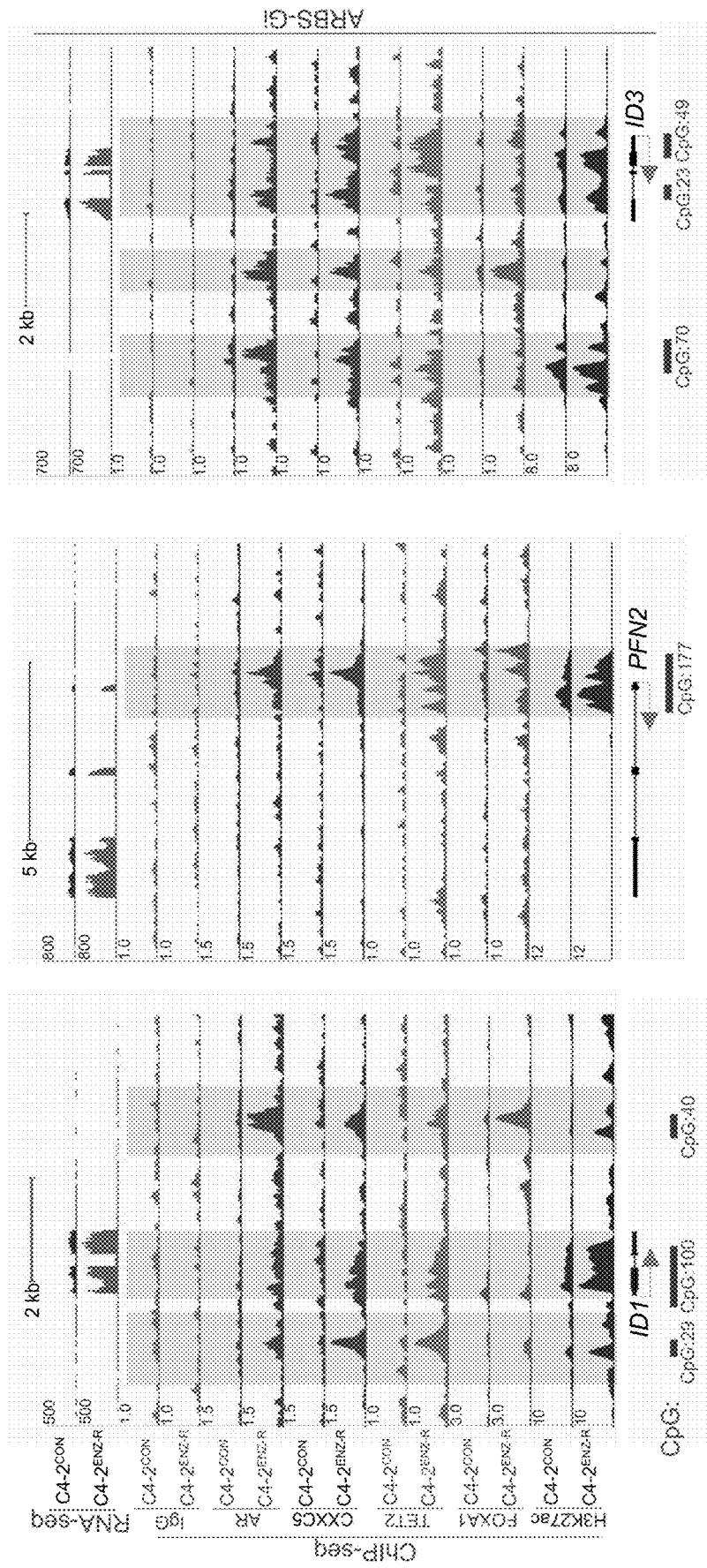
Figure 3E:
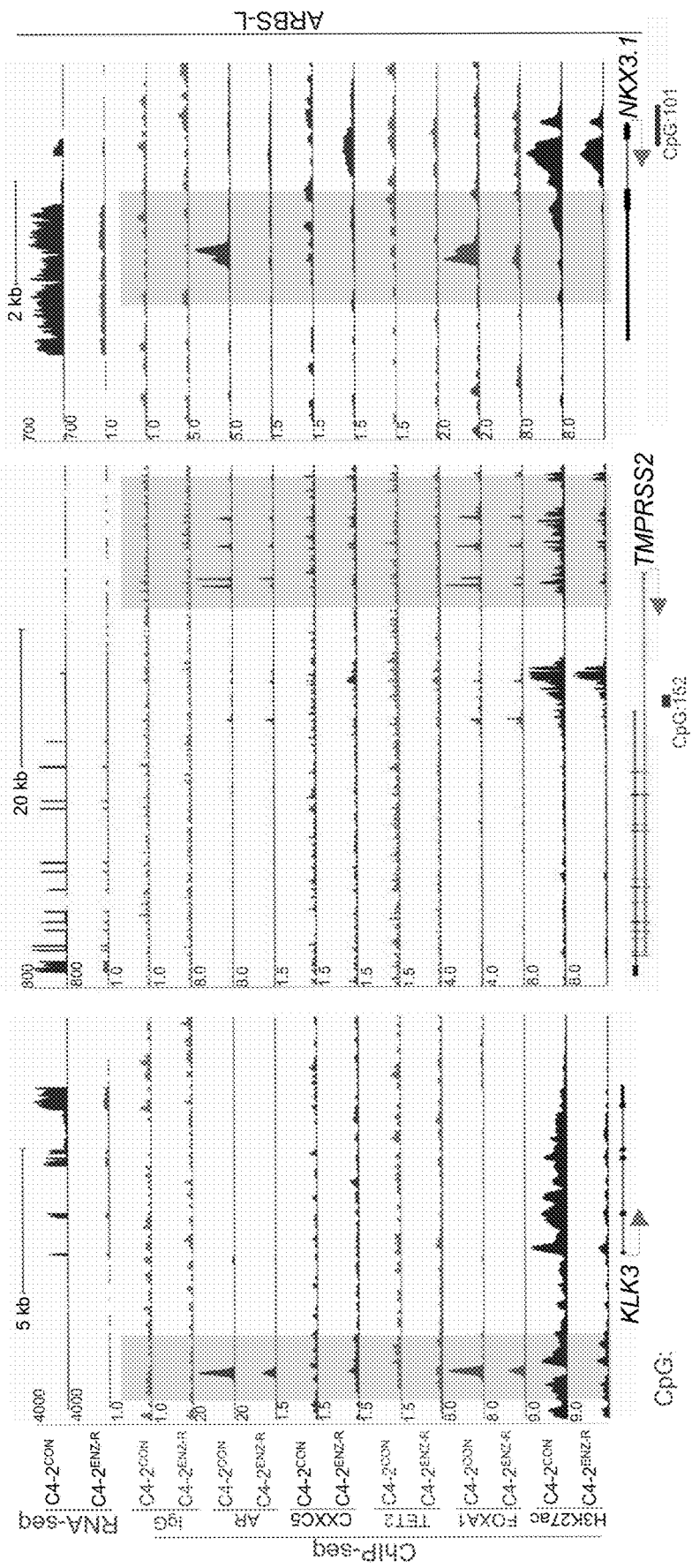
Figure 10C:
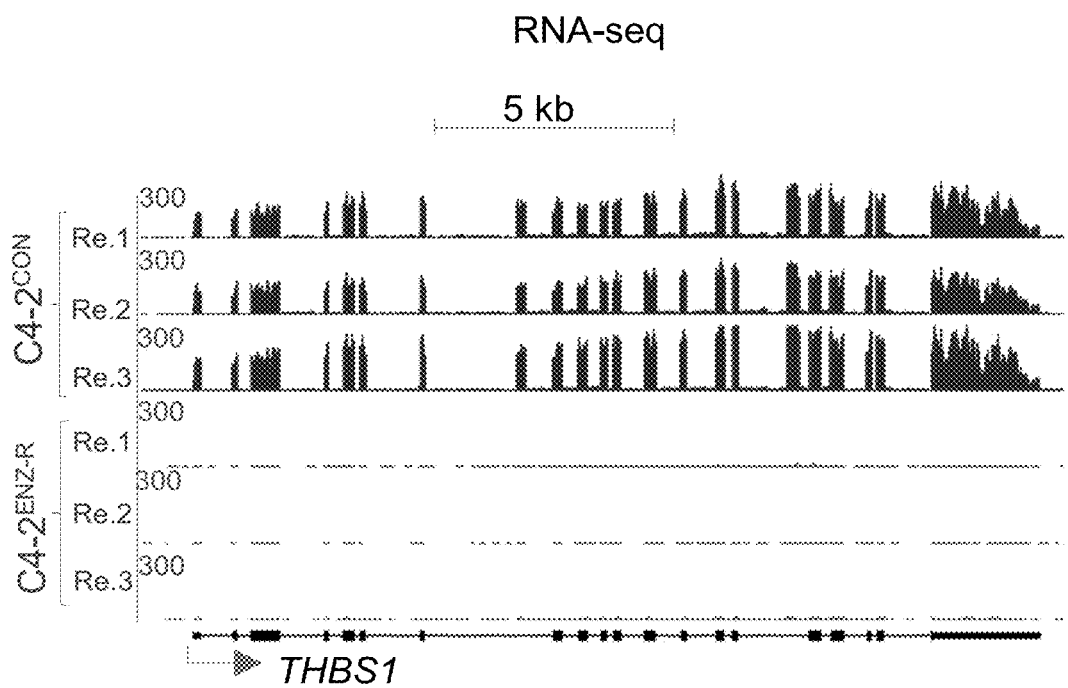
Figure 10D:
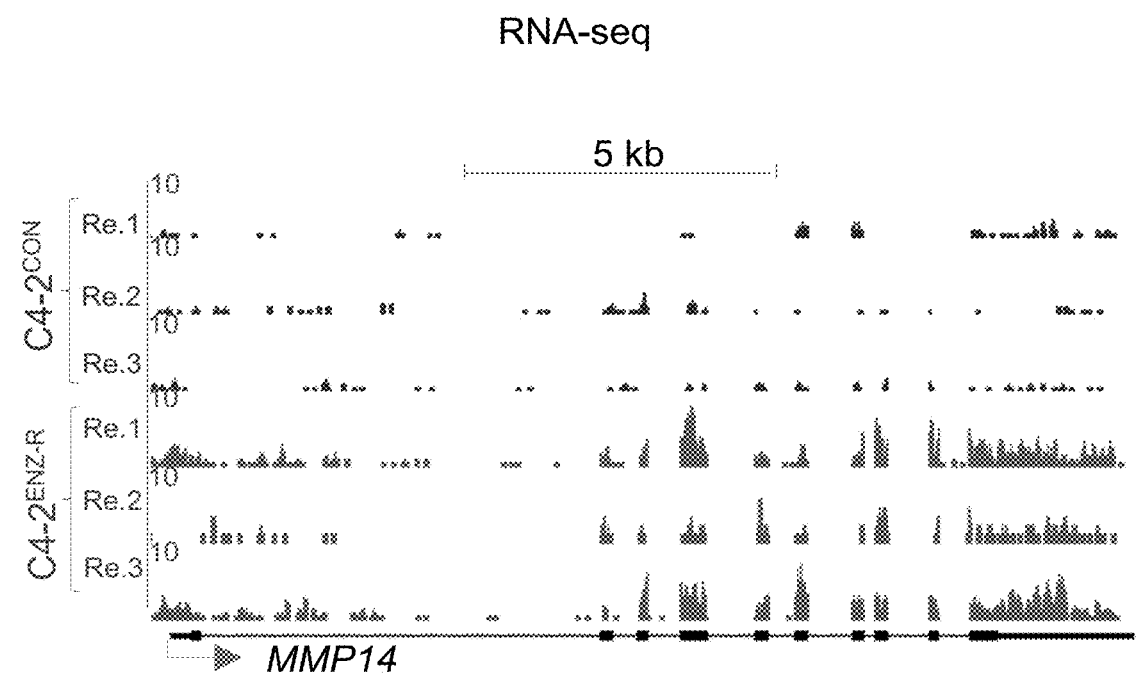

Among the top upregulated genes associated with ARBS-Gi loci were genes highly relevant to regulation of neuronal lineage and tumor progression, including inhibitor of differentiation 1 (ID1), inhibitor of differentiation 3 (ID3), and the actin cytoskeletal regulator PFN2 (FIG. 3A and Table 2). RNA-seq data showed that ID1, ID3, and PFN2 genes were overexpressed in ENZ-resistant cells (FIG. 3D). AR, CXXC5, TET2, and FOXA1 binding were markedly increased at the promoters and/or potential enhancers of ID1, ID3, and PFN2 genes in C4-2ENZ-R cells, although FOXA1 signal was not always increased (FIG. 3D). Consistent with active transcription at ID1, ID3, and PFN2 gene loci in C4-2ENZ-R cells, the signal intensity of H3K27ac was augmented at these loci (FIG. 3D). In agreement with the upregulation of ID1, expression of its key downstream target genes such as THBS1 and MMP14 were also upregulated in C4-2ENZ-R cells (FIGS. 10C, 10D). In contrast, the canonical AR garget genes such as KLK3, TMPRSS2, and NKX3.1 were downregulated in C4-2ENZ-R cells (FIG. 3E). The enrichment of AR, FOXA1, and H3K27ac at the promoters and/or enhancers of these gene loci was also decreased in C4-2ENZ-R cells (FIG. 3E). However, no obvious CXXC5 and TET2 binding peaks were detected at these gene loci (FIG. 3E). These data suggest that at the ENZ-resistant stage AR function is switched from its regulation of expression of canonical targets to regulation of unorthodox genes (e.g., non-canonical targets (ncAR)). Genes that are tightly associated with aggressive phenotypes including neuronal lineage and cell migration.

TABLE 2

| Gene name | Score |
| --- | --- |
| LUZP2 | 3.625449 |
| DYRK3 | 2.106622 |
| ID1 | 2.102616 |
| PFN2 | 2.089388 |
| ID3 | 1.874005 |
| NLGN1 | 1.868585 |
| SORL1 | 1.823411 |
| MICU3 | 1.680531 |
| ACSF2 | 1.464948 |
| PCK2 | 1.330327 |
| CHPT1 | 1.258888 |
| GAB1 | 1.211482 |
| ABCC6 | 1.206542 |
| IRF2BP2 | 1.152091 |
| TBC1D32 | 1.148525 |
| TTLL7 | 1.126742 |
| RNF144B | 1.120283 |
| PTPN14 | 1.114758 |
| METTL21B | 1.053779 |
| HIVEP2 | 1.047281 |
| SLC20A2 | 1.036195 |
| CEP112 | 1.010515 |
| KCTD17 | 1.010297 |
| RDH10 | 1.004319 |
| CADPS2 | 0.994417 |
| EPS8 | 0.990489 |
| ZDHHC24 | 0.988029 |
| RASL11A | 0.978714 |
| NFIC | 0.935418 |
| PARP14 | 0.929686 |
| LPHN1 | 0.91201 |
| ZNF333 | 0.907789 |

TABLE 2-continued

| Gene name | Score |
| --- | --- |
| ZNRF1 | 0.906531 |
| SPRED1 | 0.893979 |
| ZNF558 | 0.872837 |
| HNRNPD | 0.858513 |
| CASZ1 | 0.855336 |
| MTSS1L | 0.848151 |
| PRDX1 | 0.807517 |
| RFX3 | 0.803702 |
| AMFR | 0.779047 |
| NIPAL2 | 0.747238 |
| DAGLA | 0.731922 |
| GPRC5C | 0.72959 |
| GGH | 0.728377 |
| SIAE | 0.716347 |
| RABGAP1L | 0.713954 |
| CYP27B1 | 0.702753 |
| CCNG2 | 0.702504 |
| ID2 | 0.700571 |
| FUT8 | 0.697117 |
| SYNE2 | 0.688956 |
| XYLB | 0.686336 |
| JUNB | 0.683624 |
| KIAA0232 | 0.680013 |
| SLC16A9 | 0.677369 |
| ATP2B1 | 0.67003 |
| CTBS | 0.65554 |
| GATA2 | 0.655348 |
| GRHL2 | 0.653718 |
| SNX27 | 0.64782 |
| FTO | 0.647053 |
| EPRS | 0.646306 |
| ERBB2IP | 0.643368 |
| TMEM64 | 0.642739 |
| NHLRC1 | 0.638405 |
| UBA6 | 0.637778 |
| GSK3B | 0.627135 |
| NQO1 | 0.613746 |
| KAZALD1 | 0.609186 |
| K1AA1598 | 0.609158 |
| STC2 | 0.607665 |
| CELSR3 | 0.602783 |
| ACAD8 | 0.575721 |
| K1AA1244 | 0.572747 |
| DNAJC14 | 0.552671 |
| GDAP1 | 0.549684 |
| SETD2 | 0.548816 |
| ZFYVE9 | 0.548389 |
| AVPI1 | 0.54793 |
| CARS | 0.542967 |
| MANSC1 | 0.540545 |
| NCR3LG1 | 0.54002 |
| MGAT4B | 0.533828 |
| ATP13A2 | 0.530507 |
| PTOV1 | 0.52509 |
| DSTYK | 0.518749 |
| NLRX1 | 0.517046 |
| RXRA | 0.513127 |
| ACTR8 | 0.511332 |
| HIPK1 | 0.510288 |
| PDXDC1 | 0.507816 |
| ZNF646 | 0.506138 |
| LLGL2 | 0.501555 |
| APC | 0.500381 |
| KDM5A | 0.499238 |
| DDHD1 | 0.497985 |
| GALNT2 | 0.495926 |
| TMEM214 | 0.495902 |
| PLEKHH3 | 0.47414 |
| HYOU1 | 0.472738 |
| AEBP2 | 0.467547 |
| GPAA1 | 0.465956 |
| COPS7A | 0.459828 |
| VCPIP1 | 0.459237 |
| TANGO6 | 0.45677 |
| LFNG | 0.456576 |
| CHCHD6 | 0.453318 |
| WWOX | 0.453213 |
| KIF1B | 0.451079 |

TABLE 2-continued

| Gene name | Score |
|---|---|
| SAMD4B | 0.450974 |
| TRPC4AP | 0.44965 |
| ANKRD11 | 0.447843 |
| CAMTA2 | 0.447444 |
| XRRA1 | 0.445464 |
| YTHDC1 | 0.445006 |
| TUFM | 0.441943 |
| MSRB2 | 0.441892 |
| TMEM254 | 0.438458 |
| PPP3R1 | 0.436331 |
| KCNK1 | 0.432068 |
| DPY19L3 | 0.427576 |
| DDIT3 | 0.426553 |
| U2SURP | 0.426165 |
| TDRD7 | 0.41766 |
| RAB2A | 0.416815 |
| ZNF438 | 0.412466 |
| PXK | 0.410493 |
| ZNF184 | 0.40918 |
| MAGI1 | 0.405662 |
| XPO7 | 0.399511 |
| RPA1 | 0.398995 |
| VPS13B | 0.398239 |
| K1AA1429 | 0.397313 |
| TMEM116 | 0.394306 |
| AP1G1 | 0.39405 |
| PAQR3 | 0.392345 |
| CUL9 | 0.39063 |
| CAT | 0.386834 |
| ANKIB1 | 0.385665 |
| STT3B | 0.385137 |
| ATRN | 0.382899 |
| HEXIM1 | 0.380253 |
| TEX261 | 0.379665 |
| TUBGCP3 | 0.379588 |
| RNF11 | 0.372824 |
| CLUAP1 | 0.372685 |
| TERF2IP | 0.371962 |
| MTR | 0.371788 |
| NELFA | 0.369559 |
| ZNF546 | 0.368346 |
| MLST8 | 0.364655 |
| FAM160A2 | 0.362919 |
| NCOA6 | 0.359873 |
| SIK2 | 0.358914 |
| TSC22D2 | 0.358814 |
| PCM1 | 0.357973 |
| APEH | 0.357881 |
| CTBP1 | 0.35577 |
| SLC25A24 | 0.353428 |
| DDX41 | 0.351553 |
| RBFOX2 | 0.349033 |
| ARL6 | 0.348447 |
| KARS | 0.347432 |
| TLE1 | 0.342398 |
| KLF3 | 0.341662 |
| ZZEF1 | 0.338883 |
| ATF4 | 0.338761 |
| LRRC8D | 0.337895 |
| KIF2C | 0.336594 |
| SHPRH | 0.333747 |
| TMCO4 | 0.332987 |
| MINA | 0.332548 |
| SLC26A11 | 0.331412 |
| UFL1 | 0.329147 |
| NANP | 0.327656 |
| ZCCHC4 | 0.32515 |
| KIF3C | 0.321155 |
| GRHL1 | 0.320213 |
| CCNY | 0.317838 |
| XPOT | 0.317456 |
| PRDM10 | 0.316237 |
| MPV17L | 0.315921 |
| SIAH2 | 0.315512 |
| GCN1L1 | 0.314765 |
| PEPD | 0.313788 |
| RSBN1 | 0.309704 |
| DHX8 | 0.308294 |
| USP31 | 0.306878 |
| EDC4 | 0.305535 |
| ZC3H11A | 0.304789 |
| KPNA4 | 0.304261 |
| OGFOD3 | 0.302743 |
| ACACA | 0.301299 |
| EFCAB14 | 0.300603 |
| FUT10 | 0.300387 |
| PAK2 | 0.29884 |
| TCEB2 | 0.296547 |
| ITPRIP | 0.295636 |
| DGCR2 | 0.295146 |
| HIBCH | 0.294401 |
| CAMSAP3 | 0.291788 |
| PDP1 | 0.291196 |
| ATXN2 | 0.290556 |
| PARP1 | 0.288109 |
| K1AA0922 | 0.28698 |
| ARHGAP29 | 0.286774 |
| CHTF18 | 0.285681 |
| CTR9 | 0.282344 |
| PYROXD1 | 0.279741 |
| EFS | 0.278342 |
| PTMS | 0.275216 |
| PANK3 | 0.27521 |
| IKBKB | 0.274547 |
| FAM72A | 0.273929 |
| TGOLN2 | 0.267369 |
| UCKL1 | 0.267315 |
| RB1 | 0.267116 |
| MICAL3 | 0.266404 |
| EEF2 | 0.261903 |
| CEP128 | 0.261892 |
| FNDC3A | 0.259178 |
| CAPN15 | 0.258087 |
| ENTPD4 | 0.256768 |
| NOTCH2 | 0.254027 |
| PHF13 | 0.248563 |
| TBC1D9B | 0.247957 |
| TMEM54 | 0.245964 |
| SON | 0.239735 |
| SNAPC3 | 0.239452 |
| NUTF2 | 0.239262 |
| THYN1 | 0.238992 |
| ING2 | 0.237487 |
| DSP | 0.237095 |
| MAP3K1 | 0.236522 |
| PRKCI | 0.234947 |
| SLC35B3 | 0.23363 |
| ATG3 | 0.232103 |
| STAT1 | 0.232072 |
| WDR34 | 0.231597 |
| AHCYL1 | 0.231393 |
| SCAF11 | 0.23035 |
| SMG7 | 0.229492 |
| HM13 | 0.229147 |
| FKBP10 | 0.228018 |
| EIF3D | 0.228009 |
| ALDH18A1 | 0.227628 |
| FPGS | 0.227115 |
| LSM14A | 0.225984 |
| TOMM20 | 0.221069 |
| LEPREL4 | 0.218251 |
| RPS6KC1 | 0.217382 |
| ILK | 0.215663 |
| EIF2A | 0.214452 |
| RHOA | 0.209245 |
| GABARAPL2 | 0.2074 |
| OSBPL11 | 0.205991 |
| GTF3C3 | 0.205866 |
| LACE1 | 0.202592 |
| ERP29 | 0.201958 |
| UBE2W | 0.200908 |
| ZNF707 | 0.200292 |
| SH2B1 | 0.199667 |
| FAM84B | 0.199091 |
| NMRAL1 | 0.1973 |
| UPF3A | 0.19649 |

TABLE 2-continued

| Gene name | Score |
|---|---|
| OXSR1 | 0.195023 |
| GLT8D1 | 0.19468 |
| POLR3H | 0.192373 |
| PEX3 | 0.190707 |
| USP10 | 0.189028 |
| IFT88 | 0.187595 |
| SPCS1 | 0.187005 |
| GARS | 0.186895 |
| KBTBD7 | 0.186141 |
| IFT52 | 0.18591 |
| FAM118A | 0.183433 |
| TBC1D22A | 0.182495 |
| SDR39U1 | 0.181102 |
| TRAPPC6B | 0.180793 |
| ZNF862 | 0.179803 |
| MYO10 | 0.178329 |
| DRAM1 | 0.178226 |
| ETV3 | 0.177354 |
| ZNF717 | 0.176982 |
| TCEA1 | 0.176339 |
| DOCK5 | 0.176044 |
| PRPSAP1 | 0.174043 |
| CHEK1 | 0.173579 |
| MBTPS2 | 0.171489 |
| EIF2D | 0.168544 |
| PAPOLA | 0.167602 |
| ADAT2 | 0.167348 |
| RNF168 | 0.166811 |
| TRIM39-RPP21 | 0.165746 |
| CYB561D1 | 0.164605 |
| ZNHIT6 | 0.16451 |
| NPEPPS | 0.163798 |
| SCAP | 0.16072 |
| NEK8 | 0.158951 |
| ZBTB2 | 0.153722 |
| PC | 0.151082 |
| SRSF9 | 0.150228 |
| ATG9B | 0.149411 |
| MTRR | 0.148323 |
| MGAT1 | 0.147344 |
| CHP1 | 0.146536 |
| TTPAL | 0.143218 |
| RHOT2 | 0.142693 |
| NRDE2 | 0.142634 |
| RECQL5 | 0.141793 |
| FAM20B | 0.138563 |
| PEMT | 0.136822 |
| MATR3 | 0.135653 |
| RMND1 | 0.135496 |
| ANKRD13C | 0.134347 |
| CEP57 | 0.134195 |
| ERI1 | 0.133557 |
| GZF1 | 0.133348 |
| ARID2 | 0.133333 |
| TFAP4 | 0.132025 |
| PELP1 | 0.131973 |
| SDHC | 0.131126 |
| DEDD | 0.127555 |
| OPA1 | 0.124978 |
| DDX58 | 0.124922 |
| SPCS2 | 0.124875 |
| ORAI1 | 0.122305 |
| LTBP3 | 0.120619 |
| RPGRIP1L | 0.119249 |
| EI24 | 0.119154 |
| TMED5 | 0.115144 |
| MRPL37 | 0.115089 |
| WASF3 | 0.115068 |
| CGGBP1 | 0.114847 |
| FCHO2 | 0.112279 |
| MAZ | 0.111982 |
| COL4A3BP | 0.110808 |
| POLK | 0.109563 |
| KLHDC2 | 0.108337 |
| MGST3 | 0.107594 |
| ZNF354A | 0.105456 |
| ATP5G2 | 0.104621 |
| ABCB8 | 0.100009 |
| ZNF212 | 0.098295 |
| SDCBP | 0.097676 |
| ZC3HC1 | 0.096694 |
| UBAP2L | 0.092845 |
| AGAP3 | 0.091209 |
| TLCD1 | 0.089469 |
| TMUB1 | 0.089402 |
| METTL25 | 0.089358 |
| NDUFS6 | 0.086553 |
| KLF10 | 0.086147 |
| PRKAR2A | 0.08528 |
| SAP30BP | 0.085141 |
| H6PD | 0.084118 |
| PFKM | 0.082449 |
| BIRC6 | 0.081694 |
| NACC1 | 0.080936 |
| TRIM39 | 0.080798 |
| GNB2 | 0.080304 |
| WRNIP1 | 0.079983 |
| KANSL1 | 0.07964 |
| AGAP1 | 0.079025 |
| STARD3 | 0.078322 |
| HNRNPU | 0.077945 |
| ZBTB37 | 0.077671 |
| ATL3 | 0.075683 |
| RNASEH2B | 0.074239 |
| LRRC47 | 0.073559 |
| MPHOSPH8 | 0.07235 |
| ATPAF1 | 0.071452 |
| WASL | 0.065913 |
| TOP2A | 0.065305 |
| GNB1L | 0.062161 |
| TES | 0.060784 |
| OMA1 | 0.060663 |
| NOL3 | 0.05983 |
| SLC25A3 | 0.058265 |
| YPEL1 | 0.05731 |
| NDST2 | 0.057236 |
| MIS18BP1 | 0.057031 |
| LZTR1 | 0.054916 |
| ZNF143 | 0.054338 |
| ARNTL | 0.053714 |
| HDAC4 | 0.047691 |
| ERAP1 | 0.045142 |
| NET1 | 0.043507 |
| TIMM22 | 0.043153 |
| DNAJB11 | 0.039978 |
| MBNL1 | 0.039222 |
| GLO1 | 0.036961 |
| NOC2L | 0.033787 |
| SMG6 | 0.03227 |
| MED20 | 0.028908 |
| SKIV2L | 0.028019 |
| DAZAP1 | 0.02794 |
| AMDHD2 | 0.025875 |
| DHX15 | 0.025638 |
| MPP5 | 0.024226 |
| NAAA | 0.023722 |
| IMMP2L | 0.023034 |
| CYB5RL | 0.021711 |
| IL1RAP | 0.020732 |
| SSR3 | 0.017183 |
| RPS6KB2 | 0.014079 |
| ARHGEF11 | 0.010611 |
| ASPSCR1 | 0.010098 |
| TBC1D22B | 0.009795 |
| 5-Mar | 0.00857 |
| RRN3 | 0.008502 |
| USP38 | 0.006288 |
| LEMD3 | 0.005841 |
| GORASP1 | 0.005008 |
| CCDC124 | 0.004782 |
| CNEP1R1 | 0.004368 |
| FADS2 | 0.003868 |
| PLK2 | 0.003828 |
| HGSNAT | 0.00371 |
| SGOL1 | 0.002023 |
| CDK5RAP3 | 0.001938 |

TABLE 2-continued

| Gene name | Score |
|---|---|
| KLHL22 | 0.000431 |
| SECISBP2 | −0.00447 |
| ANKRD46 | −0.00573 |
| HN1L | −0.00639 |
| SLC35E3 | −0.00819 |
| AKAP10 | −0.00943 |
| ATG13 | −0.01092 |
| RBM15B | −0.01241 |
| GYG1 | −0.0125 |
| HMOX2 | −0.01461 |
| RAD51AP1 | −0.01539 |
| DONSON | −0.01598 |
| EXOSC4 | −0.01626 |
| PPFIA1 | −0.01694 |
| ZC2HC1C | −0.01729 |
| OTUD7B | −0.01807 |
| SURF4 | −0.02304 |
| MAPK8 | −0.02651 |
| FNTA | −0.02865 |
| TICAM1 | −0.02878 |
| EXOC5 | −0.02925 |
| ZDHHC20 | −0.02967 |
| HNRNPA0 | −0.03025 |
| SRXN1 | −0.03159 |
| ZBED6 | −0.03394 |
| MYRIP | −0.03478 |
| GNA13 | −0.03515 |
| UEVLD | −0.03827 |
| DHX33 | −0.0399 |
| NUDCD1 | −0.0432 |
| TELO2 | −0.04494 |
| NBN | −0.045 |
| DSCC1 | −0.04553 |
| KATNAL1 | −0.04631 |
| KRIT1 | −0.04658 |
| CDK5RAP2 | −0.04747 |
| RFXANK | −0.04769 |
| DYNLRB1 | −0.04941 |
| IVNS1ABP | −0.04974 |
| AHCYL2 | −0.0507 |
| POGLUT1 | −0.05337 |
| ZNF658 | −0.05364 |
| FAM114A2 | −0.05446 |
| PSMD6 | −0.05458 |
| GUSB | −0.05548 |
| PAQR4 | −0.05573 |
| PIGU | −0.05575 |
| PDLIM5 | −0.05602 |
| ECD | −0.05655 |
| CEP57L1 | −0.05819 |
| TLK2 | −0.05989 |
| CPNE3 | −0.06042 |
| TUBGCP4 | −0.06257 |
| FAM3C | −0.06393 |
| CHTOP | −0.06442 |
| UBE2D2 | −0.06495 |
| PSEN1 | −0.06496 |
| WBSCR22 | −0.06511 |
| YIF1B | −0.06753 |
| GATAD1 | −0.07001 |
| EIF4E2 | −0.07017 |
| GORASP2 | −0.07045 |
| CLPTM1L | −0.07321 |
| RPL7 | −0.07387 |
| CHD1 | −0.07405 |
| HOMER1 | −0.07471 |
| NOC4L | −0.07866 |
| MTMR10 | −0.08099 |
| GCFC2 | −0.08162 |
| SMYD4 | −0.08193 |
| NTAN1 | −0.08277 |
| UBE2D3 | −0.08283 |
| FAM168B | −0.08286 |
| SMAGP | −0.08397 |
| WDR33 | −0.08444 |
| MCOLN1 | −0.08473 |
| CWF19L2 | −0.08524 |
| FNDC3B | −0.0874 |
| NUB1 | −0.08801 |
| FDXACB1 | −0.08841 |
| CPEB3 | −0.08959 |
| YTHDF2 | −0.09178 |
| HDDC2 | −0.09219 |
| GBE1 | −0.09325 |
| TMEM115 | −0.09422 |
| AP1AR | −0.09626 |
| CENPT | −0.09823 |
| RPL37 | −0.09899 |
| RANBP17 | −0.09944 |
| GABARAP | −0.10105 |
| LDB1 | −0.10123 |
| SGSH | −0.1015 |
| NKTR | −0.10268 |
| SMPDL3A | −0.10341 |
| SENP1 | −0.10349 |
| ZNF700 | −0.10477 |
| NFRKB | −0.10508 |
| MEF2BNB-MEF2B | −0.10571 |
| SNX4 | −0.10572 |
| SLC35E2B | −0.10801 |
| MLLT10 | −0.10863 |
| ZMYM5 | −0.10902 |
| SLC25A38 | −0.1097 |
| CCNC | −0.1098 |
| ACTL6A | −0.11093 |
| MRPS16 | −0.11115 |
| CS | −0.11309 |
| ANKRD13D | −0.11346 |
| SPOP | −0.11363 |
| METTL1 | −0.11441 |
| RPL10 | −0.11831 |
| PHYKPL | −0.11941 |
| NFKB1 | −0.12027 |
| TMEM14A | −0.12028 |
| ACP6 | −0.12208 |
| RNF13 | −0.1232 |
| MRFAP1L1 | −0.12428 |
| DICER1 | −0.12668 |
| NPL | −0.12807 |
| ARPC3 | −0.12838 |
| IGHMBP2 | −0.13 |
| GINS3 | −0.13204 |
| MTX2 | −0.13256 |
| ELF2 | −0.13818 |
| RPS20 | −0.13907 |
| ARL5B | −0.13962 |
| CYP51A1 | −0.13969 |
| ZNF131 | −0.14369 |
| LRRC8B | −0.14486 |
| CUL1 | −0.14564 |
| ZFR | −0.15398 |
| ZNF584 | −0.15463 |
| ZNF200 | −0.15726 |
| RPLP0 | −0.1581 |
| PRPF40B | −0.15958 |
| KLHL17 | −0.16038 |
| VPS33A | −0.16075 |
| RPP14 | −0.16176 |
| PGAM1 | −0.16217 |
| ATG14 | −0.16575 |
| TRNT1 | −0.16761 |
| TAF6L | −0.16769 |
| RPLP2 | −0.17159 |
| METAP1 | −0.17217 |
| SRR | −0.17416 |
| PIAS2 | −0.1744 |
| TBL1XR1 | −0.17442 |
| GADD45GIP1 | −0.17467 |
| PNN | −0.17694 |
| CDKN3 | −0.17768 |
| POLDIP2 | −0.1777 |
| SESN1 | −0.17931 |
| CYB5D2 | −0.18001 |
| MAP2K5 | −0.18092 |
| SMIM7 | −0.18206 |

TABLE 2-continued

| Gene name | Score |
|---|---|
| COG5 | −0.18396 |
| KLHL15 | −0.18692 |
| AAAS | −0.18723 |
| UBE2R2 | −0.18785 |
| SLC22A23 | −0.18892 |
| BYSL | −0.18941 |
| CDK8 | −0.1904 |
| BTAF1 | −0.19383 |
| APPBP2 | −0.19574 |
| ELK4 | −0.19589 |
| PAN2 | −0.19753 |
| NELFE | −0.19881 |
| STAT3 | −0.19899 |
| RHOD | −0.1996 |
| ZNF800 | −0.20119 |
| ZNF354B | −0.20129 |
| MARK3 | −0.2035 |
| ADSL | −0.20447 |
| PSMC2 | −0.20486 |
| ZNF23 | −0.20492 |
| PITPNC1 | −0.21249 |
| PRMT3 | −0.21311 |
| USP36 | −0.21381 |
| PPP6C | −0.21497 |
| ZNF286A | −0.21546 |
| DNAJC30 | −0.21605 |
| ZNF827 | −0.2165 |
| RNF114 | −0.2167 |
| POLR2D | −0.21959 |
| VPS45 | −0.22067 |
| PA2G4 | −0.22068 |
| TMEM38A | −0.22337 |
| POMP | −0.22439 |
| RNF32 | −0.22568 |
| EIF3M | −0.22601 |
| NUP153 | −0.22721 |
| ZNF398 | −0.22732 |
| PSMD3 | −0.22758 |
| NSUN5 | −0.22778 |
| ASCC3 | −0.22847 |
| TADA2A | −0.23004 |
| FKBP1A | −0.23166 |
| HIST1H4B | −0.23471 |
| ABCE1 | −0.23527 |
| SOX13 | −0.23537 |
| UNC50 | −0.23828 |
| NEK1 | −0.23988 |
| UBE2V2 | −0.24154 |
| RFC4 | −0.24158 |
| ANAPC10 | −0.24194 |
| OSTM1 | −0.24202 |
| HECTD2 | −0.24728 |
| MRPS28 | −0.24765 |
| FAM21A | −0.25336 |
| GART | −0.26174 |
| NDUFB7 | −0.26433 |
| UMPS | −0.26478 |
| ZNF451 | −0.26928 |
| MICU2 | −0.2706 |
| CCDC50 | −0.2718 |
| CCDC59 | −0.27231 |
| RGS10 | −0.27363 |
| MFAP3 | −0.27395 |
| DEK | −0.27453 |
| DDX1 | −0.27532 |
| BIRC2 | −0.27626 |
| RASSF3 | −0.27811 |
| DDX51 | −0.28131 |
| DNAJC9 | −0.28341 |
| RPS9 | −0.28391 |
| THAP9 | −0.29263 |
| POT1 | −0.29311 |
| BAZ1B | −0.29441 |
| ARHGAP11A | −0.29517 |
| SLC20A1 | −0.29594 |
| ZNF669 | −0.29632 |
| RBM7 | −0.29692 |
| VMP1 | −0.29782 |
| MPHOSPH6 | −0.29909 |
| NT5C3A | −0.30042 |
| PRPF39 | −0.30156 |
| RABIF | −0.30384 |
| DLAT | −0.30691 |
| HEXDC | −0.30906 |
| CYB561A3 | −0.31151 |
| LSM4 | −0.31182 |
| LNPEP | −0.31236 |
| DUS4L | −0.31417 |
| DNAJC2 | −0.31507 |
| CCT8 | −0.31715 |
| TIGD2 | −0.31797 |
| HNRNPF | −0.32007 |
| THG1L | −0.32016 |
| PDCL3 | −0.32082 |
| TMEM9B | −0.32295 |
| SAYSD1 | −0.32461 |
| PHF23 | −0.32463 |
| SLC35A5 | −0.32627 |
| GTPBP8 | −0.32721 |
| DDX23 | −0.33094 |
| SDHAF2 | −0.33423 |
| ARL14EP | −0.33715 |
| FAM49B | −0.3385 |
| TMEM106B | −0.33921 |
| INVS | −0.33974 |
| SMAD2 | −0.34053 |
| ERP44 | −0.34142 |
| UQCRFS1 | −0.34173 |
| SMG8 | −0.34286 |
| COA5 | −0.34718 |
| SMAD6 | −0.34764 |
| AK2 | −0.34918 |
| ST14 | −0.34935 |
| CDK11B | −0.35243 |
| LCOR | −0.35336 |
| AP5M1 | −0.35599 |
| PPP1R8 | −0.35616 |
| DCTN6 | −0.35775 |
| BHLHE40 | −0.36622 |
| ATP1B3 | −0.3692 |
| TECPR1 | −0.37112 |
| HARBI1 | −0.37609 |
| FBXL5 | −0.38026 |
| ZNF770 | −0.38284 |
| RAN | −0.38518 |
| FUT4 | −0.39401 |
| TONSL | −0.39627 |
| ETNK1 | −0.39864 |
| ACP2 | −0.39922 |
| ZNF124 | −0.39983 |
| PDSS1 | −0.40203 |
| METTL9 | −0.40662 |
| GCSH | −0.41353 |
| CISD2 | −0.41638 |
| RPF1 | −0.419 |
| RIOK1 | −0.42118 |
| UNK | −0.42211 |
| SPA17 | −0.42562 |
| APBA3 | −0.43054 |
| RRP8 | −0.43185 |
| RPP40 | −0.43195 |
| SRP19 | −0.43749 |
| NOTCH1 | −0.44308 |
| SPPL2A | −0.45426 |
| GPS2 | −0.45545 |
| KLHL20 | −0.45819 |
| MRPL21 | −0.45847 |
| FAIM | −0.46443 |
| NDUFA6 | −0.46622 |
| CDKN2AIP | −0.47159 |
| CPSF7 | −0.47381 |
| RPUSD1 | −0.47881 |
| TRMT10B | −0.4797 |
| GNPNAT1 | −0.47995 |
| ENY2 | −0.48022 |
| FUBP3 | −0.4867 |

TABLE 2-continued

| Gene name | Score |
| --- | --- |
| PINX1 | −0.49018 |
| SLC41A1 | −0.49214 |
| ZCCHC3 | −0.49824 |
| FASTKD3 | −0.49842 |
| CAPRIN2 | −0.49844 |
| TRPM7 | −0.50122 |
| SPATA7 | −0.50672 |
| HUS1 | −0.51389 |
| RBM17 | −0.52226 |
| S100A13 | −0.52761 |
| TXN | −0.52872 |
| DLD | −0.54 |
| TMEM60 | −0.54156 |
| TMEM138 | −0.55404 |
| BUB1B | −0.55464 |
| TIGD1 | −0.55618 |
| MRPL42 | −0.56435 |
| PUS7 | −0.56467 |
| IKBKAP | −0.56595 |
| ZSCAN29 | −0.57373 |
| MYO6 | −0.57842 |
| IFRD1 | −0.57894 |
| MYL12B | −0.58321 |
| CPT1A | −0.5905 |
| MTMR6 | −0.59057 |
| NAA38 | −0.59892 |
| SNRPA1 | −0.60056 |
| NSMCE4A | −0.60422 |
| ATP5J2-PTCD1 | −0.60451 |
| HSD11B2 | −0.60607 |
| ZBTB26 | −0.60952 |
| TCTA | −0.61011 |
| HEBP2 | −0.61555 |
| HSPH1 | −0.61743 |
| SMIM19 | −0.61972 |
| MRPS36 | −0.63469 |
| RBM18 | −0.6378 |
| SPG21 | −0.64 |
| PEX6 | −0.64599 |
| PMS1 | −0.65048 |
| SLC25A21 | −0.65089 |
| DYNLL1 | −0.65209 |
| PDS5B | −0.65278 |
| SMIM12 | −0.6556 |
| FAM206A | −0.67537 |
| MPLKIP | −0.68001 |
| POLE3 | −0.68339 |
| MRPL36 | −0.69785 |
| FAM76B | −0.70276 |
| MEF2BNB | −0.70322 |
| MTHFD2L | −0.70961 |
| ZNF823 | −0.71217 |
| TMEM199 | −0.72137 |
| FAM162A | −0.72796 |
| ORMDL1 | −0.73362 |
| SEMA3C | −0.73719 |
| MRRF | −0.73765 |
| CNTLN | −0.74277 |
| TRMT1 | −0.75516 |
| ATAD2B | −0.76239 |
| UBE2N | −0.76381 |
| GTPBP10 | −0.76571 |
| ATP5J2 | −0.77472 |
| COA6 | −0.77821 |
| TAF1D | −0.80534 |
| CNIH4 | −0.80613 |
| PRKCD | −0.80671 |
| NAMPT | −0.81921 |
| H3F3B | −0.83064 |
| MYO5C | −0.87157 |
| VIMP | −0.88848 |
| NUDT4 | −0.91756 |
| TXNL1 | −0.92043 |
| MRPL54 | −0.9313 |
| ZNF548 | −0.9507 |
| CCDC58 | −0.96517 |
| PPM1E | −1.02721 |
| NT5C2 | −1.06613 |
| NDRG1 | −1.09845 |
| PSTK | −1.20353 |
| TJP1 | −1.35726 |
| STK10 | −1.6975 |
| BBS10 | −1.86292 |
| KLF4 | −2.0642 |
| STARD4 | −2.26391 |
| TMPRSS2 | −2.46887 |
| TNFRSF19 | −3.0371 |
| ZNF385B | −4.52898 |

ENZ-Resistant ARPC Growth Driven by ARBS-Gi Locus Genes

Figure 4A:
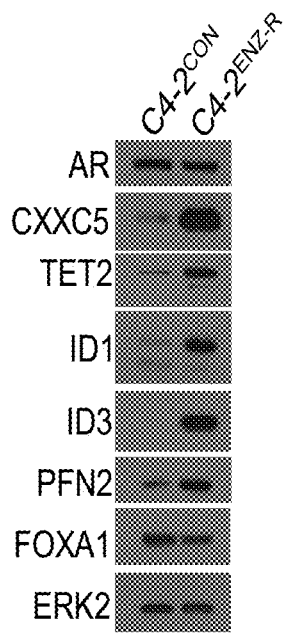
Figure 4B:
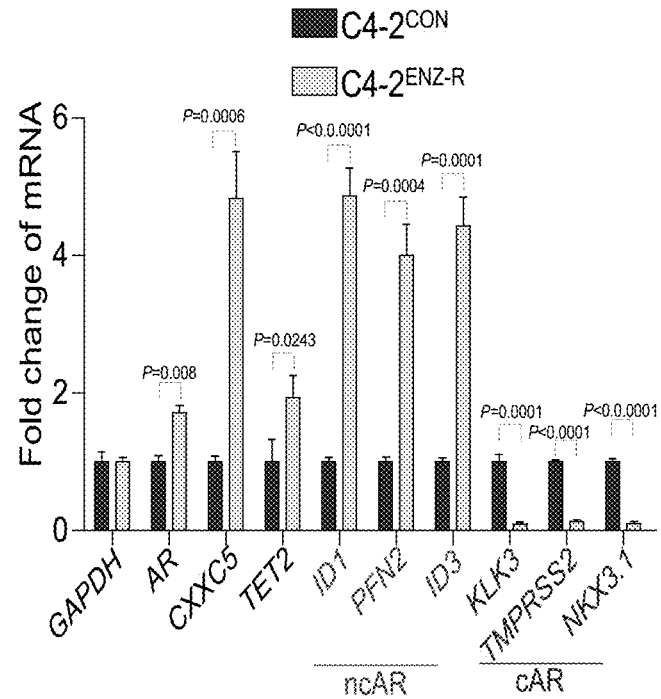
Figure 4C:
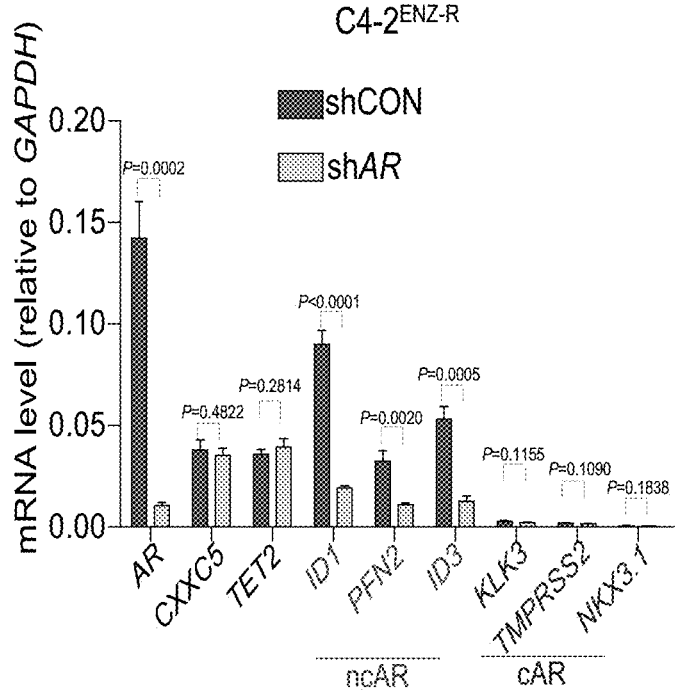
Figure 4D:
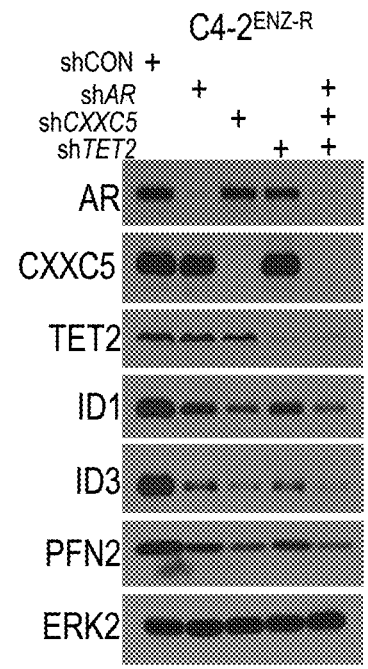

To assess the relevance of the gained AR binding, the role of its downstream target genes in the development of ENZ resistance were assessed. Western blot and RT-qPCR analyses confirmed upregulation of CXXC5, TET2 and the ncAR targets at ARBS-Gi loci, such as ID1, ID3, and PFN2, in ENZ-resistant C4-2 cells (FIG. 4A). In contrast, FOXA1 expression was moderately decreased in C4-2ENZ-R cells (FIG. 4A), consistent with the decreased FOXA1 binding in the cAR target genes such as KLK3, TMPRSS2 and NKX3.1 (FIG. 3E). Further, ncAR gene expression remained AR-dependent at both mRNA and protein level in C4-2ENZ-R cells (FIGS. 4C, 4D). Such effect was further augmented by co-knockdown of AR with CXXC5 and TET2 (FIG. 4D). In contrast, expression of cAR target genes such as KLK3, TMPRSS2 and NKX3.1 was reduced by AR knockdown in C4-2ENZ-R cells (FIG. 4C). This result is not surprising because the basal level of these genes was already low in C4-2ENZ-R compared to control cells (FIGS. 3E, 4C).

Figure 4H:
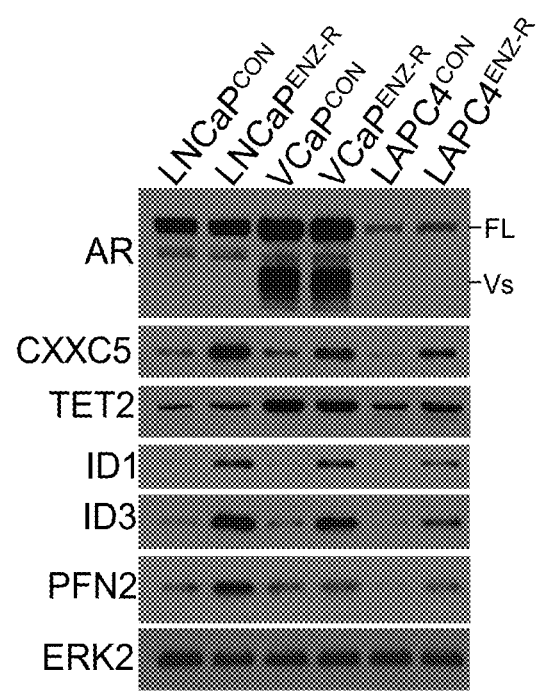
Figure 4I:
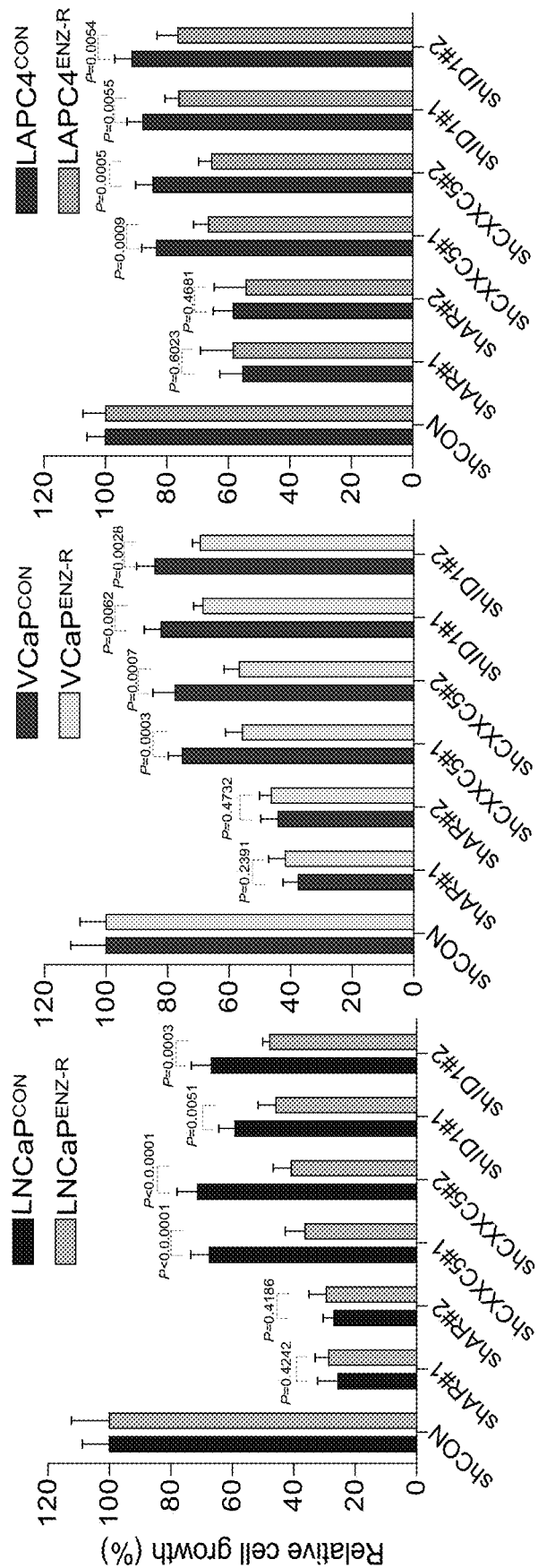

To determine the causal role of the ncAR target genes at ARBS-Gi loci in ENZ-resistant cells, ID1, ID3 and PFN2 were individually knocked down using gene-specific shRNAs in both C4-2CON and C4-2ENZ-R cells. Knockdown of ID1, ID3, or PFN2 restored ENZ sensitivity in C4-2ENZ-R cells (FIGS. 4E, 4G). Similarly, little or no changes in AR expression was detected in the other three ENZ-resistant ARPC cell lines. However, expression of CXXC5, ID1, ID3, and PFN2 were upregulated in ENZ-treated cells compared to the control cells, except TET2 expression in VCaPENZ-R cells (FIG. 4H). The growth of these ENZ-resistant cell lines remained AR-dependent, remaining consistent with the ENZ-resistance in the parental cell lines, but were more sensitive to ENZ after knockdown of CXXC5 or ID1 when compared to the control cells (FIG. 4I). These data indicate that CXXC5-dependent ncAR transcription program is a common mechanism driving ENZ-resistance in ARPC cells.

Overcoming ENZ Resistance Using the Combination of BET and CBP/p300 Inhibitors

Figures 5A, 5B:
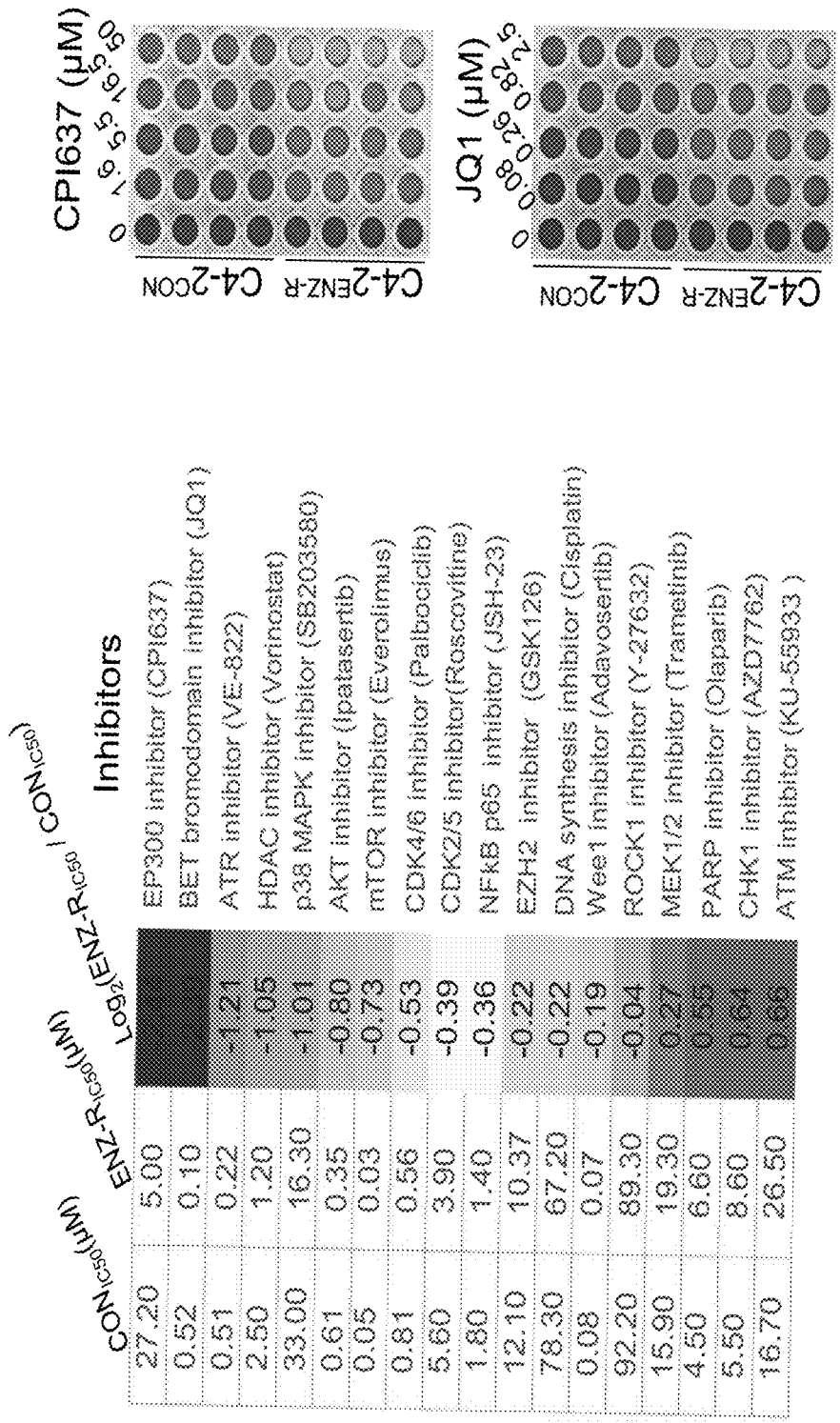
FIGS. 5A-5D: Dual inhibition of BET and CBP/p300 overcomes ENZ-resistance in ARPCa. A: Heatmap showing the sensitivity of control (C4-2CON) and enzalutamide-resistant C4-2 cells (C4-2ENZ-R) to various inhibitor. B-C: C4-2CON and C4-2ENZ-R cells were treated with the indicated concentrations of BET inhibitor (JQ1) and CBP/p300 inhibitor (CPI637) for 4 days, the cell proliferation was measured by SRB assay, and the 96 well plates were imaged. Data are represented as means±s.d., n=4. Statistical significance was determined by two-way ANOVA. D: C4-2ENZ-R cells were treated with the indicated concentrations of ENZ, JQ1, CPI637, or a combination of JQ1 and CPI-637, and cell proliferation was measured by a SRB assay. Data are represented as means±s.d., n=6. Statistical significance was determined by two-way ANOVA.
Figure 5C:
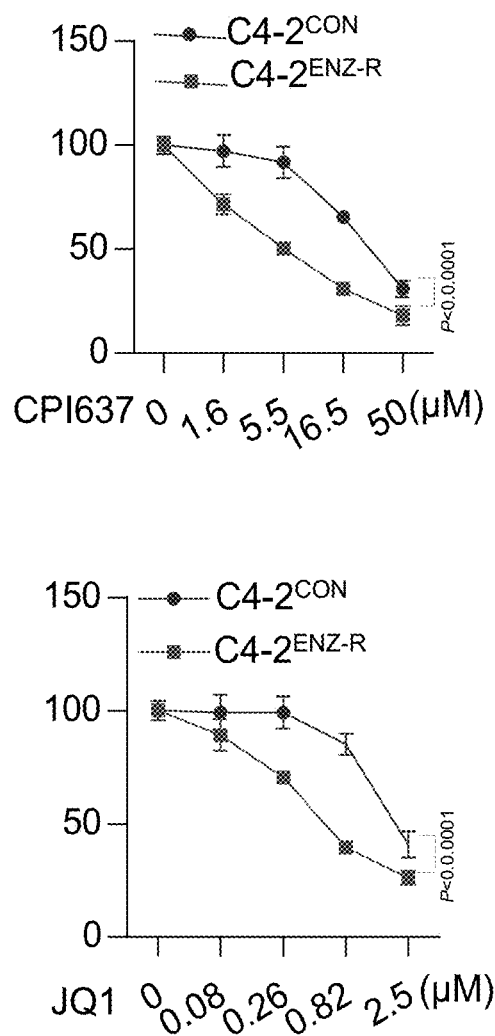
Figure 5D:
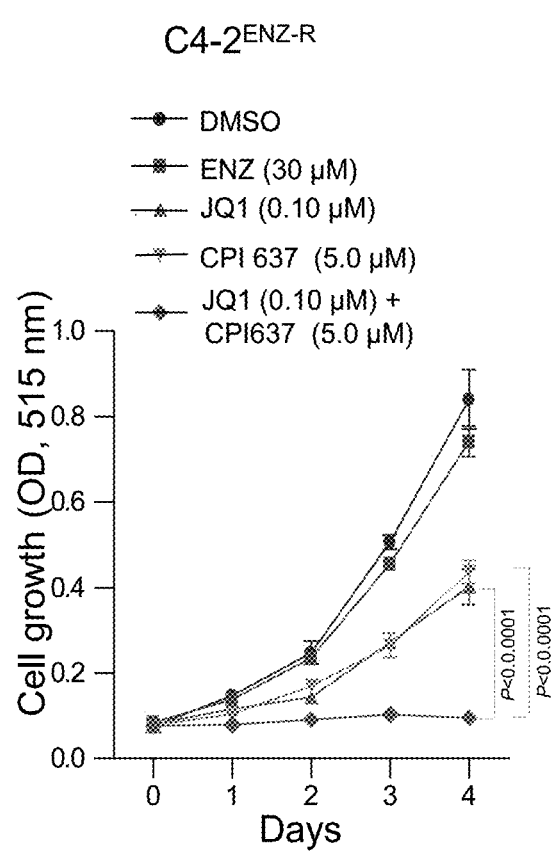

Next, methods for achieving pharmacologically intervention in ARE-independent ENZ-resistance in ARPC was investigated. First, assessments were made regarding the sensitivity of C4-2ENZ-R cells to the inhibitors of functionally diversified signaling pathways. By comparing the half maximal inhibitory concentration (IC50) of the inhibitors in C4-2ENZ-R and C4-2CON cells, it was discovered that C4-2ENZ-R cells were much more sensitive to the CBP/p300 inhibitor CPI637 and the BET inhibitor JQ1 than the control cells (FIGS. 5A-5C), highlighting that the ENZ-resistant ARPC cells can be specifically targeted by inhibition of BET and CBP-p300 pathways. Indeed, the combination of CPI637 and JQ1 resulted in much greater inhibition of growth of C4-2ENZ-R cells than treatment with each inhibitor alone (FIG. 5D). These results indicate that dual inhibition of BET and CBP/p300 family proteins can effectively block the growth of ENZ-resistant ARPC cells.

Figure 6A:
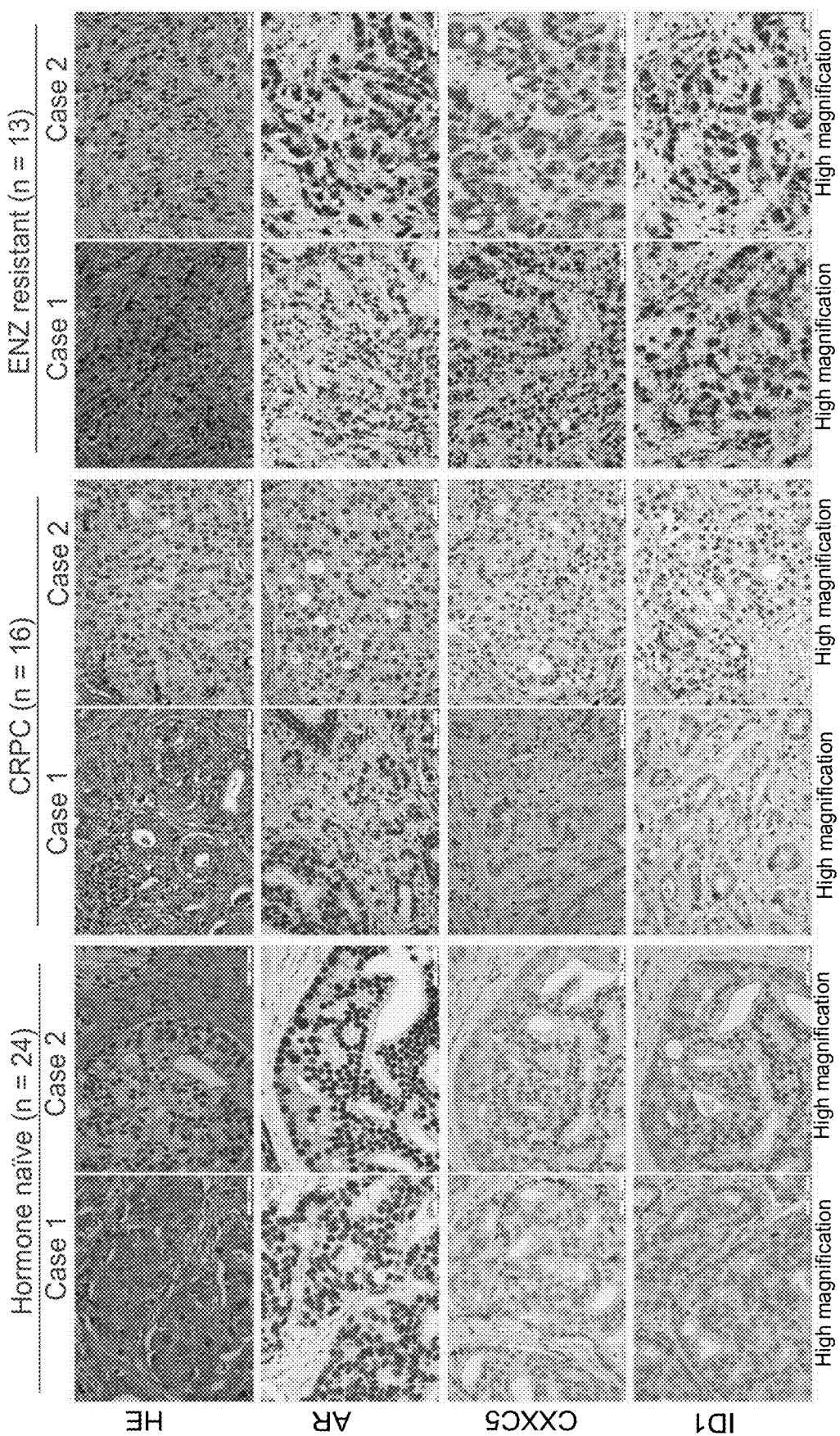
FIGS. 6A-6G. The ncAR activity is involved in acquisition of ENZ resistance in clinical settings. A-B: H&E staining and IHC for AR, CXXC5, and ID1 protein in hormone naïve PC, CRPC, and ENZ-resistant PC patients. Representative images (scale bar, 50 µm), and quantified data are show in (a) and (b), respectively. C: Western blot analysis of AR, CXXC5, TET2, ID1, PFN2, and ID3 protein in CRPC and ENZ-resistant PDXs (n=3 tumors/PDX). D-F: C4-2ENZ-R cells suspended in 0.1 mL matrigel were injected into the right flank of 6-week old male SCID mice. After the tumor volume reached about 100 mm$^3$, mice in each tumor type group were randomly assigned and were treated with vehicle, 10 mg/kg ENZ, 10 mg/kg CPI637, 50 mg/kg JQ1, or a combination of 50 mg/kg JQ1 and 10 mg/kg CPI637 daily. Tumor size was measured every 4 days (d). After 28 days of treatment, tumors isolated from mice were photographed (e), and tumor weight was measured (f). Data are represented as means±s.d., n=8. Statistical significance was determined by two-way ANOVA. G: A hypothetical working model. The ARE-dependent canonical AR (cAR) function is ENZ-sensitive. However, the CXXC5-mediated, ARE-independent noncanonical AR (ncAR) activity is resistant to ENZ treatment, thereby contributing to ENZ resistance in ARPC. However, the ncAR function can be overcome with dual inhibition of BET and CBP/p300 signaling pathways.
Figure 6B:
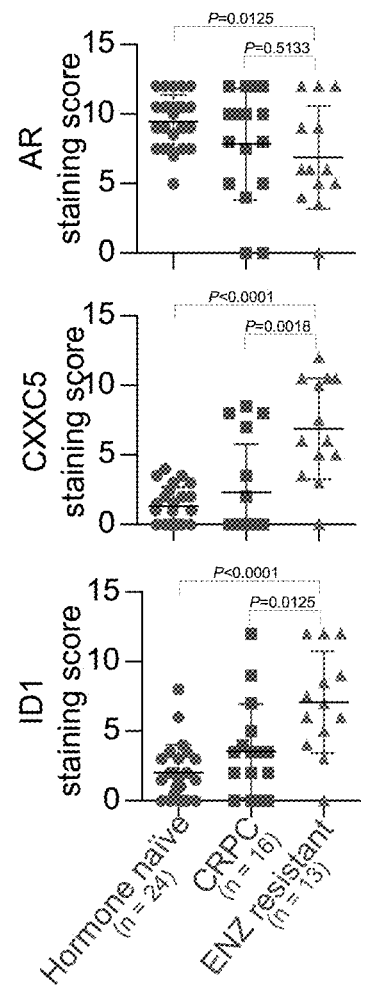
Figure 11A:
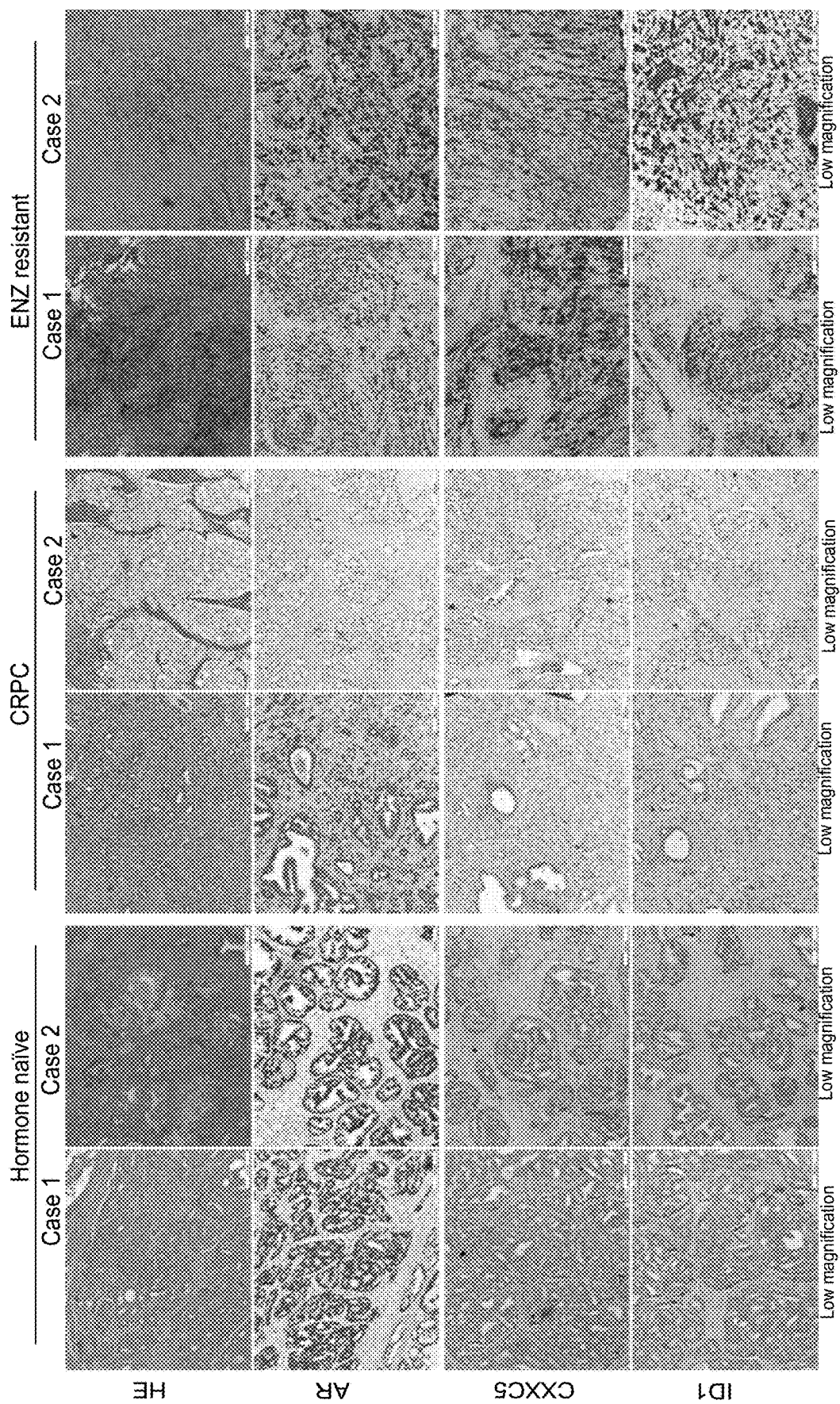
FIG. 11A-D. Upregulation of CXXC5 and ID1 in AFI-resistant PCa patients. A: H&E staining and IHC for AR, CXXC5, and ID1 in hormone naïve, CRPC and ENZ-resistant PC patient specimens. Scale bar, 200 µm. B: H&E staining and IHC for AR, CXXC5, and ID1 in ABI-resistant ARPC patient specimens. Scale bar, 200 m (low magnification); 50 m (high magnification). C-D: Comparison of ENZ response in CRPC and ENZ-resistant PDXs. CRPC and ENZ-resistant PDXs were planted into the right flank of 6 week-old male SCID mice. After the tumor volume reached about 100 mm$^3$, mice were randomly assigned within each tumor group and treated with 10 mg/kg of ENZ vehicle daily. Tumor size was measured every 4 days (C). After 32 days of treatment, tumors were isolated and photographed (D). Data are represented as means±s.d., n=8. Statistical significance was determined by two-way ANOVA.
Figure 11B:
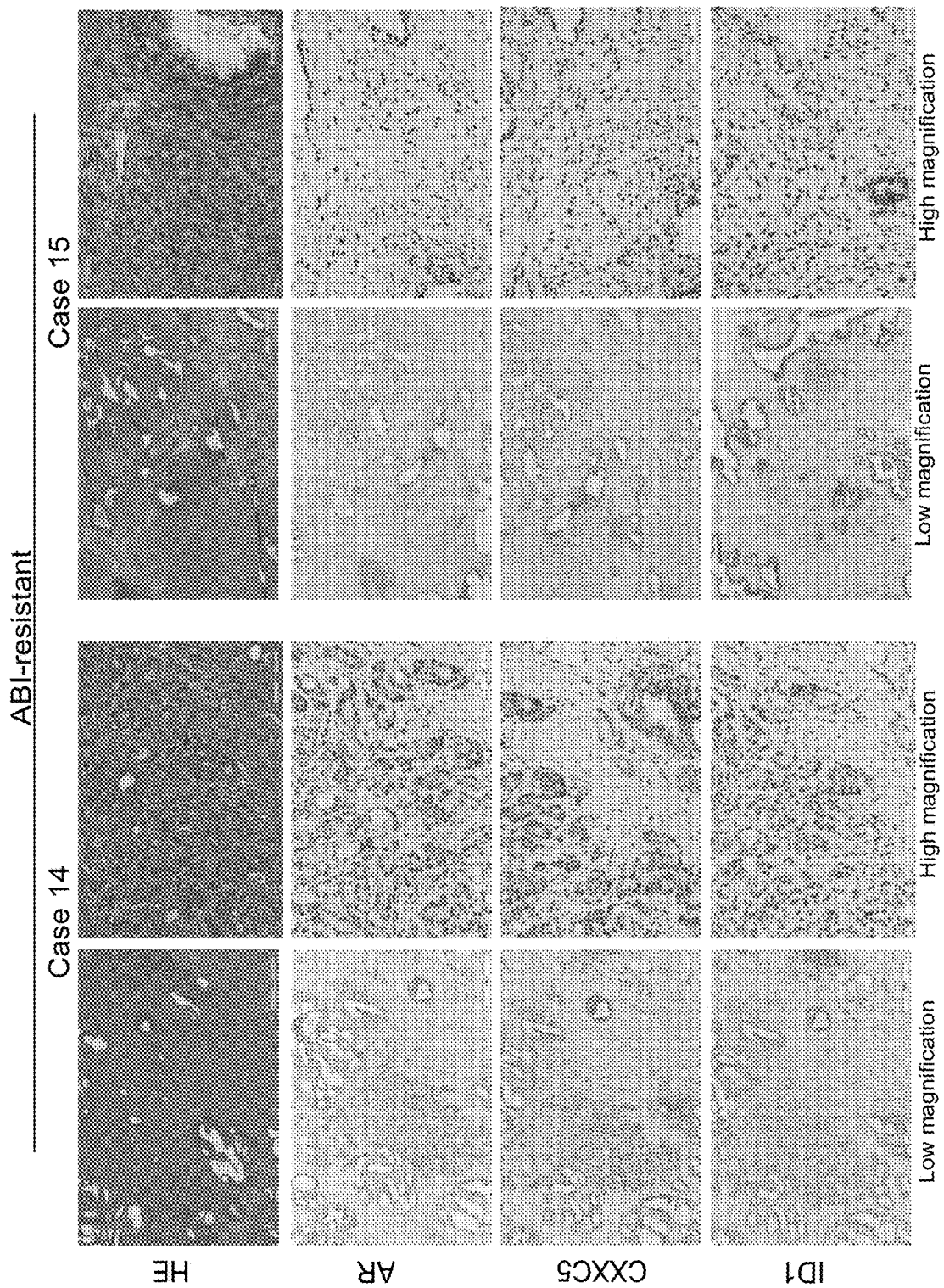
Figure 11C:
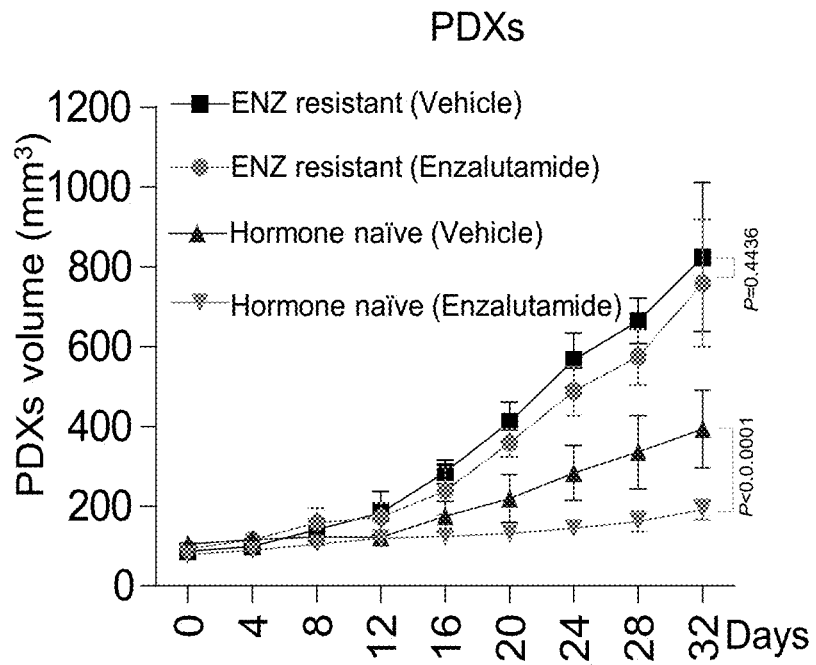
Figure 11D:
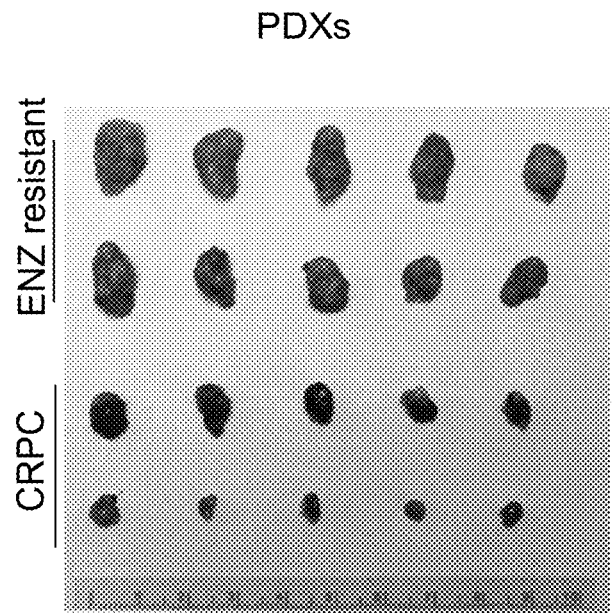

The Role of the ncAR Activity in Acquisition of ENZ Resistance in Clinical Settings Next, IHC was used to examine the expression of AR, CXXC5 and ID1 protein in a group of patients diagnosed with hormone naïve prostate cancer (n=24), CRPC (n=16) or ENZ-resistant prostate cancer (n=13) in order to validate the significance of the gained ncAR program in the development of ENZ resistance in clinical settings. AR protein was expressed in almost all the specimens (FIGS. 6A, 6B; FIG. 11a) with exception of one ENZ-resistant and two CRPC cases in which AR expression was low (FIG. 6B; Table 3). While AR protein level was slightly lower in the ENZ-resistant specimen than hormone naïve PC specimens, expression of CXXC5 and its downstream target ID1 was upregulated in ENZ-resistant tumors (FIG. 6A, 6B; Table 3). Consistent with the result in the C4-2B CRPC cell line (FIG. 2I), CXXC5 protein was also upregulated in certain CRPC patient specimens (FIGS. 6A, 6B). Intriguingly, staining of CXXC5 and ID1 protein was also detected in two out of two abiraterone (ABI)-resistant ARPCs examined (FIG. 11B).

TABLE 3

| Gene | logFC | logCPM | PValue | FDR |
|---|---|---|---|---|
| CBLN2 | 10.51547624 | 5.668678783 | 0 | 0 |
| FRAS1 | 6.08313794 | 4.906381423 | 0 | 0 |
| DPP4 | −5.356950384 | 6.85286046 | 0 | 0 |
| THBS1 | −5.405142129 | 7.0722837 | 0 | 0 |
| TENM1 | −5.637470238 | 5.759980758 | 0 | 0 |
| ASRGL1 | −6.104946525 | 6.289353099 | 0 | 0 |
| PHLDA1 | −6.694297836 | 4.782555087 | 0 | 0 |
| RPS4Y1 | −6.960662865 | 4.526112887 | 0 | 0 |
| AFF3 | −7.44685209 | 4.481793424 | 0 | 0 |
| PRUNE2 | −7.54099142 | 8.151354408 | 0 | 0 |
| CTAG2 | −7.610124143 | 4.432792657 | 0 | 0 |
| NAV3 | −7.783441667 | 4.558271556 | 0 | 0 |
| USP9Y | −8.108783458 | 4.597925175 | 0 | 0 |
| LAMA1 | −8.46616437 | 4.703180662 | 0 | 0 |
| BEND4 | −8.470281863 | 4.154993656 | 0 | 0 |
| TRPM8 | −9.380222631 | 4.826363329 | 0 | 0 |
| GULP1 | −9.43627029 | 8.39811411 | 0 | 0 |
| SYT4 | −9.877078838 | 8.339523859 | 0 | 0 |
| TFPI | −10.00184633 | 6.967265135 | 0 | 0 |
| ST6GALNAC1 | −10.08102582 | 7.036056605 | 0 | 0 |
| SLC22A3 | −10.37231911 | 5.462099694 | 0 | 0 |
| LOC101927482 | −7.855503023 | 3.736499485 | 1.51E−305 | 8.04E−303 |
| KCNH8 | −9.81267391 | 3.507077819 | 2.82E−303 | 1.44E−300 |
| BMPR1B | −7.123150074 | 3.944141663 | 1.45E−302 | 7.09E−300 |
| PCDH19 | 8.849591953 | 2.897434281 | 4.50E−302 | 2.11E−299 |
| ARHGAP28 | −5.231492132 | 5.677364246 | 4.85E−295 | 2.19E−292 |
| IGF1 | −5.849029858 | 4.587505448 | 2.30E−293 | 9.99E−291 |
| PCDH7 | 4.805331698 | 6.29048798 | 4.65E−287 | 1.95E−284 |
| PMEPA1 | −4.854975827 | 6.432669082 | 5.07E−285 | 2.05E−282 |
| LONRF2 | 5.447595617 | 4.275978797 | 4.57E−283 | 1.79E−280 |
| ALDH1A3 | −5.265144244 | 5.056755792 | 2.42E−281 | 9.14E−279 |
| DDX3Y | −8.146594553 | 3.266893751 | 2.09E−279 | 7.66E−277 |
| PLXDC2 | 4.849884793 | 5.550036362 | 1.13E−271 | 3.91E−269 |
| ADAM7 | −10.05397004 | 3.075483439 | 1.11E−271 | 3.91E−269 |
| PXDN | −6.77313771 | 3.544142697 | 6.66E−268 | 2.23E−265 |
| TTTY15 | −7.739546012 | 3.225886922 | 9.46E−267 | 3.08E−264 |
| CYP7A1 | 8.018195787 | 2.479470071 | 5.52E−265 | 1.75E−262 |
| NPR3 | 4.796516265 | 5.360496539 | 1.42E−264 | 4.39E−262 |
| THSD7B | 7.856776693 | 2.424172466 | 2.98E−261 | 8.95E−259 |
| K1AA1324 | 5.192939839 | 3.957843569 | 3.41E−257 | 9.98E−255 |
| TXLNGY | −7.696715889 | 3.012003487 | 6.32E−257 | 1.81E−254 |
| SLC16A3 | −5.082980208 | 4.568110046 | 1.42E−256 | 3.95E−254 |
| MBNL2 | 5.961816179 | 3.06345888 | 2.27E−256 | 6.19E−254 |
| PREX1 | 4.436150611 | 5.905931083 | 5.30E−253 | 1.41E−250 |
| CHRNA2 | −7.176796797 | 3.016120031 | 1.61E−245 | 4.19E−243 |
| KLK3 | −4.311806518 | 9.308784406 | 1.03E−244 | 2.62E−242 |
| ACOX2 | −5.624700877 | 3.528260367 | 5.90E−242 | 1.47E−239 |
| CDH3 | 4.250543207 | 5.855969184 | 7.80E−236 | 1.91E−233 |
| MECOM | 5.66790842 | 2.76392553 | 1.19E−228 | 2.85E−226 |
| CXORF57 | 5.39403131 | 2.977290403 | 5.38E−228 | 1.26E−225 |
| SPON2 | −4.165244413 | 6.807864328 | 1.19E−227 | 2.74E−225 |
| GREB1 | −4.638637318 | 4.529885766 | 2.65E−226 | 5.97E−224 |
| PDGFC | 5.452632657 | 2.858223415 | 4.56E−226 | 1.01E−223 |
| KCNJ3 | 5.572045615 | 2.751892588 | 1.78E−224 | 3.87E−222 |
| ELOVL2 | −6.472734149 | 2.882318057 | 1.09E−223 | 2.33E−221 |
| TUBA3D | −4.165516141 | 5.317987875 | 2.17E−223 | 4.55E−221 |
| PKIA | 7.150176429 | 2.021395515 | 7.45E−223 | 1.53E−220 |
| ARHGEF26 | −4.067197259 | 8.46143183 | 2.57E−222 | 5.18E−220 |
| MATN2 | 4.652734085 | 3.755982091 | 1.37E−221 | 2.72E−219 |
| EIF1AY | −7.65219729 | 2.582952352 | 4.58E−221 | 8.95E−219 |
| LRRN1 | 4.523253536 | 4.031565346 | 2.30E−220 | 4.42E−218 |

TABLE 3-continued

| Gene | logFC | logCPM | PValue | FDR |
|---|---|---|---|---|
| ZFY | −7.822914275 | 2.500964275 | 4.73E−216 | 8.94E−214 |
| C2ORF54 | 4.034083947 | 5.270666023 | 3.30E−215 | 6.15E−213 |
| PGC | −4.965742565 | 3.709680153 | 6.73E−215 | 1.23E−212 |
| ZNF385B | −4.530157384 | 4.255503322 | 7.24E−215 | 1.31E−212 |
| ABCC4 | −3.976774874 | 8.383819571 | 1.21E−214 | 2.14E−212 |
| DUSP4 | −4.344782664 | 4.950403225 | 7.59E−214 | 1.33E−211 |
| KIRREL | 4.821897294 | 3.177640319 | 5.05E−212 | 8.71E−210 |
| ELOVL7 | −3.986306848 | 6.309027099 | 2.64E−211 | 4.49E−209 |
| TUBA3E | −4.288171828 | 4.617058415 | 7.14E−211 | 1.20E−208 |
| ITGBL1 | 6.915910473 | 1.852965847 | 3.19E−209 | 5.26E−207 |
| SLPI | −4.400185037 | 4.326509031 | 1.67E−207 | 2.72E−205 |
| KDM5D | −7.877175012 | 2.416401056 | 3.74E−207 | 6.01E−205 |
| WWTR1 | −8.384473779 | 2.364780486 | 6.04E−206 | 9.57E−204 |
| MAF | −5.104592433 | 3.325191709 | 1.35E−204 | 2.11E−202 |
| KLHL1 | −5.640399605 | 2.900418537 | 3.21E−203 | 4.96E−201 |
| C2ORF72 | −4.382234712 | 4.257910553 | 7.19E−203 | 1.09E−200 |
| GALNT13 | 6.730598442 | 1.829874042 | 2.60E−202 | 3.90E−200 |
| TCEAL2 | 6.515767014 | 1.80180725 | 6.51E−201 | 9.65E−199 |
| LINC00161 | −4.805387315 | 3.434278258 | 3.03E−200 | 4.45E−198 |
| GLRB | 7.938402838 | 1.647047649 | 1.71E−199 | 2.48E−197 |
| TMTC1 | −5.578026174 | 2.812637215 | 3.01E−199 | 4.30E−197 |
| TARP | −7.14466681 | 2.299745522 | 9.68E−198 | 1.37E−195 |
| PABPC5 | 5.053407357 | 2.571424907 | 3.40E−196 | 4.74E−194 |
| CYP11A1 | −10.33890532 | 2.069025623 | 8.65E−196 | 1.19E−193 |
| MUM1L1 | 5.212051137 | 2.372451137 | 1.11E−193 | 1.52E−191 |
| HPGD | −7.465105186 | 2.291024452 | 1.18E−193 | 1.59E−191 |
| ZNF711 | 4.294535604 | 3.517790758 | 2.88E−192 | 3.84E−190 |
| SLC45A3 | −3.749431542 | 6.588434078 | 4.26E−192 | 5.62E−190 |
| NFIB | −4.183325771 | 4.354047289 | 4.13E−191 | 5.38E−189 |
| TNFAIP2 | 3.908538452 | 4.772243262 | 9.49E−191 | 1.22E−188 |
| ADD2 | 6.213744625 | 1.76124739 | 2.06E−189 | 2.62E−187 |
| GPC5-AS1 | −7.512668292 | 2.052844449 | 5.19E−188 | 6.54E−186 |
| GCNT1 | −3.993223917 | 4.666162866 | 3.14E−187 | 3.92E−185 |
| PDGFD | 4.75741513 | 2.637836379 | 9.13E−187 | 1.13E−184 |
| ROBO1 | 4.005118008 | 4.037542813 | 2.13E−186 | 2.60E−184 |
| NR2F1 | 3.711648959 | 5.036514108 | 3.60E−186 | 4.35E−184 |
| CXXC4 | 6.92929321 | 1.482231953 | 5.81E−186 | 6.95E−184 |
| PEG3 | −8.304700168 | 2.046419546 | 3.15E−185 | 3.73E−183 |
| HOXD13 | 4.042804984 | 3.843630054 | 1.03E−183 | 1.21E−181 |
| FGF13 | 3.683238797 | 4.841501187 | 4.15E−183 | 4.82E−181 |
| LUZP2 | 3.621577836 | 6.37351231 | 7.67E−183 | 8.81E−181 |
| ALDH1L2 | 3.666689294 | 4.871003577 | 5.20E−182 | 5.92E−180 |
| BST2 | −5.577420123 | 2.436315031 | 2.80E−181 | 3.15E−179 |
| ELOVL6 | 3.590644249 | 6.619497177 | 1.11E−180 | 1.24E−178 |
| HSPB8 | 4.320670936 | 3.008007946 | 1.23E−180 | 1.36E−178 |
| SAGE1 | 4.191899596 | 3.239627636 | 5.76E−180 | 6.31E−178 |
| RBP5 | 4.046612139 | 3.603283601 | 9.02E−180 | 9.79E−178 |
| AADAT | −3.664511538 | 4.954136752 | 4.98E−178 | 5.35E−176 |
| MST1R | 4.533403122 | 2.642490961 | 5.10E−178 | 5.43E−176 |
| WBSCR17 | 8.091793011 | 1.326250199 | 2.24E−177 | 2.36E−175 |
| GPR158 | −3.882506329 | 4.290187769 | 2.10E−175 | 2.20E−173 |
| KCNN2 | −3.682814579 | 4.778944709 | 5.91E−175 | 6.13E−173 |
| TSPAN7 | 4.44775479 | 2.59573356 | 8.19E−174 | 8.42E−172 |
| TEX19 | 3.551668895 | 4.749336525 | 1.38E−171 | 1.41E−169 |
| SCD5 | 3.67740531 | 4.42973597 | 4.74E−170 | 4.80E−168 |
| CAMK2N1 | −4.209240273 | 3.413274306 | 6.51E−170 | 6.52E−168 |
| CA13 | −5.886210642 | 2.197056203 | 1.23E−169 | 1.22E−167 |
| ATP10D | 5.567432617 | 1.625246061 | 6.25E−169 | 6.16E−167 |
| SGK2 | 4.565535864 | 2.226376399 | 6.08E−166 | 5.94E−164 |
| NETO1 | −3.4498688 | 5.939850194 | 5.82E−165 | 5.64E−163 |
| DSC1 | −6.168362826 | 1.988370549 | 2.50E−164 | 2.40E−162 |
| ZNF812 | −7.143054966 | 1.698475922 | 5.47E−164 | 5.21E−162 |
| TRPS1 | 3.427522908 | 4.846032464 | 1.60E−162 | 1.51E−160 |
| SLFN13 | −5.511062374 | 2.070230007 | 2.93E−162 | 2.75E−160 |
| PLA1A | −5.430432632 | 2.138576533 | 6.16E−162 | 5.74E−160 |
| CDH19 | 4.632735595 | 2.091005817 | 1.73E−161 | 1.60E−159 |
| CRIP2 | 3.396554816 | 5.179338774 | 2.98E−161 | 2.73E−159 |
| TMEFF2 | −5.105452797 | 2.294411942 | 4.07E−160 | 3.70E−158 |
| ZNF91 | −3.436671234 | 5.00721576 | 6.67E−160 | 6.01E−158 |
| DOCK8 | −5.234632635 | 2.175482917 | 1.85E−158 | 1.66E−156 |
| ALDH1A1 | −7.380885449 | 1.592724717 | 2.12E−158 | 1.89E−156 |
| ELL2 | −3.260713513 | 6.618473994 | 1.55E−152 | 1.37E−150 |
| EPHA3 | 3.192759908 | 9.348458197 | 5.22E−150 | 4.56E−148 |
| CDH26 | −4.41051879 | 2.495979034 | 2.05E−149 | 1.78E−147 |
| TRHDE | 4.381256615 | 1.953046302 | 3.94E−149 | 3.39E−147 |
| PDE10A | −4.92056566 | 2.087930567 | 6.18E−148 | 5.29E−146 |
| SLC30A2 | −6.00706994 | 1.777309172 | 9.93E−148 | 8.44E−146 |
| KLK2 | −3.164997943 | 8.105470005 | 6.12E−147 | 5.16E−145 |

TABLE 3-continued

| Gene | logFC | logCPM | PValue | FDR |
|---|---|---|---|---|
| UNC80 | −6.020674997 | 1.800238683 | 3.13E−146 | 2.62E−144 |
| LOC100129434 | −3.894209344 | 3.007262804 | 4.37E−145 | 3.64E−143 |
| LOC101929705 | −4.437501451 | 2.306217725 | 4.78E−144 | 3.94E−142 |
| BEX1 | 3.539142258 | 3.293991285 | 8.98E−143 | 7.36E−141 |
| PTGER3 | 4.942760334 | 1.378597776 | 5.40E−142 | 4.39E−140 |
| CHST15 | 3.561893087 | 3.126537951 | 7.52E−142 | 6.08E−140 |
| SUSD4 | 3.945360942 | 2.325580743 | 1.32E−141 | 1.06E−139 |
| TMEM45B | −3.391590991 | 4.19409036 | 1.41E−141 | 1.12E−139 |
| ZNF728 | −5.563710883 | 1.747726106 | 1.44E−141 | 1.14E−139 |
| MDK | −3.186672884 | 5.049174535 | 1.34E−140 | 1.05E−138 |
| KCTD12 | 3.454235324 | 3.339497715 | 8.21E−140 | 6.42E−138 |
| ARHGEF25 | 3.389004251 | 3.598263561 | 2.52E−139 | 1.96E−137 |
| LCN2 | −5.090131493 | 1.697417505 | 5.20E−139 | 4.01E−137 |
| ACADL | −3.13221605 | 5.123610113 | 2.58E−138 | 1.98E−136 |
| OLFM2 | 4.595849966 | 1.511797817 | 4.03E−138 | 3.07E−136 |
| RTN1 | −4.579735247 | 2.154632957 | 2.59E−137 | 1.96E−135 |
| HMGN5 | 3.364899509 | 3.523189701 | 3.63E−137 | 2.72E−135 |
| NR2F1-AS1 | 3.361537305 | 3.592992152 | 6.35E−137 | 4.74E−135 |
| SLC6A20 | 4.178049925 | 1.861381025 | 6.78E−137 | 5.03E−135 |
| TXNIP | −3.047761698 | 6.732751452 | 9.05E−137 | 6.67E−135 |
| SDC2 | 3.08244005 | 5.070159563 | 3.54E−136 | 2.60E−134 |
| TNFRSF19 | −3.040308843 | 6.520713676 | 1.75E−135 | 1.27E−133 |
| SLC15A2 | −4.052846759 | 2.368549805 | 4.90E−135 | 3.54E−133 |
| EFCAB12 | −3.943077078 | 2.601875875 | 9.59E−133 | 6.90E−131 |
| RNF128 | 3.939537307 | 2.030269582 | 1.32E−132 | 9.44E−131 |
| NAP1L2 | 3.148165599 | 4.205042637 | 2.98E−131 | 2.11E−129 |
| MYO1B | −3.011513567 | 5.418375781 | 8.31E−131 | 5.87E−129 |
| FAM105A | −2.999039626 | 5.729588833 | 1.67E−130 | 1.17E−128 |
| RAB3B | −3.02756391 | 5.536761708 | 2.99E−130 | 2.08E−128 |
| SNAI2 | −4.495882901 | 2.038419077 | 3.35E−130 | 2.32E−128 |
| TM4SF1 | −2.999907951 | 5.527009547 | 9.74E−130 | 6.72E−128 |
| CCDC85A | −3.396641773 | 3.490674035 | 1.45E−129 | 9.93E−128 |
| ZC3H12C | −3.529051895 | 3.096154114 | 1.41E−127 | 9.63E−126 |
| NAV2 | −4.564826557 | 1.973621801 | 1.66E−126 | 1.12E−124 |
| MBOAT1 | 3.0622186 | 4.198933503 | 5.81E−125 | 3.91E−123 |
| ISX | −3.894369507 | 2.406115887 | 1.39E−124 | 9.28E−123 |
| AZGP1 | −2.851090919 | 8.353908424 | 4.43E−123 | 2.95E−121 |
| DPP10 | 3.620575558 | 2.238554475 | 5.37E−123 | 3.55E−121 |
| AIDA | 2.86230022 | 6.190379429 | 1.89E−122 | 1.24E−120 |
| SAMD4A | 3.018927938 | 4.150753542 | 4.14E−122 | 2.71E−120 |
| MSX2 | 2.935107472 | 4.101563138 | 4.42E−121 | 2.88E−119 |
| PRKACB | −2.816044334 | 9.108836332 | 8.67E−121 | 5.62E−119 |
| RUNX2 | −4.10154383 | 2.077981034 | 2.69E−120 | 1.74E−118 |
| SLC4A4 | −3.457509283 | 2.865907977 | 1.96E−119 | 1.25E−117 |
| GPRIN2 | −2.936658852 | 4.418627151 | 5.79E−119 | 3.69E−117 |
| MSMB | −3.798744308 | 2.260010911 | 1.42E−118 | 9.00E−117 |
| ARHGAP20 | 3.58144563 | 2.101611244 | 3.71E−118 | 2.34E−116 |
| ZBTB16 | −2.956585914 | 4.157354276 | 3.85E−118 | 2.42E−116 |
| UNC5B | 3.149565747 | 3.066131953 | 1.88E−117 | 1.17E−115 |
| CTNNA2 | −4.322719723 | 1.739498118 | 7.41E−117 | 4.59E−115 |
| IGF1R | −3.101069155 | 3.890408964 | 3.01E−116 | 1.86E−114 |
| HIST1H2BM | −2.822318491 | 5.573836033 | 2.23E−115 | 1.37E−113 |
| LGI2 | 2.845323209 | 4.121736267 | 5.92E−115 | 3.61E−113 |
| DEPTOR | 2.751538115 | 5.751137297 | 1.07E−113 | 6.48E−112 |
| PTPN21 | −2.844774538 | 4.671996363 | 2.20E−113 | 1.33E−111 |
| DLX1 | −3.380297393 | 2.841106703 | 2.48E−113 | 1.49E−111 |
| RNF217 | 3.835444152 | 1.563473426 | 4.16E−113 | 2.49E−111 |
| CHRDL1 | 3.173898116 | 2.710576396 | 2.40E−112 | 1.43E−110 |
| TMEM173 | −4.124330636 | 1.74310642 | 5.61E−111 | 3.32E−109 |
| DUSP5 | 3.363099946 | 2.131321923 | 1.01E−110 | 5.96E−109 |
| LOX | −3.880991917 | 1.901492625 | 6.41E−110 | 3.75E−108 |
| TSPAN5 | 3.015080173 | 3.06888748 | 2.39E−109 | 1.39E−107 |
| SNHG3 | −2.668667597 | 7.343040907 | 2.67E−109 | 1.55E−107 |
| MACROD1 | 2.693205796 | 5.349741489 | 1.63E−108 | 9.43E−107 |
| SYNE1 | 3.456661333 | 1.960003806 | 2.04E−108 | 1.17E−106 |
| ADRB1 | −3.778684045 | 1.944732267 | 6.88E−108 | 3.93E−106 |
| CYP39A1 | −3.35172677 | 2.386904086 | 4.57E−107 | 2.60E−105 |
| GMPR | −3.656622755 | 2.086992135 | 2.12E−105 | 1.20E−103 |
| LRG1 | −3.796074845 | 1.974885988 | 5.91E−105 | 3.33E−103 |
| TNS1 | 2.838650365 | 3.494617197 | 7.88E−105 | 4.42E−103 |
| MAPRE2 | 2.829123283 | 3.557189356 | 1.58E−104 | 8.81E−103 |
| C22ORF34 | 3.389284302 | 1.828891548 | 6.46E−104 | 3.59E−102 |
| JAG1 | −2.652241908 | 5.010421897 | 3.78E−103 | 2.09E−101 |
| EFNA3 | 2.601894661 | 5.620888853 | 8.04E−103 | 4.42E−101 |
| JAKMIP1 | 2.670071724 | 4.035103979 | 1.07E−102 | 5.87E−101 |
| C5ORF38 | 3.474626884 | 1.634850357 | 2.76E−102 | 1.51E−100 |
| ELOVL5 | −2.552843646 | 9.466379371 | 8.63E−102 | 4.69E−100 |
| UNC5A | −3.792371157 | 1.82678097 | 1.20E−101 | 6.50E−100 |

TABLE 3-continued

| Gene | logFC | logCPM | PValue | FDR |
|---|---|---|---|---|
| MAST1 | 3.053410645 | 2.4505874 | 5.91E-101 | 3.18E-99 |
| FCGRT | 3.161267082 | 2.078451917 | 3.70E-99 | 1.98E-97 |
| SIPA1L2 | -2.654419042 | 4.280158593 | 1.19E-98 | 6.34E-97 |
| CNTNAP2 | -3.205185016 | 2.341403589 | 2.02E-98 | 1.07E-96 |
| BCL2L14 | -3.655801193 | 1.784380353 | 2.90E-98 | 1.53E-96 |
| ZNF256 | -3.220691922 | 2.39776348 | 4.15E-98 | 2.18E-96 |
| CCNO | 3.125747639 | 2.086509718 | 6.25E-98 | 3.27E-96 |
| ATP1B1 | 2.497115561 | 8.34501681 | 9.11E-98 | 4.75E-96 |
| NPPC | -3.820954663 | 1.803113561 | 1.15E-97 | 5.95E-96 |
| FOXD4 | -3.561860335 | 1.925893684 | 1.38E-97 | 7.14E-96 |
| NKX3-1 | -2.502123267 | 7.750556922 | 1.70E-97 | 8.76E-96 |
| NR3C2 | -2.802324868 | 3.617661178 | 3.85E-97 | 1.97E-95 |
| GPR133 | 2.560022718 | 4.539046676 | 4.83E-97 | 2.46E-95 |
| SGK223 | -3.075524384 | 2.689795666 | 5.26E-97 | 2.67E-95 |
| TMPRSS2 | -2.472630011 | 7.997257326 | 1.04E-95 | 5.24E-94 |
| GJB1 | 2.643886799 | 3.789579523 | 2.43E-95 | 1.22E-93 |
| AMIGO2 | 3.187669717 | 1.849253385 | 2.69E-95 | 1.35E-93 |
| PTP4A3 | 2.802580723 | 2.885732417 | 5.26E-95 | 2.62E-93 |
| DPYSL4 | -3.115112713 | 2.421383428 | 1.14E-94 | 5.66E-93 |
| SH3BGRL | 2.5045915 | 5.012306749 | 1.48E-94 | 7.32E-93 |
| MMD | -2.517525583 | 4.858093231 | 2.27E-94 | 1.12E-92 |
| NRXN3 | -3.580590928 | 1.77207053 | 1.98E-93 | 9.70E-92 |
| LOC100130872 | -3.420422768 | 1.742862931 | 1.76E-92 | 8.57E-91 |
| NAP1L3 | 3.29523675 | 1.50466782 | 2.04E-92 | 9.92E-91 |
| EPHX1 | 2.391484999 | 8.854469437 | 1.16E-90 | 5.63E-89 |
| NIPC2 | -2.373867934 | 9.122884678 | 1.74E-89 | 8.37E-88 |
| PART1 | -2.973247823 | 2.402940935 | 1.99E-89 | 9.54E-88 |
| NPTX2 | 2.417801091 | 4.97583533 | 5.58E-89 | 2.67E-87 |
| ITGA1 | -3.181070249 | 1.914041291 | 6.57E-89 | 3.13E-87 |
| INPP4B | -2.54145262 | 3.791418006 | 8.96E-89 | 4.25E-87 |
| AUTS2 | 2.834826488 | 2.234245062 | 1.91E-87 | 9.04E-86 |
| WLS | 2.372932073 | 5.019863818 | 3.85E-86 | 1.81E-84 |
| SYTL2 | 2.346790146 | 5.83749823 | 6.76E-86 | 3.17E-84 |
| MCTP2 | -2.339596687 | 6.539094791 | 1.04E-85 | 4.85E-84 |
| SLC43A1 | -2.32654411 | 7.137810286 | 2.51E-85 | 1.17E-83 |
| BEX5 | 2.635217401 | 2.863948306 | 3.72E-85 | 1.72E-83 |
| CT45A10 | 2.850146218 | 2.097130487 | 6.71E-85 | 3.10E-83 |
| LCP1 | -2.32231855 | 6.583895182 | 1.38E-84 | 6.34E-83 |
| TRIM2 | -2.395255457 | 4.628674113 | 1.48E-84 | 6.79E-83 |
| MED12L | 2.49038413 | 3.439947999 | 5.26E-84 | 2.40E-82 |
| GDF1 | 2.566585495 | 3.00101401 | 8.78E-84 | 3.99E-82 |
| PGM1 | 2.321539031 | 5.311638769 | 1.76E-83 | 7.96E-82 |
| NLRC5 | 2.519831703 | 3.186923879 | 6.08E-83 | 2.74E-81 |
| DTX3 | 2.795742699 | 2.074700437 | 1.37E-82 | 6.16E-81 |
| MICAL1 | -2.293855433 | 6.137975123 | 3.45E-82 | 1.54E-80 |
| ARHGAP22 | 2.697340649 | 2.336505528 | 5.32E-82 | 2.37E-80 |
| AGR2 | -2.875579308 | 2.330753156 | 8.14E-82 | 3.62E-80 |
| RUNX1 | -3.011426709 | 2.219413344 | 1.04E-81 | 4.58E-80 |
| GYG2 | 2.373938301 | 3.628184132 | 1.89E-81 | 8.31E-80 |
| MAN1A1 | 2.378817805 | 3.645068865 | 2.09E-81 | 9.16E-80 |
| DIO1 | 2.524899377 | 3.010548753 | 4.64E-81 | 2.03E-79 |
| TRPV3 | 2.759344091 | 2.081043316 | 4.67E-81 | 2.04E-79 |
| STOX2 | 2.576363499 | 2.677973224 | 6.74E-81 | 2.93E-79 |
| CLSTN3 | 2.268879546 | 5.640136384 | 1.26E-80 | 5.47E-79 |
| MYBPC1 | -2.58587835 | 2.993481509 | 3.01E-80 | 1.30E-78 |
| KRT19 | -2.537641882 | 3.272772725 | 9.47E-80 | 4.07E-78 |
| CDC14B | -2.531326594 | 3.137658805 | 1.29E-79 | 5.52E-78 |
| TMEM37 | 2.406741083 | 3.533343514 | 3.73E-79 | 1.59E-77 |
| NAT8L | 2.424739303 | 3.3251965 | 4.53E-79 | 1.93E-77 |
| ANXA9 | 2.301250284 | 4.076998361 | 9.66E-79 | 4.09E-77 |
| SH3PXD2A | -2.506253625 | 3.312671511 | 9.82E-79 | 4.14E-77 |
| ENTPD3 | 2.806508385 | 1.829631184 | 1.92E-78 | 8.06E-77 |
| CERS1 | 2.395504524 | 3.437655018 | 3.28E-78 | 1.37E-76 |
| PDE9A | -2.35026776 | 4.053240103 | 3.27E-78 | 1.37E-76 |
| KLK15 | -2.625730382 | 2.631912273 | 1.51E-77 | 6.27E-76 |
| STARD4 | -2.264713962 | 4.423508924 | 3.23E-77 | 1.34E-75 |
| NOTCH3 | 2.220489554 | 5.334964727 | 4.06E-77 | 1.68E-75 |
| ANK2 | 2.504390337 | 2.639602646 | 1.86E-76 | 7.65E-75 |
| CRISP3 | -2.55053158 | 2.683900206 | 2.02E-76 | 8.27E-75 |
| PTRF | 2.271215237 | 3.662195878 | 1.99E-75 | 8.12E-74 |
| ACSL3 | -2.157914356 | 9.154882898 | 2.15E-75 | 8.75E-74 |
| ENDOD1 | -2.1583515 | 8.534999408 | 2.70E-75 | 1.10E-73 |
| CA12 | 2.179323802 | 5.566342205 | 6.58E-75 | 2.66E-73 |
| RND3 | -2.238268581 | 4.397559715 | 1.40E-74 | 5.65E-73 |
| GHR | 2.153951016 | 6.454984557 | 3.14E-74 | 1.26E-72 |
| LZTS3 | 2.351505219 | 3.237263468 | 3.73E-74 | 1.49E-72 |
| SLC44A4 | -2.153078671 | 6.670094606 | 6.49E-74 | 2.59E-72 |
| DUSP27 | -2.82770872 | 2.040708119 | 6.91E-74 | 2.74E-72 |

TABLE 3-continued

| Gene | logFC | logCPM | PValue | FDR |
|---|---|---|---|---|
| CXXC5 | 2.205873879 | 4.368433071 | 7.17E−74 | 2.84E−72 |
| SYNGR1 | 2.245041679 | 3.682125416 | 8.11E−74 | 3.20E−72 |
| SPG20 | −2.146613324 | 6.917107479 | 8.79E−74 | 3.46E−72 |
| TMEM121 | 2.59801925 | 2.128525033 | 1.46E−73 | 5.73E−72 |
| IRX2 | 2.572672835 | 2.154257782 | 2.35E−73 | 9.20E−72 |
| MID1 | 2.353486065 | 3.055509886 | 3.46E−73 | 1.35E−71 |
| ZNF737 | −2.280160868 | 3.611153685 | 4.98E−73 | 1.93E−71 |
| GLIPR2 | −2.43576554 | 3.047257491 | 7.05E−73 | 2.73E−71 |
| SAMD12 | 2.218334782 | 3.825421572 | 8.11E−73 | 3.13E−71 |
| ZNF629 | 2.212391448 | 3.90705806 | 8.88E−73 | 3.41E−71 |
| RIMS3 | 2.228171294 | 3.623909795 | 1.31E−72 | 5.01E−71 |
| FZD7 | 2.333508871 | 3.108295271 | 2.82E−72 | 1.08E−70 |
| MAGEA10 | 2.135509536 | 5.55411234 | 3.92E−72 | 1.49E−70 |
| ITPR1 | 2.162458918 | 4.600687489 | 4.16E−72 | 1.58E−70 |
| RAB36 | −2.698130722 | 2.259637514 | 6.29E−72 | 2.38E−70 |
| ADAMTS1 | −2.107582382 | 7.598076639 | 9.16E−72 | 3.45E−70 |
| GAS6 | 2.194846946 | 3.880089431 | 1.22E−71 | 4.58E−70 |
| STK39 | −2.102752028 | 7.863010498 | 1.32E−71 | 4.95E−70 |
| BMF | −2.477674484 | 2.78642905 | 1.48E−71 | 5.52E−70 |
| DSC2 | −2.160639104 | 4.879770945 | 7.62E−71 | 2.84E−69 |
| IL27RA | 2.439963728 | 2.391125748 | 9.52E−71 | 3.53E−69 |
| PFN2 | 2.085282526 | 7.081366729 | 2.26E−70 | 8.36E−69 |
| GNG7 | 2.340949881 | 2.840630794 | 2.76E−70 | 1.02E−68 |
| ID1 | 2.098225003 | 5.68104117 | 4.89E−70 | 1.80E−68 |
| ACSL4 | −2.64470627 | 1.888823824 | 1.23E−68 | 4.52E−67 |
| ABLIM3 | 2.574442337 | 1.796919101 | 1.71E−68 | 6.25E−67 |
| DPP10-AS1 | 2.391181897 | 2.399236876 | 4.63E−68 | 1.68E−66 |
| CSRNP3 | 2.397203899 | 2.369082722 | 5.17E−68 | 1.87E−66 |
| GSTA1 | −2.304935013 | 3.055381896 | 7.45E−68 | 2.70E−66 |
| LINC00886 | 2.559871243 | 1.805051827 | 1.17E−67 | 4.23E−66 |
| TMTC2 | −2.097747244 | 4.806627496 | 1.62E−67 | 5.82E−66 |
| TTPA | 2.25027439 | 3.071605776 | 2.54E−67 | 9.11E−66 |
| PPAP2C | 2.107376865 | 4.080909343 | 3.52E−67 | 1.26E−65 |
| SEMA3F | 2.059637644 | 5.210552897 | 3.93E−67 | 1.40E−65 |
| FAM184A | 2.243911873 | 3.022096869 | 6.34E−67 | 2.25E−65 |
| SLC1A1 | 2.379659075 | 2.321199488 | 1.22E−66 | 4.33E−65 |
| SLC41A2 | 2.091806611 | 4.206279401 | 1.41E−66 | 4.98E−65 |
| ZNF702P | −2.633135334 | 1.882240407 | 1.52E−66 | 5.37E−65 |
| SMARCD3 | 2.040913883 | 5.55783772 | 1.87E−66 | 6.55E−65 |
| NBPF1 | −2.069468359 | 5.165236683 | 2.55E−66 | 8.94E−65 |
| ATP6AP1L | 2.444731474 | 2.038839089 | 2.82E−66 | 9.82E−65 |
| HOMER2 | −2.050449348 | 5.559761092 | 2.95E−66 | 1.03E−64 |
| CLDN8 | −2.307155213 | 2.940282291 | 3.43E−66 | 1.19E−64 |
| FYN | 2.43041537 | 2.065759986 | 3.59E−66 | 1.24E−64 |
| HMGN2P46 | −2.110316314 | 4.173155562 | 4.58E−66 | 1.58E−64 |
| C11ORF70 | 2.333611951 | 2.464874625 | 3.76E−65 | 1.29E−63 |
| TUBB6 | 2.046018964 | 4.604880287 | 4.16E−65 | 1.43E−63 |
| AIM1 | −2.048888628 | 5.077377533 | 4.65E−65 | 1.59E−63 |
| DLG2 | −2.38992494 | 2.382772657 | 4.74E−65 | 1.62E−63 |
| TOX3 | −2.146144761 | 3.649284368 | 6.06E−65 | 2.06E−63 |
| GPR161 | −2.309539559 | 2.820781047 | 9.09E−65 | 3.08E−63 |
| PTPRM | −2.069147771 | 4.336512126 | 1.47E−64 | 4.95E−63 |
| DEGS1 | −1.982001248 | 7.835060646 | 2.37E−64 | 7.99E−63 |
| FAM110B | −2.073809267 | 4.393867988 | 3.84E−64 | 1.29E−62 |
| OVGP1 | −2.106315701 | 3.587820663 | 7.57E−64 | 2.54E−62 |
| C17ORF107 | 2.231899233 | 2.63177853 | 3.22E−63 | 1.07E−61 |
| VAV3 | 2.242218786 | 2.61915326 | 3.89E−63 | 1.30E−61 |
| NUDT11 | 2.151745354 | 3.144013619 | 4.79E−63 | 1.59E−61 |
| TGFA | 2.144595489 | 3.161070595 | 9.22E−63 | 3.05E−61 |
| LRRC31 | 2.022242474 | 4.272761945 | 1.43E−62 | 4.71E−61 |
| KANK1 | −2.095012394 | 3.703811502 | 1.69E−62 | 5.56E−61 |
| MAOA | −1.940481017 | 8.655707043 | 3.91E−62 | 1.28E−60 |
| MESP1 | −2.005147634 | 4.727857442 | 6.46E−62 | 2.12E−60 |
| FAS | 2.009663581 | 4.15271048 | 1.64E−61 | 5.36E−60 |
| CLYBL | 2.101885837 | 3.327911397 | 2.34E−61 | 7.62E−60 |
| PDGFRL | 2.368426733 | 1.923557636 | 4.89E−61 | 1.59E−59 |
| PRKD1 | 1.918083366 | 7.73014995 | 9.97E−61 | 3.23E−59 |
| CERK | −2.037084781 | 3.774108291 | 1.17E−60 | 3.76E−59 |
| DHRS7 | −1.916014781 | 8.130288454 | 1.20E−60 | 3.86E−59 |
| IFITM2 | −2.17592753 | 3.107759159 | 2.31E−60 | 7.40E−59 |
| GALNT14 | 2.122625064 | 2.956792884 | 2.65E−60 | 8.49E−59 |
| DYRK3 | 2.102508782 | 3.049924829 | 5.39E−60 | 1.72E−58 |
| HES1 | 1.944315056 | 4.917303995 | 5.93E−60 | 1.89E−58 |
| STEAP1 | −1.901835322 | 8.187652713 | 6.89E−60 | 2.19E−58 |
| CSGALNACT1 | −2.15932157 | 2.972050938 | 1.10E−59 | 3.47E−58 |
| RGS11 | 2.284688761 | 2.105818811 | 1.32E−59 | 4.18E−58 |
| ZDHHC2 | 1.914772766 | 5.79814496 | 2.00E−59 | 6.31E−58 |
| TRIM34 | 2.379249279 | 1.792516616 | 2.51E−59 | 7.90E−58 |

TABLE 3-continued

| Gene | logFC | logCPM | PValue | FDR |
|---|---|---|---|---|
| SLFN5 | 1.921288164 | 5.175083226 | 3.90E−59 | 1.22E−57 |
| SPSB1 | −2.279734729 | 2.575568738 | 3.94E−59 | 1.23E−57 |
| BOC | 2.32537206 | 1.869913969 | 7.44E−59 | 2.32E−57 |
| TRIM6-TRIM34 | 2.309859345 | 1.967739194 | 8.43E−59 | 2.62E−57 |
| MAPK8IP2 | −1.976164063 | 4.295635988 | 8.98E−59 | 2.79E−57 |
| TPPP | 1.934662792 | 4.356085101 | 2.61E−58 | 8.06E−57 |
| EAF2 | −1.971318544 | 3.620514839 | 4.52E−58 | 1.39E−56 |
| ZNF625 | −2.443802386 | 1.869906223 | 7.98E−58 | 2.45E−56 |
| TNFSF15 | −2.205350259 | 2.55660687 | 1.35E−57 | 4.16E−56 |
| STXBP5-AS1 | −2.28258706 | 2.349164679 | 1.50E−57 | 4.59E−56 |
| BBS10 | −1.866428853 | 6.527005698 | 2.78E−57 | 8.49E−56 |
| CLU | 1.872694077 | 5.698295195 | 4.95E−57 | 1.51E−55 |
| ZMYND12 | 2.087625177 | 2.828968563 | 5.03E−57 | 1.53E−55 |
| ID3 | 1.869759894 | 5.827636323 | 5.88E−57 | 1.78E−55 |
| VWDE | 2.197879192 | 2.199190081 | 5.89E−57 | 1.78E−55 |
| PROS1 | 2.063496372 | 2.902665743 | 6.68E−57 | 2.01E−55 |
| CCDC136 | −2.147539504 | 2.87906061 | 1.15E−56 | 3.44E−55 |
| TMSB4X | −2.165634469 | 2.369609956 | 2.93E−56 | 8.78E−55 |
| KLF4 | −2.064883321 | 3.018670661 | 2.94E−56 | 8.80E−55 |
| NLGN1 | 1.864582567 | 5.39341146 | 3.11E−56 | 9.28E−55 |
| C1QTNF9B-AS1 | −2.392846197 | 1.937481055 | 3.35E−56 | 9.97E−55 |
| RALGPS2 | 1.869239647 | 5.061074657 | 4.70E−56 | 1.39E−54 |
| KIF5C | 1.853217651 | 5.759657313 | 4.73E−56 | 1.40E−54 |
| CNTN3 | 1.945763565 | 3.459945389 | 4.95E−56 | 1.46E−54 |
| RAB27A | −1.990436727 | 3.300895119 | 5.33E−56 | 1.57E−54 |
| RGS2 | −2.119797506 | 2.624362645 | 7.38E−56 | 2.17E−54 |
| CPT1C | 2.046663192 | 2.856369305 | 1.06E−55 | 3.12E−54 |
| ZNF814 | −1.946560055 | 3.928856796 | 1.35E−55 | 3.94E−54 |
| PAM | 1.892846465 | 4.108063403 | 2.57E−55 | 7.50E−54 |
| EOMES | 2.157105256 | 2.160031785 | 2.82E−55 | 8.20E−54 |
| FKBP5 | −1.827487051 | 6.909174349 | 5.35E−55 | 1.55E−53 |
| RANGRF | −2.214618866 | 2.346491156 | 7.45E−55 | 2.16E−53 |
| ASPH | 1.803221644 | 10.37749889 | 1.44E−54 | 4.16E−53 |
| B4GALNT1 | 1.869395012 | 4.290065659 | 1.77E−54 | 5.08E−53 |
| LOC101927934 | 2.189415325 | 2.027457734 | 1.84E−54 | 5.30E−53 |
| LEF1 | 2.007698079 | 2.889155725 | 2.55E−54 | 7.31E−53 |
| BCL11B | −2.348682058 | 1.874102671 | 2.59E−54 | 7.41E−53 |
| NOS3 | 1.878005275 | 3.945043114 | 5.46E−54 | 1.56E−52 |
| PPP2R2C | 1.848051577 | 4.420542427 | 8.56E−54 | 2.43E−52 |
| DNASE2B | −2.069413977 | 2.845763588 | 1.88E−53 | 5.34E−52 |
| TPBG | 2.136067682 | 2.080527171 | 2.39E−53 | 6.78E−52 |
| UAP1 | −1.783668937 | 8.553963646 | 2.53E−53 | 7.15E−52 |
| HS6ST2 | 1.882952616 | 3.644073366 | 2.67E−53 | 7.53E−52 |
| LTN1 | −1.805526643 | 5.498497545 | 4.17E−53 | 1.17E−51 |
| RAB39B | 2.166519265 | 1.944343522 | 4.63E−53 | 1.30E−51 |
| GUCY1A3 | −1.791112034 | 6.647979736 | 5.42E−53 | 1.52E−51 |
| SPECC1L-ADORA2A | −1.792642346 | 6.635233403 | 5.62E−53 | 1.57E−51 |
| SORL1 | 1.819471612 | 4.725480995 | 6.75E−53 | 1.88E−51 |
| HLF | −1.858704255 | 4.231025583 | 7.99E−53 | 2.22E−51 |
| KRT80 | 2.08956367 | 2.180425953 | 8.95E−53 | 2.48E−51 |
| DOCK3 | 1.957425077 | 3.064427831 | 9.80E−53 | 2.71E−51 |
| CHSY1 | −1.810590408 | 5.266642917 | 1.94E−52 | 5.36E−51 |
| CAB39L | −1.777849376 | 6.562849551 | 2.47E−52 | 6.80E−51 |
| PCAT1 | −1.934803817 | 3.279622644 | 3.13E−52 | 8.60E−51 |
| STXBP5 | −1.775641802 | 6.168492956 | 9.06E−52 | 2.48E−50 |
| LPPR1 | 1.97507189 | 2.704632979 | 1.18E−51 | 3.22E−50 |
| C9ORF152 | −2.1192141 | 2.686061303 | 1.43E−51 | 3.91E−50 |
| CLVS1 | 1.778187287 | 5.399991319 | 1.55E−51 | 4.23E−50 |
| LTBP1 | 1.835610802 | 3.703765663 | 2.99E−51 | 8.11E−50 |
| SERPINI1 | 2.123929129 | 1.973246657 | 3.31E−51 | 8.97E−50 |
| GNAQ | −2.134316348 | 2.259061934 | 5.13E−51 | 1.39E−49 |
| SPECC1L | −1.745221905 | 7.099881309 | 9.75E−51 | 2.63E−49 |
| TENC1 | −1.774605902 | 5.341668227 | 1.06E−50 | 2.84E−49 |
| PPFIA2 | −1.742650003 | 7.072852122 | 1.19E−50 | 3.18E−49 |
| HIVEP3 | 2.021246628 | 2.234409299 | 1.62E−50 | 4.34E−49 |
| LAMB1 | −1.784594735 | 4.801247477 | 1.82E−50 | 4.85E−49 |
| GFI1 | 2.132953963 | 1.795175945 | 2.00E−50 | 5.32E−49 |
| LAPTM4B | 1.735980302 | 6.720598364 | 2.67E−50 | 7.10E−49 |
| CENPN | −1.721930244 | 8.193489066 | 5.91E−50 | 1.57E−48 |
| TRIP10 | 1.787340817 | 4.070897539 | 9.54E−50 | 2.52E−48 |
| CLGN | −1.71772438 | 7.21720101 | 1.99E−49 | 5.24E−48 |
| ST8SIA4 | 1.984339273 | 2.416794335 | 2.35E−49 | 6.19E−48 |
| UBA7 | 2.04774997 | 2.047725482 | 3.00E−49 | 7.90E−48 |
| BACE2 | 2.002743849 | 2.255815813 | 3.18E−49 | 8.33E−48 |
| ZBTB20 | 1.887389272 | 2.937625904 | 3.60E−49 | 9.41E−48 |
| ADCY7 | 1.765706957 | 4.268810737 | 3.71E−49 | 9.69E−48 |
| TMEM56 | 1.727178783 | 5.623467271 | 4.64E−49 | 1.21E−47 |
| DNAJC6 | 1.934409069 | 2.566790464 | 7.00E−49 | 1.82E−47 |

TABLE 3-continued

| Gene | logFC | logCPM | PValue | FDR |
|---|---|---|---|---|
| CXADR | -1.712875437 | 5.748261907 | 2.80E-48 | 7.26E-47 |
| VIM | 1.708222931 | 5.717850734 | 3.13E-48 | 8.11E-47 |
| BVES | 1.945495509 | 2.405439542 | 3.25E-48 | 8.40E-47 |
| LIX1L | 1.814454052 | 3.173324019 | 3.63E-48 | 9.36E-47 |
| ADRB2 | -1.737009633 | 4.782584268 | 6.74E-48 | 1.73E-46 |
| HERC3 | -1.70993689 | 5.427779547 | 1.43E-47 | 3.68E-46 |
| ACPP | -1.789737229 | 3.538681825 | 2.56E-47 | 6.55E-46 |
| ZNF697 | -1.792917268 | 3.595184979 | 3.12E-47 | 7.97E-46 |
| RHOU | -1.668687182 | 7.232639295 | 7.67E-47 | 1.96E-45 |
| GALNT3 | 1.680366617 | 5.663253204 | 1.00E-46 | 2.55E-45 |
| PRKAA2 | -1.718607914 | 4.588409105 | 1.18E-46 | 3.00E-45 |
| BCAP29 | -1.659419321 | 6.653825078 | 2.63E-46 | 6.67E-45 |
| VWA5A | 1.828068489 | 2.969464251 | 4.19E-46 | 1.06E-44 |
| HFE | 1.738909661 | 3.651671267 | 5.40E-46 | 1.36E-44 |
| LOC100288152 | 1.840871139 | 2.839298882 | 5.72E-46 | 1.44E-44 |
| LINC00472 | 1.977814503 | 2.056157128 | 6.31E-46 | 1.58E-44 |
| FLJ23867 | 1.660208055 | 5.755386524 | 7.95E-46 | 1.99E-44 |
| ANTXR1 | 1.695275664 | 4.330520935 | 8.92E-46 | 2.23E-44 |
| GNG4 | 1.870544327 | 2.543954266 | 1.08E-45 | 2.69E-44 |
| MROH6 | -1.86625102 | 2.770561856 | 1.20E-45 | 2.99E-44 |
| MALT1 | -1.655199626 | 6.222774635 | 1.26E-45 | 3.14E-44 |
| LHX4 | 2.025063244 | 1.752806961 | 1.48E-45 | 3.68E-44 |
| SPATA18 | 1.732173911 | 3.524500216 | 1.96E-45 | 4.85E-44 |
| FAM198A | 1.803983226 | 2.990610756 | 2.14E-45 | 5.27E-44 |
| TDRD9 | 1.952892539 | 1.997355927 | 2.80E-45 | 6.91E-44 |
| SNORD116-21 | -1.89541612 | 2.697050348 | 3.09E-45 | 7.59E-44 |
| ATF3 | 1.656557832 | 5.351652296 | 3.52E-45 | 8.63E-44 |
| SORBS1 | 1.740286391 | 3.272759882 | 4.03E-45 | 9.87E-44 |
| DSG2 | -1.628329961 | 7.557589188 | 7.12E-45 | 1.74E-43 |
| MAPT | 1.671411958 | 4.3899522 | 9.61E-45 | 2.34E-43 |
| SLC22A17 | 1.670062582 | 4.355606318 | 1.62E-44 | 3.94E-43 |
| EPAS1 | 1.963233061 | 1.855302653 | 1.81E-44 | 4.38E-43 |
| SLC22A31 | 1.728003063 | 3.369206965 | 1.89E-44 | 4.57E-43 |
| RAB6B | 1.647562995 | 5.0575834 | 1.91E-44 | 4.61E-43 |
| GALNS | 1.696434462 | 3.730962456 | 2.09E-44 | 5.05E-43 |
| BTG2 | 1.645917277 | 4.986572322 | 2.46E-44 | 5.91E-43 |
| ITGB4 | 1.767923821 | 3.079210811 | 2.65E-44 | 6.38E-43 |
| SLC30A4 | -1.614359834 | 7.923995788 | 2.73E-44 | 6.55E-43 |
| SELENBP1 | 1.609751344 | 8.855317716 | 2.94E-44 | 7.02E-43 |
| SLC16A2 | 1.827066605 | 2.487784781 | 1.09E-43 | 2.61E-42 |
| GPR126 | -1.604180461 | 7.512666577 | 1.18E-43 | 2.82E-42 |
| PTPRK | 1.63926059 | 4.637131927 | 1.75E-43 | 4.15E-42 |
| LTB4R | -1.802118184 | 2.930108831 | 2.68E-43 | 6.36E-42 |
| OSBPL8 | -1.591723547 | 7.880578742 | 3.47E-43 | 8.23E-42 |
| IPO5P1 | -1.649542642 | 4.2909434 | 4.95E-43 | 1.17E-41 |
| S100P | -1.635147082 | 4.558206467 | 6.03E-43 | 1.42E-41 |
| MAMDC4 | -1.641148365 | 4.458783516 | 6.79E-43 | 1.60E-41 |
| SORD | -1.582326442 | 8.695122996 | 7.85E-43 | 1.84E-41 |
| ALDH2 | 1.596073057 | 5.978419638 | 8.78E-43 | 2.06E-41 |

Figures 6C, 6D:
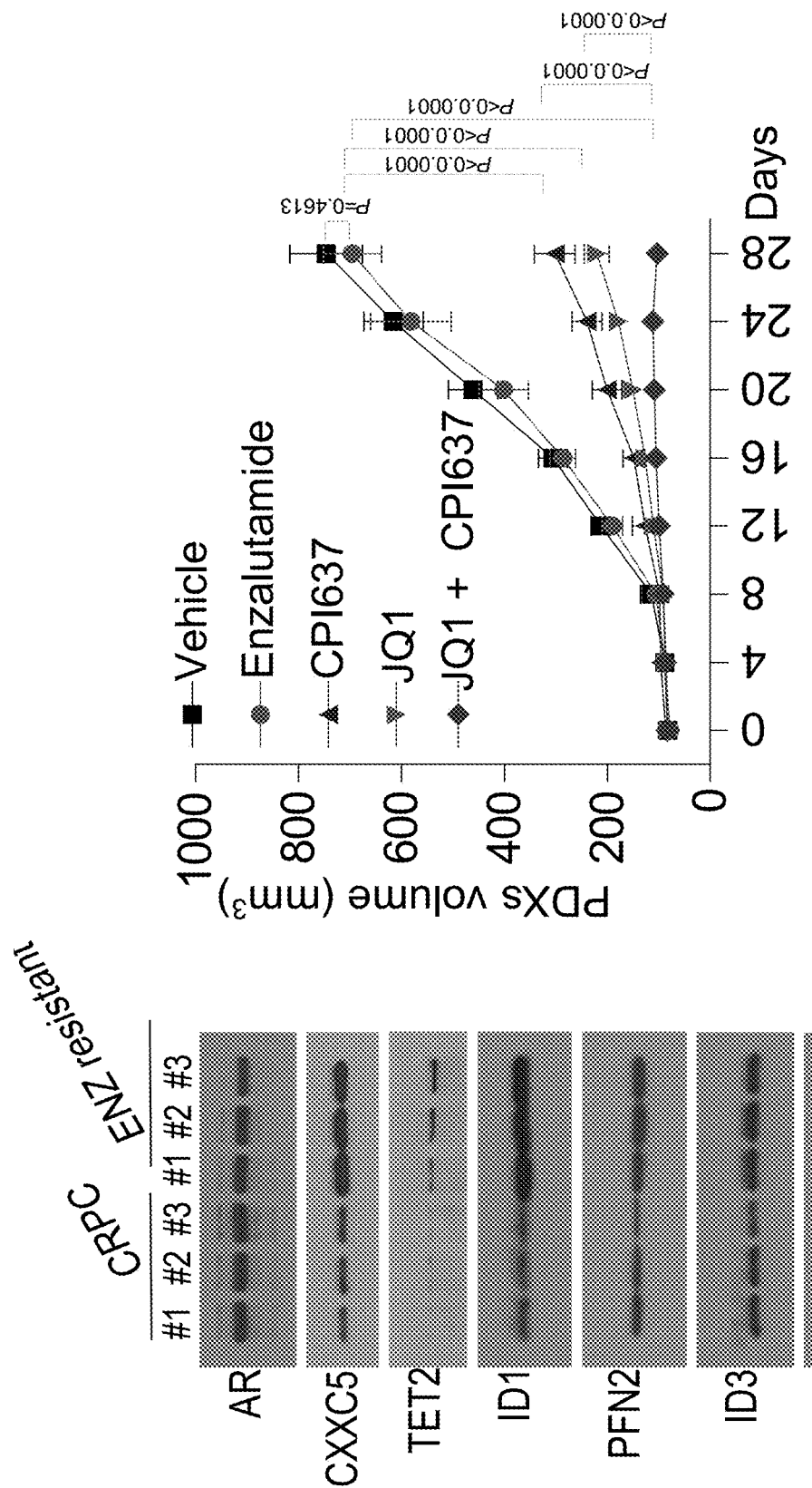
Figure 6E:
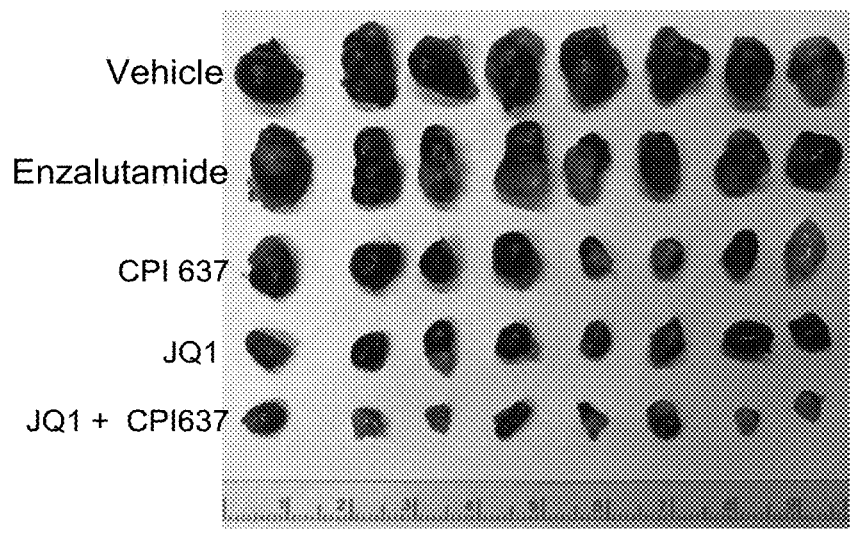

Next, the aim was to target the unorthodox AR program in ENZ-resistant ARPC in a clinically relevant model. To this end, the therapeutic efficiency of the dual inhibition of BET and CBP/p300 signaling pathways in PDX models was evaluated. CRPC and ENZ-resistant PDX models were generated and maintained as reported previously (Kohli et al., *PloS one*, 10:e0145176 (2015)). The in vivo study confirmed that CRPC PDX still responded to ENZ treatment but the ENZ-resistant PDXs did not respond to treatment (FIG. 5C, 5D). Western blot analysis showed that expression of CXXC5 and TET2 and their downstream targets ID1, PFN2, and ID3 was higher in ENZ-resistant PDXs compared to CRPC controls (FIG. 6C). These data indicated that the ENZ-resistant PDX is a suitable model for further study.

Figure 6F:
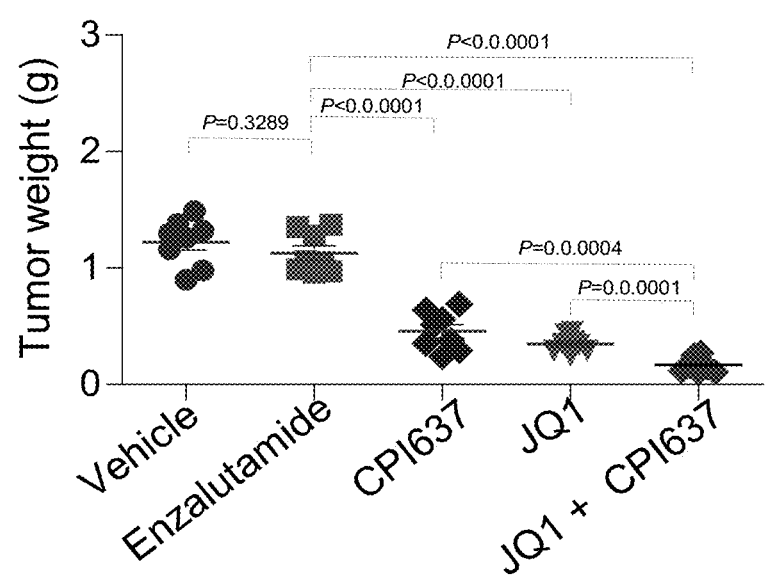
Figure 6G:
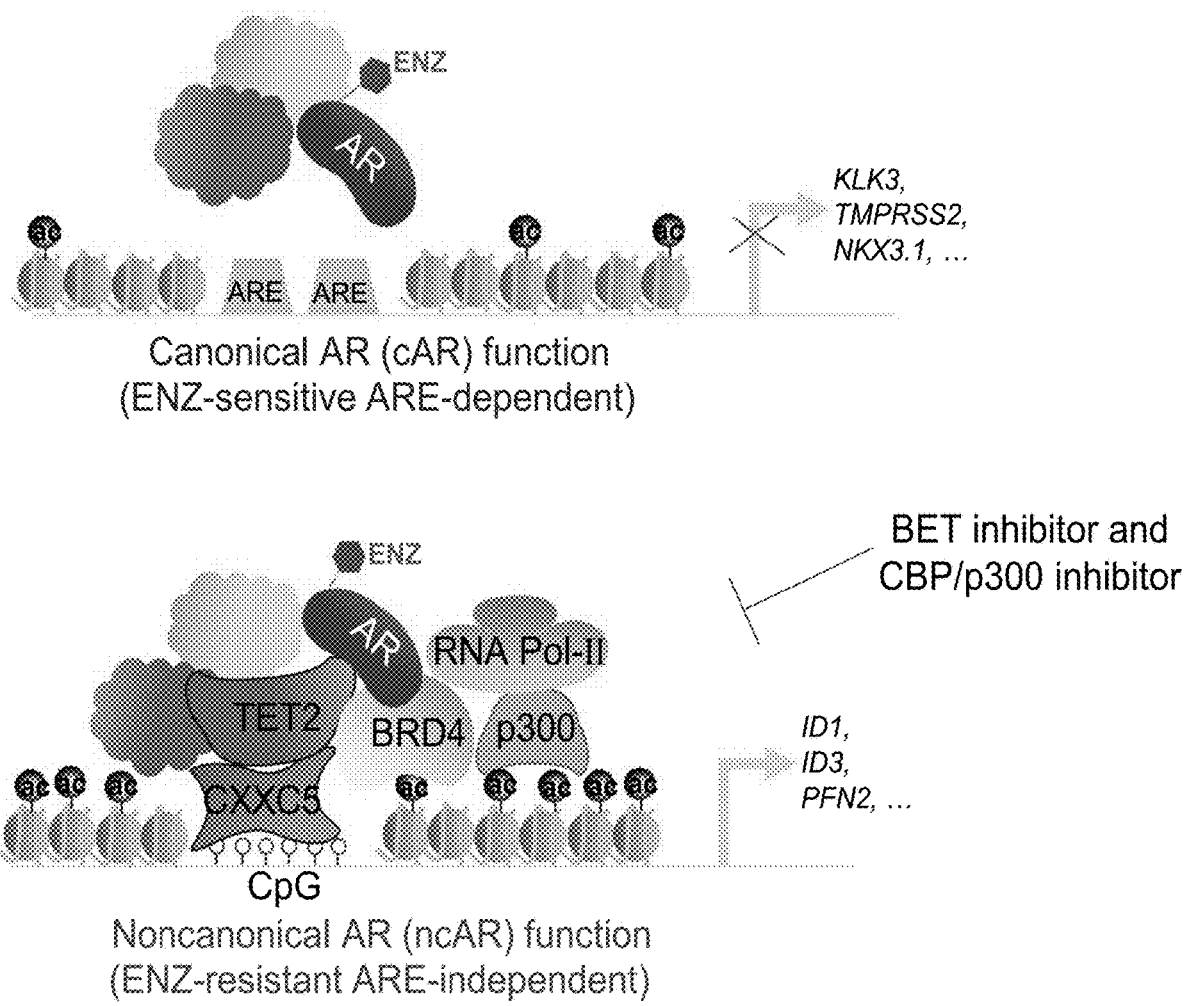

Next, the aim was to establish CRPC control and ENZ-resistant PDXs in castrated male mice and treated mice with vehicle, ENZ, CPI637, JQ1, or combination of CPI637 and JQ1. ENZ-resistant PDXs responded to CPI637 alone, JQ1 alone and combined CPI637 and JQ1 treatment, but not ENZ (FIG. 6D, 6F). The performance of the combined treatment was an improvement over either CPI637 or JQ1 treatment alone (FIG. 6D, 6F). These data suggest that dual inhibition of BET and CBP/p300 signaling pathways can overcome the aberrantly upregulated unorthodox AR program and ENZ resistance in CRPC.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating treatment-resistant prostate cancer, wherein said method comprises:
   (a) identifying a mammal having a treatment-resistant prostate cancer as having an elevated level of a polypeptide as compared to a median level present within a control prostate tissue, wherein said polypeptide is selected from the group consisting of a CXXC5 polypeptide, a CXXC4 polypeptide, a TET2 polypeptide, an ID1 polypeptide, an ID3 polypeptide, and a PFN2 polypeptide, and
   (b) administering one or more targeted therapies to said mammal.

2. The method of claim 1, wherein said mammal is a human.

3. The method of claim 1, wherein said treatment-resistant prostate cancer is an enzalutamide-resistant prostate cancer.

4. The method of claim 1, wherein said treatment-resistant prostate cancer is an enzalutamide-resistant castration-resistant prostate cancer.

5. The method of claim 1, wherein said identifying step comprises detecting the presence of two or more polypeptides of said group.

6. The method of claim 1, wherein said administering one or more targeted therapies comprises administering a BET inhibitor.

7. The method of claim 1, wherein said administering one or more targeted therapies comprises administering a CBP/p300 inhibitor.

8. The method of claim 1, wherein said administering one or more targeted therapies comprises administering a CBP/p300 and a BET inhibitor.

9. The method of claim 1, wherein said administering one or more targeted therapies comprises administering JQ1 and administering CPI637.

10. The method of claim 1, wherein said administering step further comprises administering one or more chemotherapeutic agents.

11. A method for treating treatment-resistant prostate cancer, wherein said method comprises administering, to a mammal having treatment-resistant prostate cancer and identified as having an elevated level of a polypeptide, one or more targeted therapies, wherein said polypeptide is selected from the group consisting of a CXXC5 polypeptide, a CXXC4 polypeptide, a TET2 polypeptide, an ID1 polypeptide, an ID3 polypeptide, and a PFN2 polypeptide.

12. The method of claim 11, wherein said mammal is a human.

13. The method of claim 11, wherein said treatment-resistant prostate cancer is an enzalutamide-resistant prostate cancer.

14. The method of claim 11, wherein said treatment-resistant prostate cancer is an enzalutamide-resistant castration-resistant prostate cancer.

15. The method of claim 11, wherein said mammal is a mammal identified as having an elevated level of two or more polypeptides of said group.

16. The method of claim 11, wherein administering said one or more targeted therapies comprises administering a BET inhibitor.

17. The method of claim 11, wherein administering said one or more targeted therapies comprises administering a CBP/p300 inhibitor.

18. The method of claim 11, wherein administering said one or more targeted therapies comprises administering a CBP/p300 and a BET inhibitor.

19. The method of claim 11, wherein administering one or more targeted therapies comprises administering JQ1 and administering CPI637.

20. The method of claim 11, wherein said administering step further comprises administering one or more chemotherapeutic agents.

* * * * *